(12) United States Patent
Gross et al.

(10) Patent No.: US 9,950,156 B2
(45) Date of Patent: Apr. 24, 2018

(54) DISC THERAPY

(71) Applicant: RAINBOW MEDICAL LTD., Herzliya (IL)

(72) Inventors: Yossi Gross, Moshav Mazor (IL); Zev Sohn, Ginot Shomron (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

(21) Appl. No.: 15/263,910

(22) Filed: Sep. 13, 2016

(65) Prior Publication Data

US 2018/0071523 A1 Mar. 15, 2018

(51) Int. Cl.
| | | |
|---|---|---|
| *A61N 1/00* | (2006.01) | |
| *A61N 1/20* | (2006.01) | |
| *A61N 1/05* | (2006.01) | |
| *A61N 1/36* | (2006.01) | |

(52) U.S. Cl.
CPC ............ *A61N 1/205* (2013.01); *A61N 1/0551* (2013.01); *A61N 1/3606* (2013.01)

(58) Field of Classification Search
CPC .............................. A61N 1/025; A61N 1/0551
USPC ....................................................... 607/43, 46
See application file for complete search history.

(56) References Cited

U.S. PATENT DOCUMENTS

| | | | |
|---|---|---|---|
| 4,044,774 A | 8/1977 | Corbin et al. | |
| 4,503,863 A | 3/1985 | Katims | |
| 5,088,977 A | 2/1992 | Sibalis | |
| 5,121,754 A | 6/1992 | Mullett | |
| 5,433,739 A | 7/1995 | Sluijter et al. | |
| 5,529,574 A | 6/1996 | Frackelton | |
| 5,587,297 A | 12/1996 | Jacobson et al. | |
| 5,792,100 A | 8/1998 | Shantha | |
| 5,911,223 A | 6/1999 | Weaver et al. | |

(Continued)

FOREIGN PATENT DOCUMENTS

| | | |
|---|---|---|
| WO | 94/05369 | 3/1994 |
| WO | 01/52931 | 7/2001 |

(Continued)

OTHER PUBLICATIONS

Karran September E et201 al., 1 "The Amyloid cascade hypothesis for AD," Nature Reviews Drug Discovery, vol. 10; 698-712.

(Continued)

*Primary Examiner* — Nadia A Mahmood
(74) *Attorney, Agent, or Firm* — Sughrue Mion, PLLC

(57) ABSTRACT

Apparatus is provided that includes at least one intra-pulposus exposed electrode surface, configured to be implanted in a nucleus pulposus of an intervertebral disc, and a plurality of extra-pulposus exposed electrode surfaces, configured to be implanted outside the nucleus pulposus, in electrical communication with the intervertebral disc. Control circuitry is configured to separately control at least two of the plurality of extra-pulposus exposed electrode surfaces, and to repeatedly alternatively assume: (a) a pressure-increasing mode of operation, in which fluid is electroosmotically driven into the nucleus pulposus to increase pressure in the intervertebral disc, by applying a first mean voltage of less than 1.23 V between the exposed electrode surfaces, and (b) an oxygen-generating mode of operation, in which oxygen is generated within the nucleus pulposus by electrolysis, by applying a second mean voltage of at least 1.23 V between the exposed electrode surfaces. Other embodiments are also described.

27 Claims, 28 Drawing Sheets

(56) References Cited

U.S. PATENT DOCUMENTS

| | | |
|---|---|---|
| 5,919,163 A | 7/1999 | Glickman |
| 5,938,690 A | 8/1999 | Law et al. |
| 6,041,252 A | 3/2000 | Walker et al. |
| 6,146,380 A | 11/2000 | Racz et al. |
| 6,161,047 A | 12/2000 | King et al. |
| 6,360,750 B1 | 3/2002 | Gerber et al. |
| 6,506,408 B1 | 1/2003 | Palasis |
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |
| 6,907,295 B2 | 6/2005 | Gross et al. |
| 6,941,172 B2 | 9/2005 | Nachum |
| 6,997,941 B2 | 2/2006 | Sharkey et al. |
| 7,120,489 B2 | 10/2006 | Shalev et al. |
| 7,217,351 B2 | 5/2007 | Krumme |
| 7,223,227 B2 | 5/2007 | Pflueger |
| 7,270,659 B2 | 9/2007 | Ricart et al. |
| 7,398,121 B2 | 7/2008 | Matsumura et al. |
| 7,509,171 B2 | 3/2009 | DiMauro |
| 7,640,062 B2 | 12/2009 | Shalev |
| 7,831,306 B2 | 11/2010 | Finch et al. |
| 7,860,569 B2 | 12/2010 | Solberg et al. |
| 8,190,248 B2 | 5/2012 | Besio et al. |
| 8,457,761 B2 | 6/2013 | Wariar |
| 8,577,469 B2 | 11/2013 | Gross |
| 8,676,348 B2 | 3/2014 | Gross |
| 9,616,221 B2 | 4/2017 | Gross |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0116977 A1 | 6/2004 | Finch et al. |
| 2004/0210209 A1 | 10/2004 | Yeung et al. |
| 2004/0253304 A1 | 12/2004 | Gross et al. |
| 2004/0267240 A1 | 12/2004 | Gross et al. |
| 2005/0010205 A1 | 1/2005 | Hovda et al. |
| 2005/0021104 A1 | 1/2005 | DiLorenzo |
| 2005/0058701 A1 | 3/2005 | Gross et al. |
| 2005/0119650 A1 | 6/2005 | Sanders et al. |
| 2005/0159790 A1 | 7/2005 | Shalev |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0276844 A1 | 12/2006 | Alon et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0213700 A1 | 9/2007 | Davison et al. |
| 2008/0009927 A1 | 1/2008 | Vilims |
| 2008/0063703 A1 | 3/2008 | Gross et al. |
| 2008/0119907 A1 | 5/2008 | Stahmann |
| 2008/0188837 A1 | 8/2008 | Belsky et al. |
| 2008/0260542 A1 | 10/2008 | Nishikawa et al. |
| 2008/0275430 A1 | 11/2008 | Belsky et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0312816 A1 | 12/2009 | Gross |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0160638 A1 | 6/2011 | Mauge et al. |
| 2011/0160797 A1 | 6/2011 | Makous et al. |
| 2012/0203307 A1 | 8/2012 | Schroeppel et al. |
| 2013/0066392 A1 | 3/2013 | Simon et al. |
| 2013/0102952 A1 | 4/2013 | Gross |
| 2013/0166006 A1 | 6/2013 | Williams |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0119898 A1 | 4/2015 | Desalles et al. |
| 2017/0007823 A1 | 1/2017 | Gross |

FOREIGN PATENT DOCUMENTS

| | | |
|---|---|---|
| WO | 2001/085094 | 11/2001 |
| WO | 0185027 A2 | 11/2001 |
| WO | 2004/066903 | 8/2004 |
| WO | 2005/105053 | 11/2005 |
| WO | 2006/064502 | 6/2006 |
| WO | 2006/064503 | 6/2006 |
| WO | 2006/090397 | 8/2006 |
| WO | 2006/123346 | 11/2006 |
| WO | 2008/007369 | 1/2008 |
| WO | 2008/084477 | 7/2008 |
| WO | 2017/006327 | 1/2017 |

OTHER PUBLICATIONS

De La Torre JC, "Vascular Basis of Alzheimer's Pathogensis," Ann NY Acad Sci. 977:196-215 (Nov. 2002).

Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.

Brief PubMed search for metal ions in Alzheimers.

An Office Action dated Sep. 27, 2016, which issued during the prosecution of U.S. Appl. No. 14/926,705.

An International Search Report and a Written Opinion both dated Aug. 7, 2008, which issued during the prosecution of Applicant's PCT/IL2007/000865.

An Office Action dated Mar. 29, 2013, which issued during the prosecution of U.S. Appl. No. 12/373,306.

An Office Action dated Oct. 31, 2011, which issued during the prosecution of U.S. Appl. No. 12/373,306.

An Office Action dated Oct. 1, 2012, which issued during the prosecution of U.S. Appl. No. 12/373,306.

Notice of Allowance dated Jul. 24, 2013, which issued during the prosecution of U.S. Appl. No. 12/373,306.

An Office Action dated Apr. 11, 2013, which issued during the prosecution of U.S. Appl. No. 13/663,757.

Notice of Allowance dated Oct. 28, 2013, which issued during the prosecution of U.S. Appl. No. 13/663,757.

Elixmann IM et al., "In-vitro evaluation of a drainage catheter with integrated bioimpedance electrodes to determine ventricular size," Biomed Tech 2013; 58 (Suppl. 1) Sep. 2013 (2 pages total).

An Office Action dated Aug. 31, 2015, which issued during the prosecution of U.S. Appl. No. 13/872,794.

An Applicant Initiated Interview Summary dated Dec. 14, 2015, which issued during the prosecution of U.S. Appl. No. 13/872,794.

An Office Action dated Feb. 3, 2016, which issued during the prosecution of U.S. Appl. No. 13/872,794.

Notice of Allowance dated Dec. 9, 2016, which issued during the prosecution of U.S. Appl. No. 14/794,739.

An Applicant Initiated Interview Summary dated Feb. 25, 2016, which issued during the prosecution of U.S. Appl. No. 13/872,794.

An Office Action dated Jun. 15, 2016, which issued during the prosecution of U.S. Appl. No. 13/872,794.

An International Search Report and a Written Opinion both dated Oct. 20, 2016, which issued during the prosecution of Applicant's PCT/IL2016/050728.

U.S. Appl. No. 60/830,717, filed Jul. 12, 2006.

Vernengo J, "Injectable Bioadhesive Hydrogels for Nucleus Pulposus Replacement and Repair of the Damaged Intervertebral Disc: A Thesis," Drexel University (Jan. 2007).

Cheung KMC et al., "Intervertebral disc regeneration by use of autologous mesenchymal stem cells, an experimental model in rabbits," Abstract from the SRS 2004 Annual Meeting.

(56) References Cited

OTHER PUBLICATIONS

Freemont TJ et al., "Degeneration of intervertebral discs: current understanding of cellular and molecular events, and implications for novel therapies," Expert Reviews in Molecular Biology, Mar. 29, 2001 (Cambridge University Press).
Urban JPG et al., "The nucleus of the intervertebral disc from development to degeneration," American Zoologist 40(1): 53-61 (2000).
Restriction Requirement dated Sep. 12, 2011, which issued during the prosecution of U.S. Appl. No. 12/373,306.
An International Preliminary Report on Patentability dated Apr. 7, 2009, which issued during the prosecution of Applicant's PCT/IL2007/000865.
An International Preliminary Report on Patentability dated Dec. 22, 2009, which issued during the prosecution of Applicant's PCT/IL2008/000038.
An International Search Report and a Written Opinion both dated Sep. 2, 2008, which issued during the prosecution of Applicant's PCT/IL2008/000038.
An Office Action dated Jan. 16, 2015, which issued during the prosecution of U.S. Appl. No. 13/872,794.
Loutzenhiser, "Membrane Potential measurements in renal afferent and efferent arterioles: actions of Angiotensin II", AJP- Renal Physiol Aug. 1, 1997 vol. 273 No. 2 F307-F314.
Iatridis JC et al., "Influence of fixed charge density magnitude and distribution on the intervertebral disc: applications of a poroelastic and chemical electric (PEACE) model," J Biomech Eng. 125(1):12-24 (Feb. 2003).
"Implanting ultrathin electrodes in soft tissue," https://www.youtube.com/watch?v=FaBYQ68JIM8&spfreload=10, Published on Oct. 10, 2014 (excerpts from video).
Service RF, "Electric fields deliver drugs into tumors ,"http://news.sciencemag.org, Feb. 4, 2015.
Dao-Sheng Liu et al., "Activation of Na+ and K+ Pumping Modes of (Na,K)—ATPase by an Oscillating Electric Field," The Journal of Biological Chemistry, vol. 265. No. 13, May 5, 1990.(pp. 7260-7267).
An International Search Report and a Written Opinion both dated Jan. 26, 2017, which issued during the prosecution of Applicant's PCT/IL2016/051161.
An International Search Report and a Written Opinion both dated Mar. 10, 2017, which issued during the prosecution of Applicant's PCT/IL2016/051363.
An Office Action dated May 26, 2017, which issued during the prosecution of U.S. Appl. No. 15/453,290.
Notice of Allowance dated Jul. 24, 2017, which issued during the prosecution of U.S. Appl. No. 14/982,187.
An Invitation to Pay Additional Fees issued in counterpart International Appl. PCT/IL2017/051032, dated Dec. 12, 2017.
An ISR and Written Opinion issued in counterpart International Appl. PCT/IL2017/051032, dated Feb. 12, 2018.

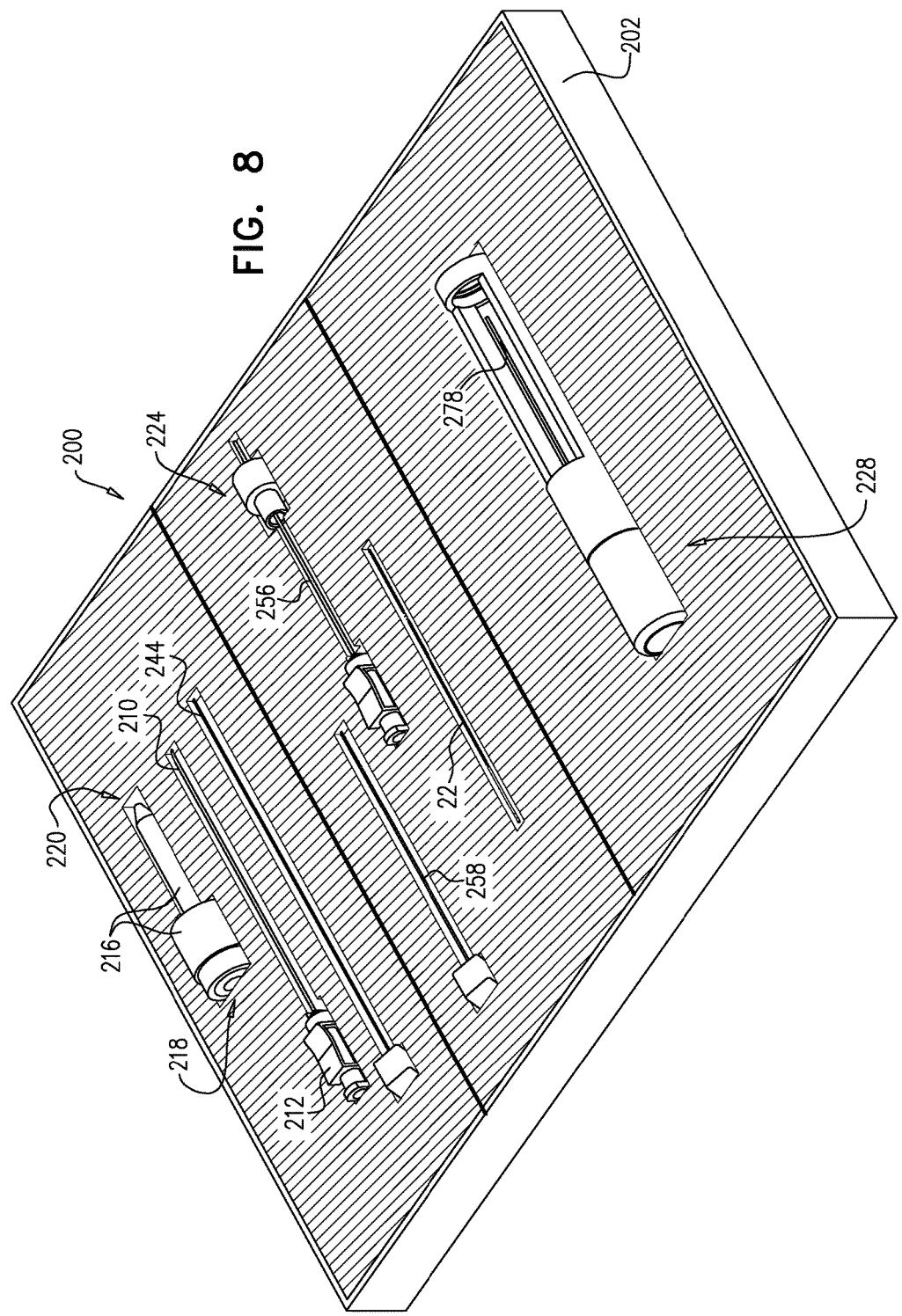

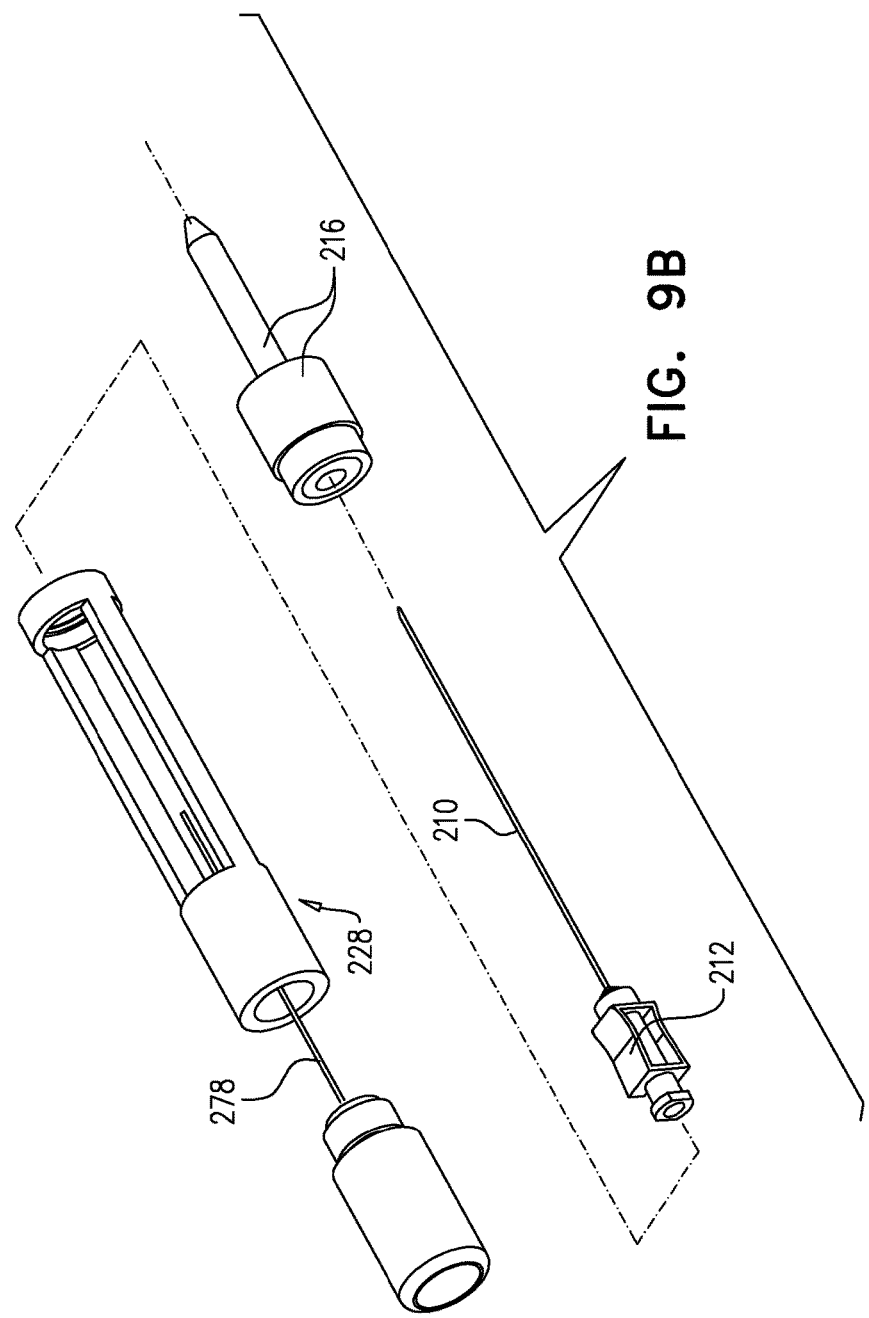

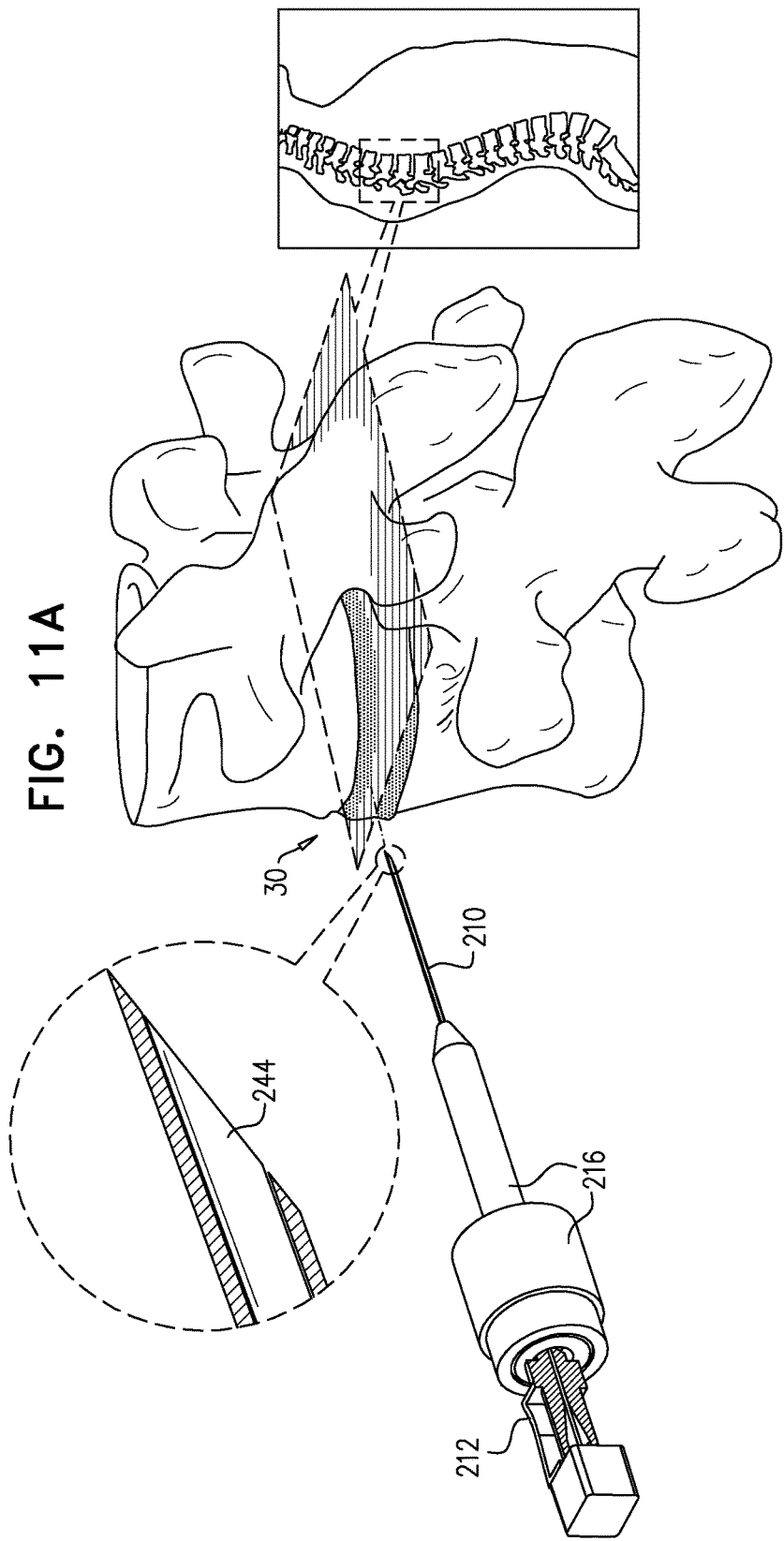

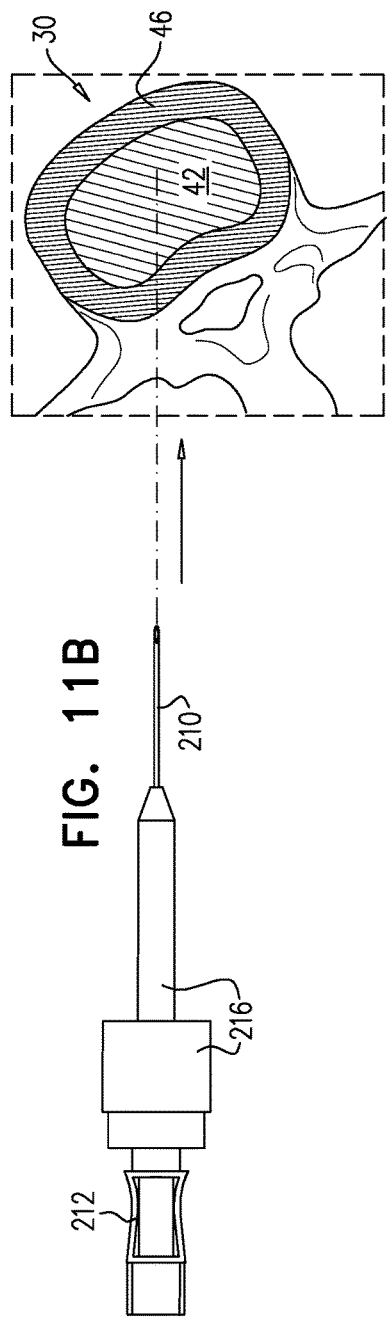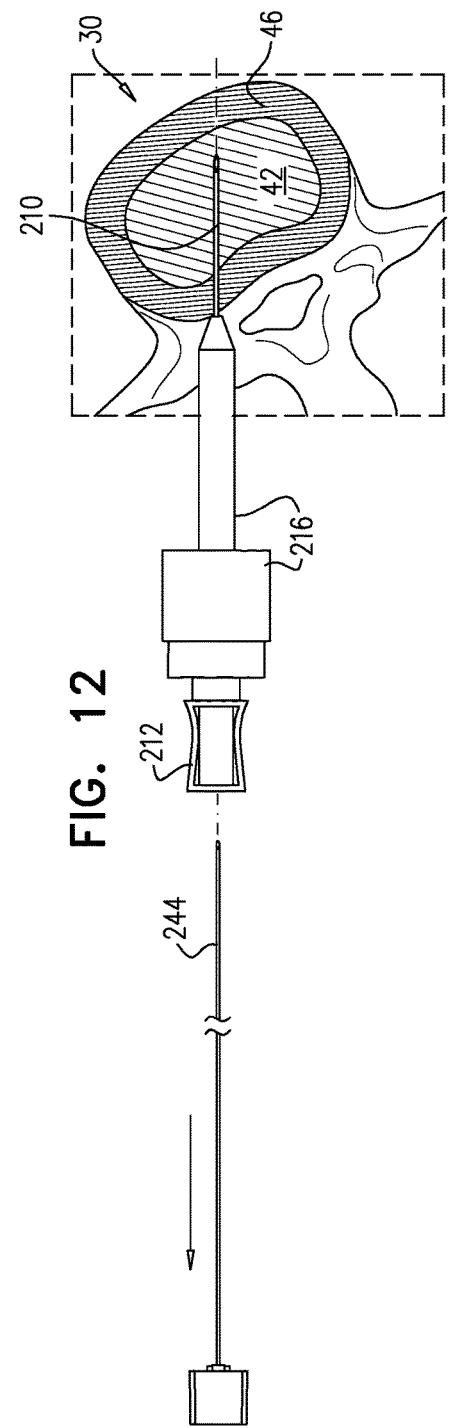

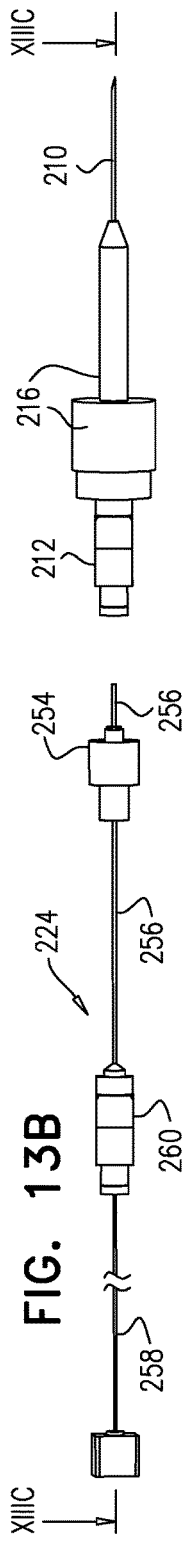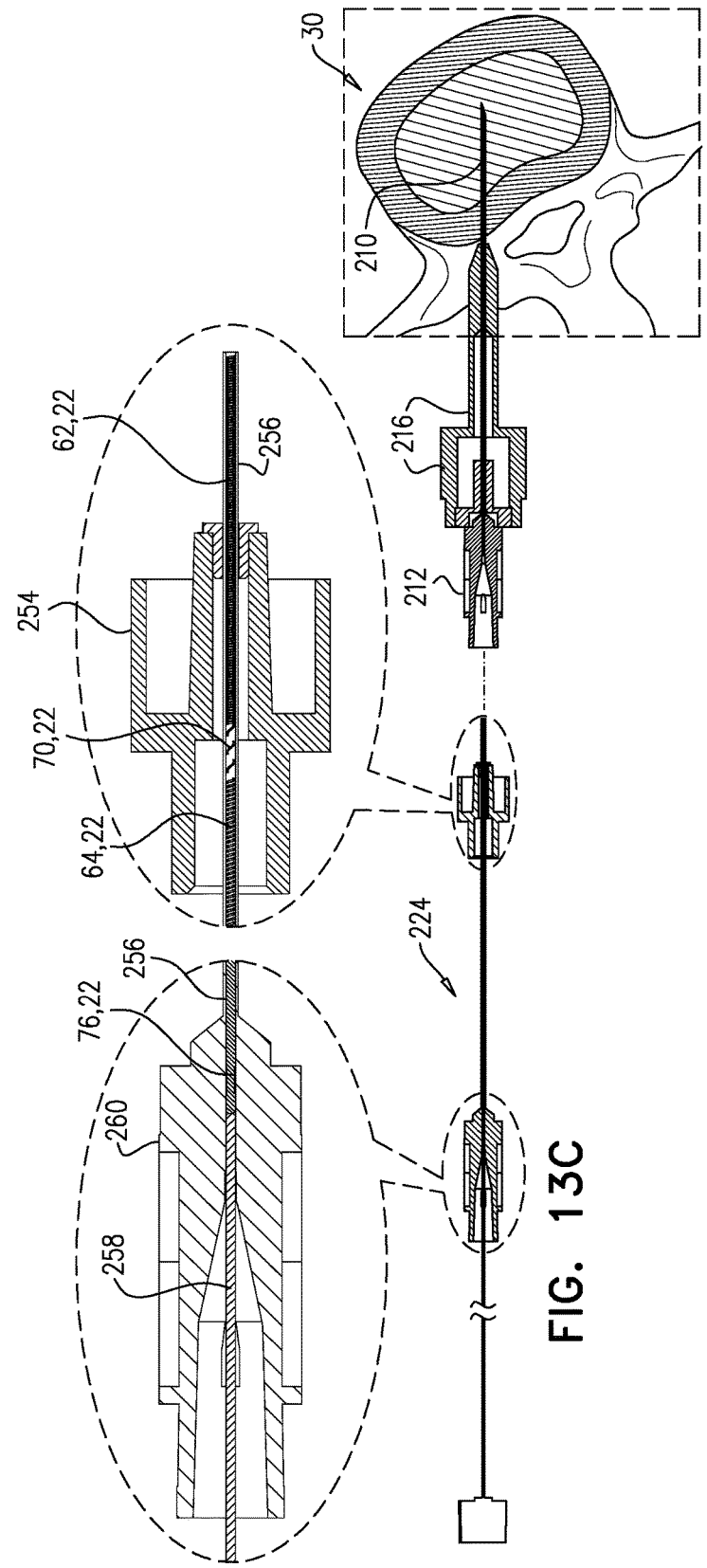
FIG. 13B
FIG. 13C

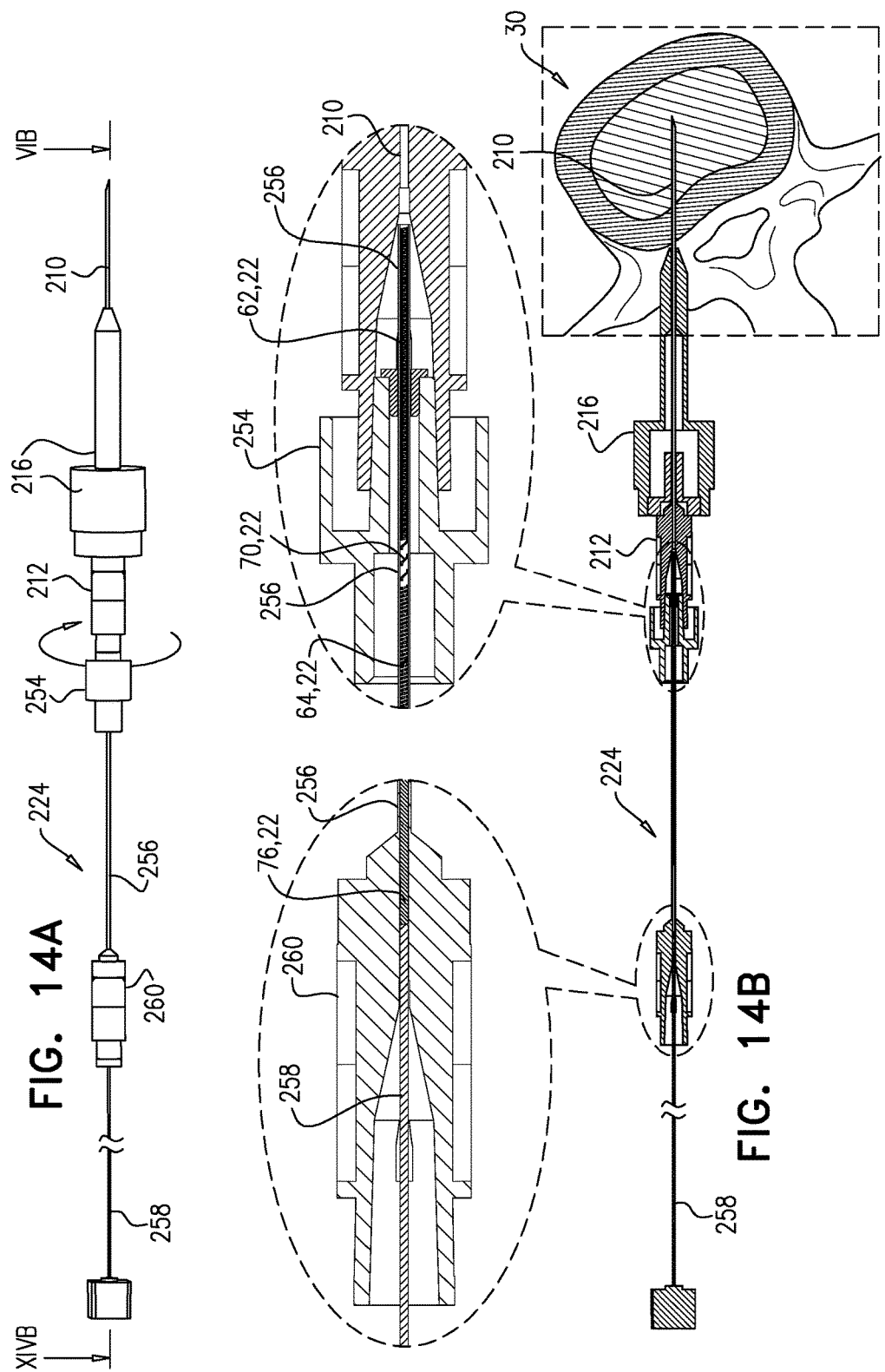

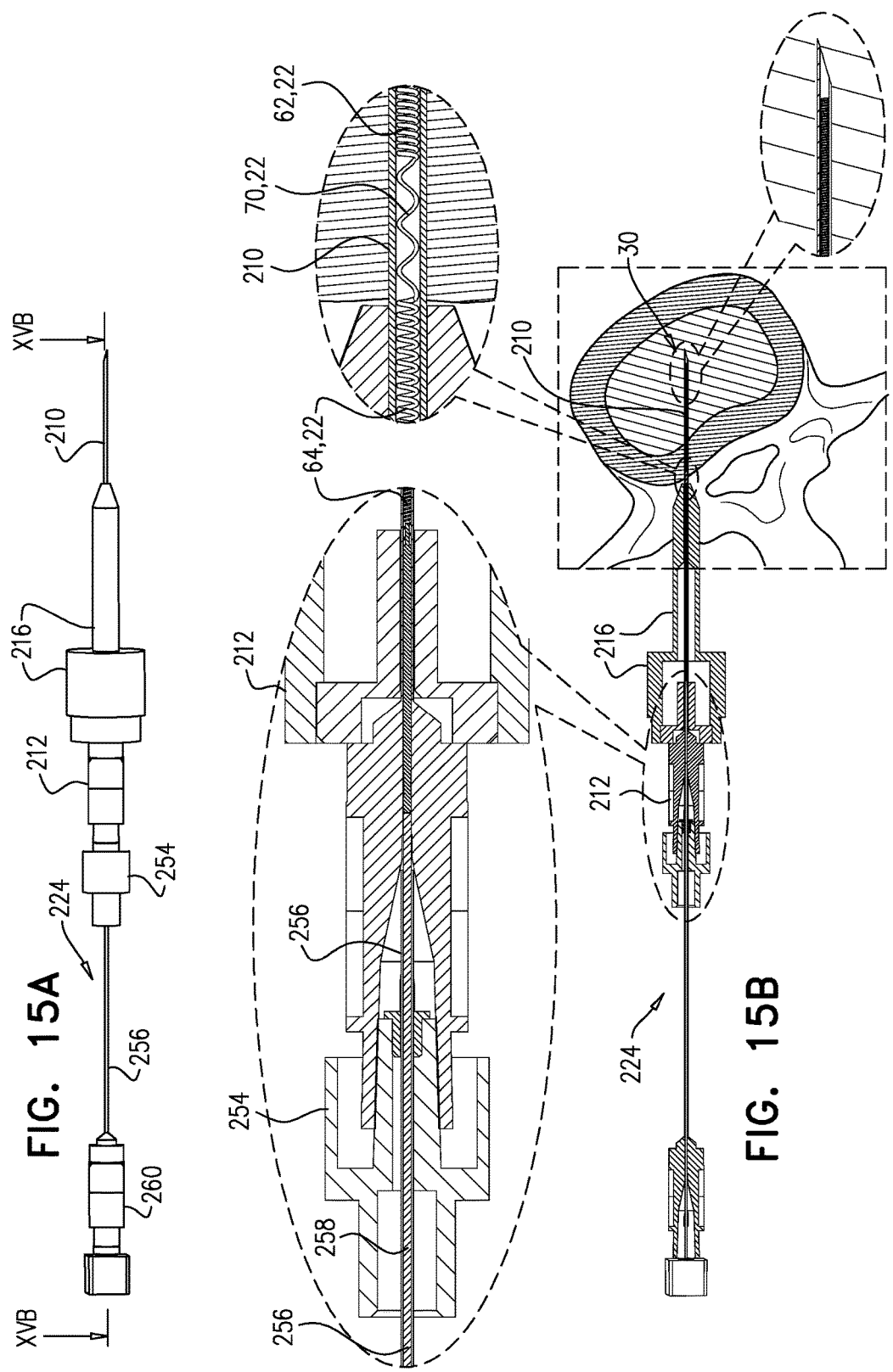

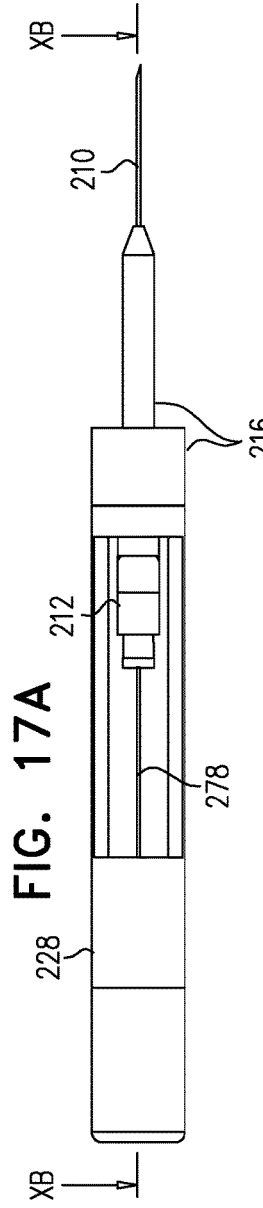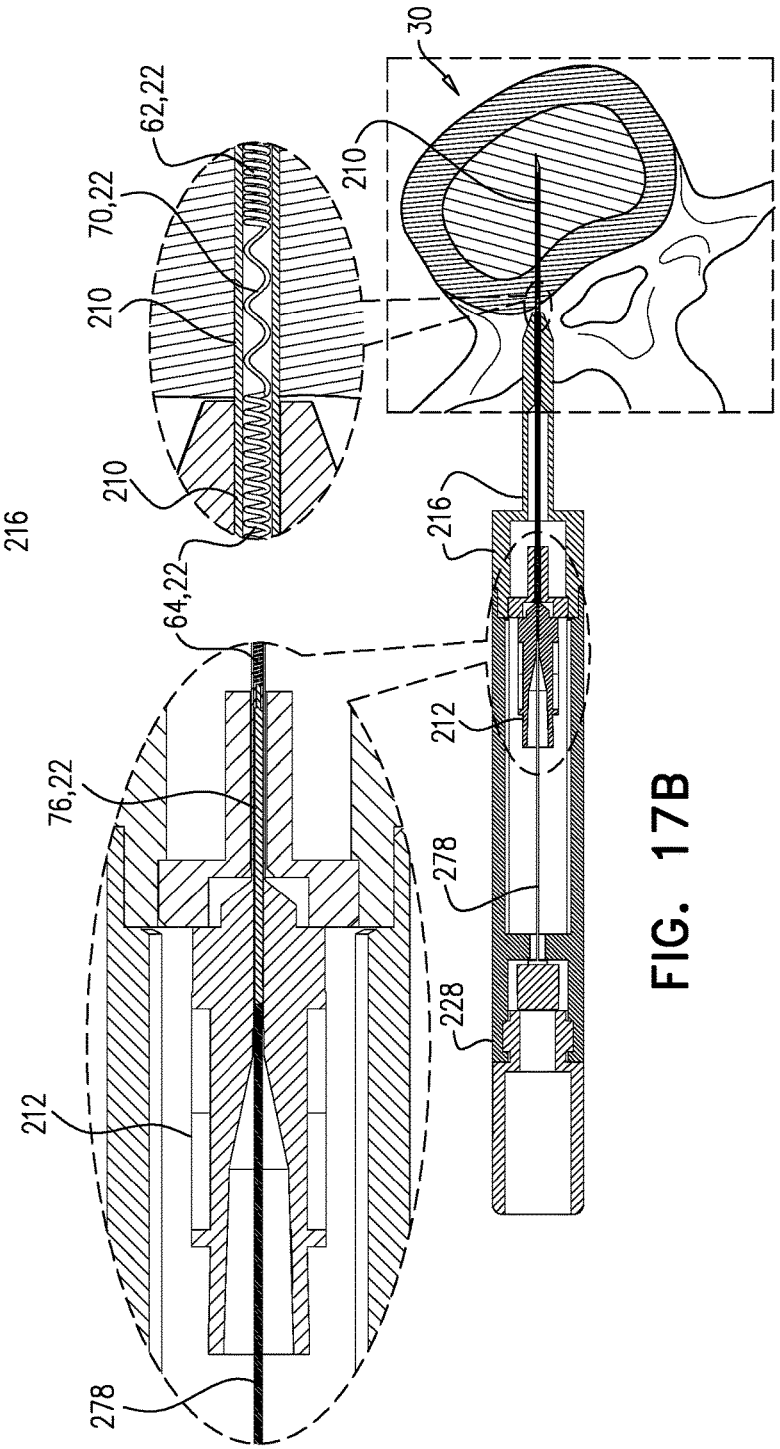
FIG. 17A
FIG. 17B

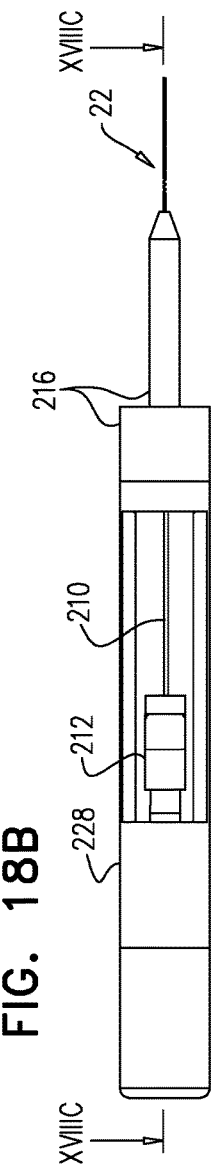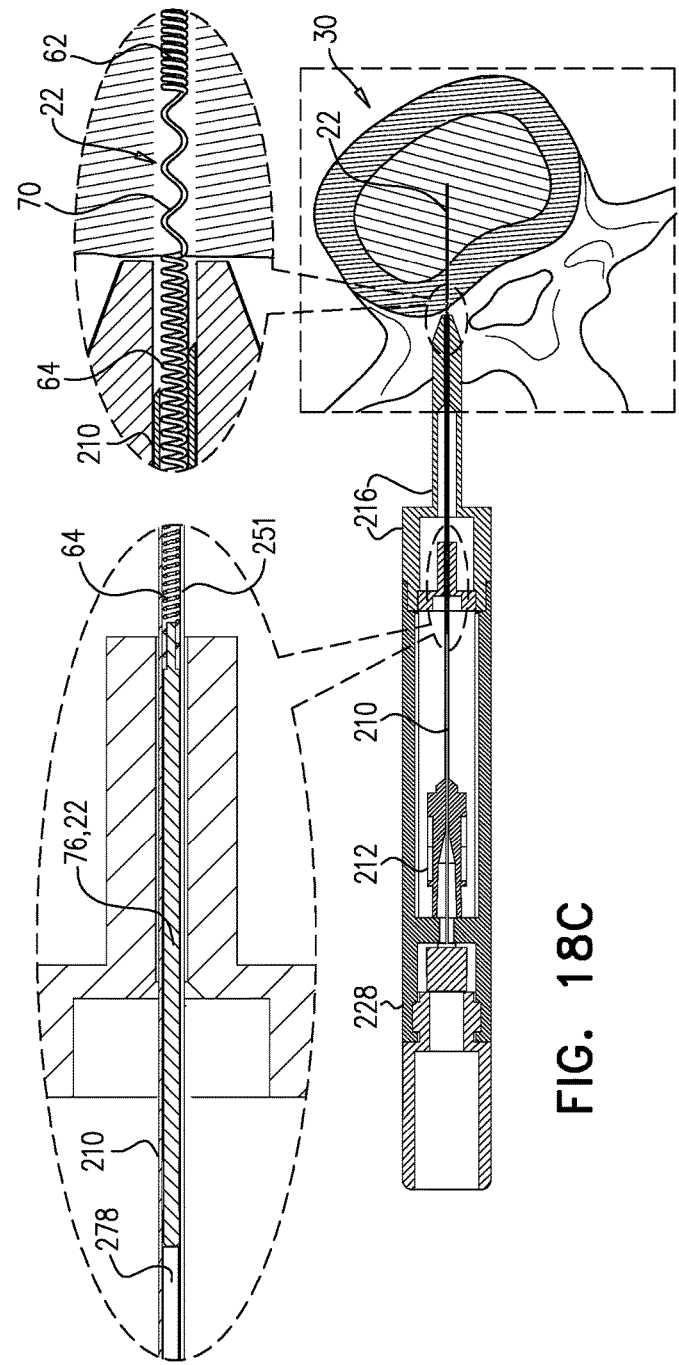
FIG. 18B
FIG. 18C

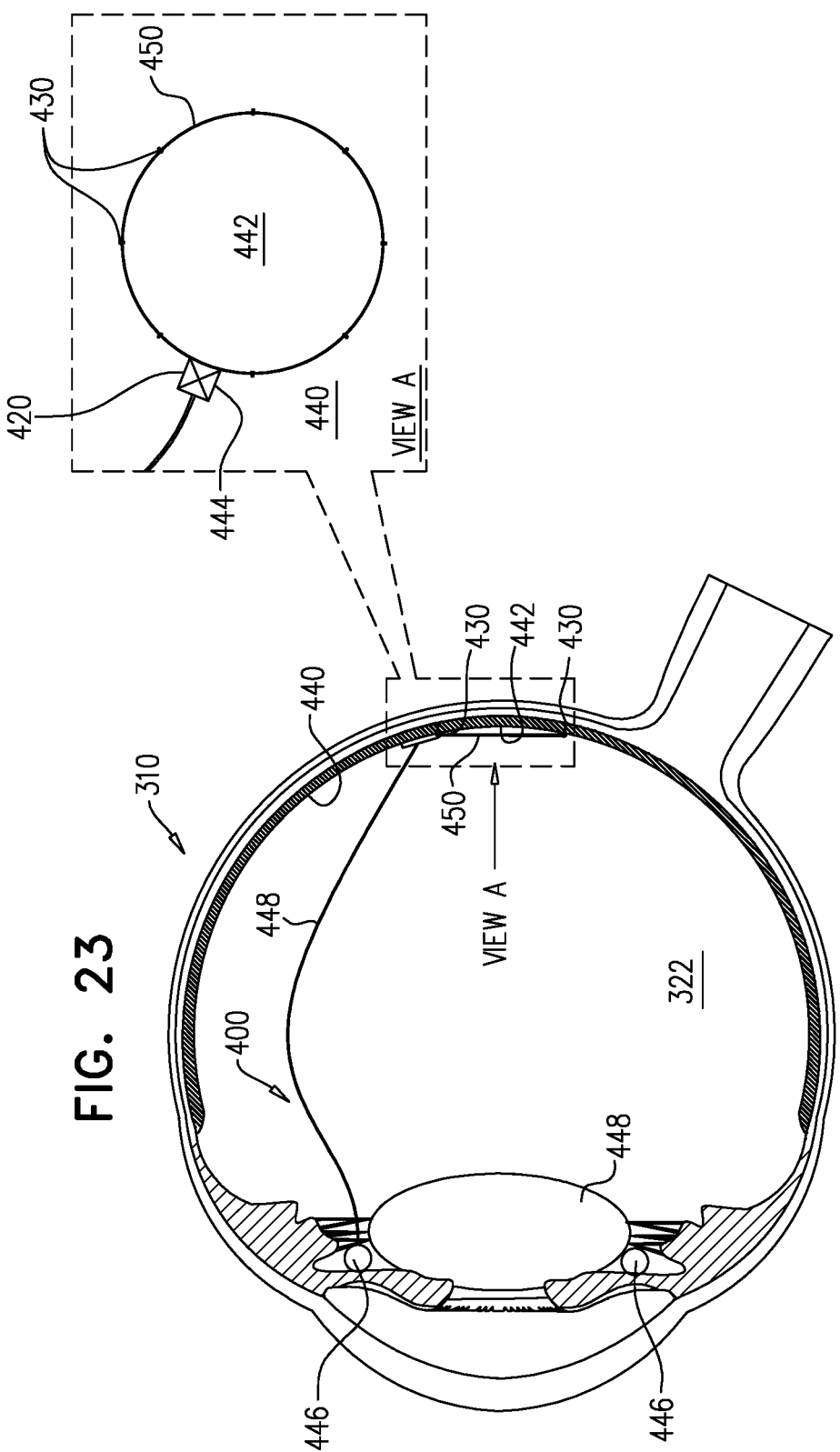

DISC THERAPY

FIELD OF THE APPLICATION

The present invention relates generally to therapeutic electrical techniques.

BACKGROUND OF THE APPLICATION

The intervertebral discs form cartilaginous joints between the end plates of vertebrae to provide shock absorption. The discs include two main regions: the nucleus pulposus, which is an inner, soft and highly hydrated structure, and the annulus fibrosus, which is a strong structure including lamellae (concentric sheets of collagen fibers), which surrounds the nucleus. The three major constituents of the discs are water, fibrillar collagens, and aggrecan. The proportion of these components varies across the disc, with the nucleus having a higher concentration of aggrecan and water and a lower collagen content than other regions of the disc. The loss of water content, particularly in the nucleus pulposus, is associated with disc degeneration, and with a decrease in disc height and abnormal loading of other spinal structures.

U.S. Pat. No. 8,577,469 to Gross, which is assigned to the assignee of the present application and is incorporated herein by reference, describes apparatus for treating an intervertebral disc of a subject. The apparatus includes a first electrode, configured to be inserted into a nucleus pulposus of the disc, and a second electrode, configured to be placed outside of the nucleus pulposus, in a vicinity of the nucleus pulposus. A control unit is configured to drive a current between the first and second electrodes, and to configure the current to electroosmotically drive fluid between inside and outside the nucleus pulposus. Other embodiments are also described US Patent Application Publication 2005/0277996 to Podhajsky describes a method for reducing intervertebral pressure, including providing an electrode, having proximal and distal ends, and a generator, which is operatively connected to the proximal end of the electrode, and is configured to supply radiofrequency current thereto. The method also includes inserting at least a portion of the distal end of the electrode into the nucleus pulposus of an intervertebral disc and activating the generator to heat the nucleus pulposus. The electrode may be inserted into the intervertebral disc through its first lateral side and/or its second lateral side, and may be substantially parallel to the major or minor axis of the nucleus pulposus.

SUMMARY OF THE APPLICATION

In some embodiments of the present invention, an intervertebral-disc-treatment system is provided for treating an intervertebral disc of a subject. The intervertebral-disc-treatment system comprises (a) an electrode, which is configured to be implanted partially within a nucleus pulposus of the disc, and (b) one or more extra-pulposus exposed electrode surfaces, which are configured to be implanted outside the nucleus pulposus, in electrical communication with the disc, in a vicinity of an external surface of an annulus fibrosus of the disc. The intervertebral-disc-treatment system further comprises implantable or external control circuitry, which is typically electrically coupled, by one or more electrode leads, to the exposed electrode surfaces and the electrode.

For some applications, the electrode comprises a wire, which typically has a wire diameter of between 50 and 150 microns, such as 100 microns. The wire includes:
- a non-electrically-insulated current-application longitudinal segment, which, in the absence of any applied forces, is helically coiled and typically has (a) a mean pitch of between 1.1 and 2 times the wire diameter, and (b) an entire longitudinal length of between 5 and 35 mm, and
- an electrically-insulated lead longitudinal segment, which typically has an entire longitudinal length of between 5 and 80 mm, in the absence of any applied forces.

For some applications, the current-application longitudinal segment has an outer coil diameter of between 3 and 7 times the wire diameter, in the absence of any applied forces.

Typically, because of the above-mentioned dimensions, including the pitch, the current-application longitudinal segment is highly flexible (both in its ability to bend and its ability to longitudinally stretch and contract), which reduces the application of forces on the intervertebral disc, and thus generally causes no or less trauma to the intervertebral disc, including the nucleus pulposus, than a more rigid electrode might cause, particularly over time during repeated motion of the disc.

For some applications, the lead longitudinal segment is coiled, in the absence of any applied forces. For some applications, the lead longitudinal segment has one or more of the following dimensions, in the absence of any applied forces: (a) a mean pitch that is greater than the mean pitch $P_1$ of the current-application longitudinal segment, (b) a mean pitch of between 2 and 3 times the wire diameter, (c) an outer coil diameter that equals between 90% and 110% of the outer coil diameter of the current-application longitudinal segment, and/or (d) an outer coil diameter of between 3 and 7 times the wire diameter. Typically, providing the above-mentioned pitches enables the thorough application of insulation to the electrically-insulated lead longitudinal segment, particularly if a vapor deposition process is used to apply the insulation (e.g., parylene). In addition, the lead longitudinal segment may have a greater pitch than the current-application longitudinal segment in part because the lead longitudinal segment generally does not require as much flexibility as the current-application longitudinal segment.

For some applications, the wire further includes an the intermediate longitudinal segment, which (a) is longitudinally between the current-application longitudinal segment and the lead longitudinal segment, (b) typically has an entire longitudinal length of between 1 and 6 mm, in the absence of any applied forces, and (c) in the absence of any applied forces, either (i) is coiled, and has a mean pitch greater than the outer coil diameter of the current-application longitudinal segment, or (ii) is not coiled. For some applications, the intermediate longitudinal segment is electrically insulated along at least a longitudinal portion of the intermediate longitudinal segment. For some applications in which the intermediate longitudinal segment is coiled, the intermediate longitudinal segment has one or more of the following dimensions, in the absence of any applied forces: (a) a mean pitch of between 125% and 250% of the outer coil diameter of the current-application longitudinal segment, (b) a mean pitch of between 5 and 20 times the wire diameter, (c) a mean pitch $P_3$ that equals (i) at least the mean pitch of the current-application longitudinal segment, and (ii) no more than the mean pitch of the lead longitudinal segment, (d) an outer coil diameter equal to between 90% and 110% of the outer coil diameter of the current-application longitudinal segment, and/or (e) an outer coil diameter of between 3 and 7 times the wire diameter.

For some applications, the wire further includes a pin-connector longitudinal segment. The lead longitudinal segment is longitudinally between the current-application longitudinal segment and the pin-connector longitudinal segment. For these applications, the intervertebral-disc-treatment system typically comprises an electrode assembly, which comprises the electrode and a pin, which is mechanically fixed to and in electrical communication with the pin-connector longitudinal segment. Typically, the area surrounding the pin and the pin-connector longitudinal segment is electrically insulated, such as by silicone.

At least a portion of the electrode is implanted in a body of a subject, typically such that:
  the current-application longitudinal segment is disposed at least partially in the intervertebral disc of the subject, typically entirely in the intervertebral disc (either entirely in the nucleus pulposus of the intervertebral disc, or partially in a nucleus pulposus of the intervertebral disc and partially in the annulus fibrosus of the intervertebral disc),
  at least a portion of the lead longitudinal segment is disposed in the body of the subject outside the intervertebral disc, and
  if provided, the intermediate longitudinal segment is disposed at least in part in the annulus fibrosus of the intervertebral disc; providing the relatively large pitch for the intermediate longitudinal segment, or not coiling the intermediate longitudinal segment, may reduce the likelihood that the portion of the intermediate longitudinal segment that is within the annulus fibrosus forms a tunnel, which might cause leakage of fluid from the nucleus pulposus.

In some applications of the present invention, a method of implanting at least a portion of an electrode in a body of a subject is provided, the method comprising:
  inserting a hollow insertion needle into an intervertebral disc of the subject;
  aligning an electrode loader with the hollow insertion needle, while the electrode is preloaded in a hollow loader needle of the electrode loader, and a loader stylet of the electrode loader is preloaded partially in the hollow loader needle and disposed such a distal end of the loader stylet abuts a proximal end of the electrode;
  connecting the electrode loader to the hollow insertion needle, such that a distal end of the hollow loader needle abuts a proximal end of the hollow insertion needle;
  advancing the electrode into the hollow insertion needle by advancing the loader stylet distally within the hollow loader needle so that the loader stylet pushes the electrode distally from the hollow loader needle into the insertion needle;
  aligning a needle-withdrawal handle and a handle stylet thereof with the hollow insertion needle;
  connecting the needle-withdrawal handle to the hollow insertion needle;
  proximally withdrawing the hollow insertion needle from the intervertebral disc, while holding the needle-withdrawal handle stationary, and while the handle stylet abuts the proximal end of the electrode, thereby preventing proximal motion of the electrode; and
  proximally withdrawing the needle-withdrawal handle, thereby releasing the electrode and leaving the electrode implanted partially in the intervertebral disc and partially in the body of the subject outside the intervertebral disc.

For some applications, inserting the hollow insertion needle comprises limiting a depth of penetration of the hollow insertion needle into the intervertebral disc by inserting the hollow insertion needle into the intervertebral disc until a spacer, through which the hollow insertion needle passes, contacts an external surface of an annulus fibrosis of the intervertebral disc. For some applications, connecting the needle-withdrawal handle to the hollow insertion needle comprises connecting the needle-withdrawal handle to the spacer. For some applications, proximally withdrawing the needle-withdrawal handle comprises proximally withdrawing the needle-withdrawal handle while the spacer is attached to the needle-withdrawal handle.

For some applications, the hollow insertion needle is axially fixed to a needle-connection fitting. Connecting the needle-withdrawal handle to the hollow insertion needle comprises disposing (a) the needle-connection fitting within the needle-withdrawal handle, and (b) a distal end of the handle stylet within the needle-connection fitting abutting the proximal end of the electrode. Proximally withdrawing the hollow insertion needle comprises proximally withdrawing the needle-connection fitting within the needle-withdrawal handle, while the needle-withdrawal handle is held stationary.

In some applications of the present invention, the intervertebral-disc-treatment system comprises:
  at least one intra-pulposus exposed electrode surface, which is configured to be implanted in the nucleus pulposus of the intervertebral disc;
  a plurality of extra-pulposus exposed electrode surfaces, which are configured to be implanted outside the nucleus pulposus, in electrical communication with the intervertebral disc; and
  the control circuitry, which is (a) electrically coupled to the at least one intra-pulposus exposed electrode surface and the plurality of the extra-pulposus exposed electrode surfaces, (b) configured to separately control at least two of the plurality of the extra-pulposus exposed electrode surfaces; for example, the control circuitry may be electrically coupled to the extra-pulposus exposed electrode surfaces separately via separate electrical conductors.

Providing the plurality of separately-controllable the extra-pulposus exposed electrode surfaces distributes the generation of hydrogen, thereby reducing any local build-up of hydrogen at any single electrode surface.

For some applications, the control circuitry is configured to:
  repeatedly assume a pressure-increasing mode of operation in alternation with an oxygen-generating mode of operation,
  in the pressure-increasing mode of operation, (a) configure the at least one intra-pulposus exposed electrode surface to be a cathode, and one or more of the plurality of the extra-pulposus exposed electrode surfaces to be one or more respective anodes, and (b) electroosmotically drive fluid into the nucleus pulposus to increase pressure in the intervertebral disc, by applying a first mean voltage of less than 1.23 V (sometimes known in the art as the "electrolysis voltage") between the at least one intra-pulposus exposed electrode surface and the one or more of the plurality of the extra-pulposus exposed electrode surfaces, and in the oxygen-generating mode of operation, (a) configure the at least one intra-pulposus exposed electrode surface to be an anode, and the plurality of the extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the plurality of the extra-pulposus exposed electrode surfaces.

The increase in fluid in the nucleus pulposus during the pressure-increasing mode of operation generally treats or prevents further degeneration of the disc caused at least in part by loss of fluid. The applied current may also help introduce nutritional substances into the disc. The generation of oxygen within the nucleus pulposus during the oxygen-generating mode generally treats hypoxia, which, if untreated, sometimes causes disc degeneration. The generation of oxygen may also improve glucose metabolism, while reducing lactic acid generation.

For some applications, the control circuitry is configured to apply direct current, e.g., with an average amplitude of between 1 and 5 mA. For some applications, the control unit is configured to apply the direct current as a series of pulses. For some applications, the control unit is configured to apply the direct current as the series of pulses with a duty cycle of between 1% and 50%.

Typically, the control circuitry is configured to separately control all of the plurality of the extra-pulposus exposed electrode surfaces; for example, the control circuitry may be electrically coupled to the extra-pulposus exposed electrode surfaces separately via separate electrical conductors.

For some applications, the control circuitry is configured, during a period of time, to assume (a) the pressure-increasing mode of operation at least 10 times for an aggregate first duration and (b) the oxygen-generating mode of operation at least 10 times for an aggregate second duration that is less than 10% of the aggregate first duration. By way of example and not limitation, the control circuitry may assume the oxygen-generating mode of operation for a few seconds every hour, and assume the pressure-increasing mode of operation at other times. Although the control circuitry, when in the oxygen-generating mode of operation, may electroosmotically drive fluid out of the nucleus pulposus and thus decrease pressure in the intervertebral disc, because the aggregate second duration is so much less than the aggregate first duration, the aggregate effect of the application of voltages is an increase in pressure in the intervertebral disc.

For some applications, the control circuitry is configured to, in the oxygen-generating mode of operation, generate oxygen within the nucleus pulposus by electrolysis, by applying the second mean voltage between the at least one intra-pulposus exposed electrode surface and respective different subsets of the plurality of the extra-pulposus exposed electrode surfaces at respective different times. For some applications, each of the subsets consists of exactly one of the plurality of the extra-pulposus exposed electrode surfaces. Activating the extra-pulposus exposed electrode surfaces at different times further distributes the generation of hydrogen, thereby further reducing any local build-up of hydrogen at any single electrode surface.

In some applications of the present invention, the intervertebral-disc-treatment system comprises:
  at least one intra-pulposus exposed electrode surface, which is configured to be implanted in the nucleus pulposus of the intervertebral disc;
  one or more the extra-pulposus exposed electrode surfaces, which (a) are configured to be implanted outside the nucleus pulposus, in electrical communication with the intervertebral disc, and (b) have an aggregate electrically-exposed surface area of at least 3 cm2, such as at least 4 cm2, e.g., at least 5 cm2; and
  the control circuitry, which is electrically coupled to the at least one intra-pulposus exposed electrode surface and one or more the extra-pulposus exposed electrode surfaces.

For some applications, the control circuitry is configured to:
  repeatedly assume a pressure-increasing mode of operation in alternation with an oxygen-generating mode of operation,
  in the pressure-increasing mode of operation, (a) configure the at least one intra-pulposus exposed electrode surface to be a cathode, and the one or more extra-pulposus exposed electrode surfaces to be one or more respective anodes, and (b) electroosmotically drive fluid into the nucleus pulposus to increase pressure in the intervertebral disc, by applying a first mean voltage of less than 1.23 V between the at least one intra-pulposus exposed electrode surface and the one or more extra-pulposus exposed electrode surfaces, and
  in the oxygen-generating mode of operation, (a) configure the at least one intra-pulposus exposed electrode surface to be an anode, and the one or more extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the one or more extra-pulposus exposed electrode surfaces.

The increase in fluid in the nucleus pulposus during the pressure-increasing mode of operation generally treats or prevents further degeneration of the disc caused at least in part by loss of fluid. The applied current may also help introduce nutritional substances into the disc. The generation of oxygen within the nucleus pulposus during the oxygen-generating mode generally treats hypoxia, which, if untreated, sometimes causes disc degeneration. The generation of oxygen may also improve glucose metabolism, while reducing lactic acid generation. Providing the relatively large aggregate electrically-exposed surface area of at least 3 cm2 distributes the generation of hydrogen, thereby reducing any local build-up of hydrogen at the electrode-tissue interface.

For some applications, the intervertebral-disc-treatment system comprises exactly one extra-pulposus exposed electrode surface having an electrically-exposed surface area of at least 3 cm2. Alternatively, an external surface of a can of the control circuitry serves as the extra-pulposus exposed electrode surface. For other applications, the intervertebral-disc-treatment system comprises a plurality of the extra-pulposus exposed electrode surfaces.

For some applications, the control circuitry is configured to apply direct current, e.g., with an average amplitude of between 1 and 5 mA. For some applications, the control unit is configured to apply the direct current as a series of pulses. For some applications, the control unit is configured to apply the direct current as the series of pulses with a duty cycle of between 1% and 50%.

For some applications, the control circuitry is configured, during a period of time, to assume (a) the pressure-increasing mode of operation at least 10 times for an aggregate first duration and (b) the oxygen-generating mode of operation at least 10 times for an aggregate second duration that is less than 10% of the aggregate first duration. By way of example and not limitation, the control circuitry may assume the oxygen-generating mode of operation for a few seconds every hour, and assume the pressure-increasing mode of operation at other times. Although the control circuitry, when in the oxygen-generating mode of operation, may electroosmotically drive fluid out of the nucleus pulposus and thus decrease pressure in the intervertebral disc, because the aggregate second duration is so much less than the aggregate first duration, the aggregate effect of the application of voltages is an increase in pressure in the intervertebral disc.

There is therefore provided, in accordance with an application of the present invention, apparatus including an electrode, which includes a wire that (a) has a wire diameter of between 75 and 125 microns and (b) includes:

a non-electrically-insulated current-application longitudinal segment, which, in the absence of any applied forces, is coiled and has (i) a mean pitch of between 1.1 and 2 times the wire diameter, and (ii) an entire longitudinal length of between 5 and 35 mm, and an electrically-insulated lead longitudinal segment, which has an entire longitudinal length of between 5 and 80 mm, in the absence of any applied forces.

For some applications, the mean pitch of the current-application longitudinal segment is between 1.2 and 1.8 times the wire diameter, in the absence of any applied forces. For some applications, the mean pitch of the current-application longitudinal segment is between 1.4 and 1.6 times the wire diameter, in the absence of any applied forces.

For some applications, the wire diameter is between 90 and 110 microns. For some applications, the wire diameter of is between 95 and 105 microns.

For some applications, the current-application longitudinal segment has an outer coil diameter of between 3 and 7 times the wire diameter, in the absence of any applied forces. For some applications, the outer coil diameter of the current-application longitudinal segment is between 4 and 6 times the wire diameter, in the absence of any applied forces.

For some applications, the current-application longitudinal segment has an outer coil diameter of between 400 and 600 microns, in the absence of any applied forces.

For some applications, the entire longitudinal length of the current-application longitudinal segment is between 10 and 25 mm, in the absence of any applied forces. For some applications, the entire longitudinal length of the electrically-insulated lead longitudinal segment is between 10 and 50 mm, in the absence of any applied forces.

For some applications, when a central longitudinal axis of a 3-mm long portion of the current-application longitudinal segment is curved in a plane only until all adjacent turns of the coiled wire of the portion touch one another, the central longitudinal axis of the portion has a radius of curvature of between 5 and 10 mm.

For some applications, the current-application longitudinal segment extends to a distal end of the wire.

For some applications, the electrically-insulated lead longitudinal segment is coated with parylene.

For some applications, the lead longitudinal segment is not coiled, in the absence of any applied forces.

For some applications, the lead longitudinal segment is coiled, in the absence of any applied forces. For some applications, the lead longitudinal segment has a mean pitch that is greater than the mean pitch of the current-application longitudinal segment, in the absence of any applied forces. For some applications, the mean pitch of the lead longitudinal segment is at least 125% of the mean pitch of the current-application longitudinal segment, in the absence of any applied forces. For some applications, the mean pitch of the lead longitudinal segment is at least 150% of the mean pitch of the current-application longitudinal segment, in the absence of any applied forces. For some applications, the lead longitudinal segment has a mean pitch of between 2 and 3 times the wire diameter, in the absence of any applied forces. For some applications, the mean pitch of the lead longitudinal segment is between 2.2 and 2.8 times the wire diameter, in the absence of any applied forces. For some applications, the mean pitch of the lead longitudinal segment is between 2.4 and 2.6 times the wire diameter, in the absence of any applied forces. For some applications, the lead longitudinal segment has an outer coil diameter that equals between 90% and 110% of an outer coil diameter of the current-application longitudinal segment, in the absence of any applied forces. For some applications, the outer coil diameter of the lead longitudinal segment equals the outer coil diameter of the current-application longitudinal segment, in the absence of any applied forces. For some applications, the lead longitudinal segment has an outer coil diameter of between 3 and 7 times the wire diameter, in the absence of any applied forces. For some applications, the outer coil diameter of the lead longitudinal segment is between 4 and 6 times the wire diameter, in the absence of any applied forces.

For some applications, the wire further includes an intermediate longitudinal segment, which (a) is longitudinally between the current-application longitudinal segment and the lead longitudinal segment, (b) has an entire longitudinal length of between 1 and 6 mm, in the absence of any applied forces, and (c) in the absence of any applied forces, either (i) is coiled, and has a mean pitch greater than an outer coil diameter of the current-application longitudinal segment or (ii) is not coiled. For some applications, the intermediate longitudinal segment is electrically insulated along at least a longitudinal portion of the intermediate longitudinal segment. For some applications, the intermediate longitudinal segment is not coiled, in the absence of any applied forces. For some applications, the entire longitudinal length of the intermediate longitudinal segment is between 2 and 4 mm, in the absence of any applied forces. For some applications, in the absence of any applied forces, the intermediate longitudinal segment is coiled, and has the mean pitch greater than the outer coil diameter of the current-application longitudinal segment. For some applications, the mean pitch of the intermediate longitudinal segment is between 125% and 250% of the outer coil diameter of the current-application longitudinal segment, in the absence of any applied forces. For some applications, an outer coil diameter of the intermediate longitudinal segment equals between 90% and 110% of the outer coil diameter of the current-application longitudinal segment, in the absence of any applied forces. For some applications, the outer coil diameter of the intermediate longitudinal segment equals the outer coil diameter of the current-application longitudinal segment, in the absence of any applied forces. For some applications, the intermediate longitudinal segment has a mean pitch of between 5 and 20 times the wire diameter, in the absence of any applied forces. For some applications, the mean pitch of the intermediate longitudinal segment is between 6 and 13 times the wire diameter, in the absence of any applied forces. For some applications, the mean pitch of the intermediate longitudinal segment is between 9 and 11 times the wire diameter, in the absence of any applied forces. For some applications, the intermediate longitudinal segment has an outer coil diameter of between 3 and 7 times the wire diameter, in the absence of any applied forces. For some applications, the outer coil diameter of the intermediate longitudinal segment is between 4 and 6 times the wire diameter, in the absence of any applied forces.

For some applications:

the wire further includes a partially non-electrically-insulated pin-connector longitudinal segment, the lead longitudinal segment is longitudinally between the current-application longitudinal segment and the pin-connector longitudinal segment, and the apparatus includes an electrode assembly, which includes the electrode and a pin, which is mechanically fixed to and in electrical communication with the pin-connector longitudinal segment.

For some applications, the pin is shaped so as to define a lumen.

For some applications, the pin-connector longitudinal segment is at least partially disposed in the lumen of the pin. For some applications, the pin is crimped on the pin-connector longitudinal segment.

For some applications, the pin-connector longitudinal segment is not coiled, in the absence of any applied forces.

For some applications, the pin-connector longitudinal segment is coaxial with a central longitudinal axis of the electrically-insulated lead longitudinal segment, in the absence of any applied forces.

For some applications, the pin-connector longitudinal segment is coiled, in the absence of any applied forces. For some applications, the pin-connector longitudinal segment has a mean pitch that equals at least 125% of an outer coil diameter of the current-application longitudinal segment, in the absence of any applied forces. For some applications, the mean pitch of the pin-connector longitudinal segment is at between 125% and 250% of the outer coil diameter of the current-application longitudinal segment, in the absence of any applied forces. For some applications, the pin-connector longitudinal segment has an outer coil diameter that equals between 90% and 110% of an outer coil diameter of the current-application longitudinal segment, in the absence of any applied forces. For some applications, the outer coil diameter of the pin-connector longitudinal segment equals the outer coil diameter of the current-application longitudinal segment, in the absence of any applied forces. For some applications, the pin-connector longitudinal segment, in the absence of any applied forces, has (a) a mean pitch of between 5 and 20 times the wire diameter, and (b) an entire longitudinal length of between 1 and 4 mm. For some applications, the mean pitch of the pin-connector longitudinal segment is between 5 and 10 times the wire diameter, in the absence of any applied forces. For some applications, the pin-connector longitudinal segment has an outer coil diameter of between 3 and 7 times the wire diameter, in the absence of any applied forces. For some applications, the outer coil diameter of the pin-connector longitudinal segment is between 4 and 6 times the wire diameter, in the absence of any applied forces.

For some applications:

the wire further includes an intermediate longitudinal segment, which (a) is longitudinally between the current-application longitudinal segment and the lead longitudinal segment, and (b) has an entire longitudinal length of between 1 and 6 mm, in the absence of any applied forces, and the electrode further includes a water-permeable element that surrounds at least a longitudinal portion of the intermediate longitudinal segment.

For some applications, the water-permeable element includes a membrane.

For some applications, the water-permeable element includes an acid selected from the group consisting of: glycolic acid and lactic acid.

For some applications, the intermediate longitudinal segment is coiled, in the absence of any applied forces. For some applications, the intermediate longitudinal segment, in the absence of any applied forces, has a mean pitch that equals (a) at least the mean pitch of the current-application longitudinal segment, and (b) no more than the mean pitch of the lead longitudinal segment.

For some applications, the apparatus further includes control circuitry, which is electrically coupled to the electrode, and which is configured to drive the electrode to apply a current.

There is further provided, in accordance with an application of the present invention, apparatus including an electrode, which includes a wire that (a) has a wire diameter of between 75 and 125 microns and (b) includes a non-electrically-insulated current-application longitudinal segment, which, in the absence of any applied forces, is coiled and has (i) a mean pitch of between 1.1 and 2 times the wire diameter, and (ii) an entire longitudinal length of between 5 and 35 mm.

There is still further provided, in accordance with an application of the present invention, apparatus including an electrode, which includes a wire that includes:

a non-electrically-insulated current-application longitudinal segment, which, in the absence of any applied forces, is coiled and has an entire longitudinal length of between 5 and 35 mm, an electrically-insulated lead longitudinal segment, which has an entire longitudinal length of between 5 and 80 mm, in the absence of any applied forces, and an intermediate longitudinal segment, which (a) is longitudinally between the current-application longitudinal segment and the lead longitudinal segment, (b) has an entire longitudinal length of between 1 and 6 mm, in the absence of any applied forces, and (c) in the absence of any applied forces, either (i) is coiled, and has a mean pitch greater than an outer coil diameter of the current-application longitudinal segment or (ii) is not coiled.

For some applications, the intermediate longitudinal segment is electrically insulated along at least a longitudinal portion of the intermediate longitudinal segment.

For some applications, the intermediate longitudinal segment is not coiled, in the absence of any applied forces.

For some applications, the wire has a wire diameter of between 75 and 125 microns.

For some applications, in the absence of any applied forces, the intermediate longitudinal segment is coiled, and has the mean pitch greater than the outer coil diameter of the current-application longitudinal segment. For some applications, the mean pitch of the intermediate longitudinal segment is between 125% and 250% of the outer coil diameter of the current-application longitudinal segment, in the absence of any applied forces. For some applications, an outer coil diameter of the intermediate longitudinal segment equals between 90% and 110% of the outer coil diameter of the current-application longitudinal segment, in the absence of any applied forces.

For some applications, in the absence of any applied forces:

the current-application longitudinal segment has a mean pitch of between 1.1 and 2 times a wire diameter of the wire, and the intermediate longitudinal segment has a mean pitch of between 5 and 20 times the wire diameter.

For some applications, the intermediate longitudinal segment has an outer coil diameter of between 3 and 7 times the wire diameter, in the absence of any applied forces.

There is additionally provided, in accordance with an application of the present invention, a method including:

providing an electrode, which includes a wire that (a) has a wire diameter of between 75 and 125 microns and (b) includes (i) a non-electrically-insulated current-application longitudinal segment, which, in the absence of any applied forces, is coiled and has (A) a mean pitch of between 1.1 and 2 times the wire diameter, and (B) an entire longitudinal length of between 5 and 35 mm, and (ii) an electrically-insulated lead longitudinal segment has an entire longitudinal length of between 5 and 80 mm, in the absence of any applied forces; and implanting at least a portion of the electrode in a body of a subject.

For some applications, implanting the at least a portion of the electrode includes implanting the at least a portion of the electrode such that:

the current-application longitudinal segment is disposed at least partially in an intervertebral disc of the subject, and at least a portion of the lead longitudinal segment is disposed in the body of the subject outside the intervertebral disc.

For some applications, implanting the at least a portion of the electrode includes implanting the at least a portion of the electrode such that the current-application longitudinal segment is disposed entirely in the intervertebral disc.

For some applications, implanting the at least a portion of the electrode includes implanting the at least a portion of the electrode such that the current-application longitudinal segment is disposed entirely in a nucleus pulposus of the intervertebral disc.

For some applications, implanting the at least a portion of the electrode includes implanting the at least a portion of the electrode such that the current-application longitudinal segment is disposed partially in a nucleus pulposus of the intervertebral disc and partially in an annulus fibrosus of the intervertebral disc.

For some applications:

the wire further includes an intermediate longitudinal segment, which (a) is longitudinally between the current-application longitudinal segment and the lead longitudinal segment, (b) has an entire longitudinal length of between 1 and 6 mm, in the absence of any applied forces, and (c) in the absence of any applied forces, either (i) is coiled, and has a mean pitch greater than an outer coil diameter of the current-application longitudinal segment or (ii) is not coiled, and implanting the at least a portion of the electrode includes implanting the at least a portion of the electrode such that the intermediate longitudinal segment is disposed at least in part in an annulus fibrosus of the intervertebral disc.

There is yet additionally provided, in accordance with an application of the present invention, a method including:

providing an electrode, which includes a wire that (a) has a wire diameter of between 75 and 125 microns and (b) includes a non-electrically-insulated current-application longitudinal segment, which, in the absence of any applied forces, is coiled and has (a) a mean pitch of between 1.1 and 2 times the wire diameter, and (b) an entire longitudinal length of between 5 and 35 mm; and implanting at least a portion of the electrode in a body of a subject.

There is also provided, in accordance with an application of the present invention, a method including:

providing an electrode, which includes a wire that includes (a) a non-electrically-insulated current-application longitudinal segment, which, in the absence of any applied forces, is coiled and has an entire longitudinal length of between 5 and 35 mm, (b) an electrically-insulated lead longitudinal segment, which has an entire longitudinal length of between 5 and 80 mm, in the absence of any applied forces, and (c) an intermediate longitudinal segment, which (i) is longitudinally between the current-application longitudinal segment and the lead longitudinal segment, (ii) has an entire longitudinal length of between 1 and 6 mm, in the absence of any applied forces, and (iii) in the absence of any applied forces, either (A) is coiled, and has a mean pitch greater than an outer coil diameter of the current-application longitudinal segment or (B) is not coiled; and implanting at least a portion of the electrode in a body of a subject.

There is further provided, in accordance with an application of the present invention, a method of manufacturing an electrode, the method including:

providing an electrode, which includes a non-electrically-insulated wire that (A) has a wire diameter of between 75 and 125 microns and (B) includes:

(a) a current-application longitudinal segment, which, in the absence of any applied forces, is coiled and has a mean pitch of between 1.1 and 2 times the wire diameter, (b) a lead longitudinal segment, and (c) an intermediate longitudinal segment, which (i) is longitudinally between the current-application longitudinal segment and the lead longitudinal segment, and (ii) in the absence of any applied forces, either (A) is coiled and has a mean pitch greater than an outer coil diameter of the current-application longitudinal segment or (B) is not coiled;

providing a polymer boot that is shaped so as to define an enclosed space with an opening having a perimeter;

masking a portion of the electrode by placing the boot on the portion of the electrode, such that (a) the current-application longitudinal segment is within the enclosed space, (b) the lead longitudinal segment is outside the boot, and (c) the intermediate longitudinal segment passes through the opening such that the perimeter of the opening forms a tight seal with at least a portion of the intermediate longitudinal segment;

placing the boot and the electrode into a vapor deposition chamber; and applying a parylene coating to the lead longitudinal segment by vapor deposition within the vapor deposition chamber.

For some applications, providing the electrode includes providing the electrode in which the current-application longitudinal segment has an entire longitudinal length of between 5 and 35 mm, in the absence of any applied forces.

For some applications, providing the electrode includes providing the electrode in which the lead longitudinal segment has an entire longitudinal length of between 5 and 80 mm, in the absence of any applied forces.

For some applications, providing the electrode includes providing the electrode in which the intermediate longitudinal segment has an entire longitudinal length of between 1 and 6 mm, in the absence of any applied forces.

For some applications, providing the electrode includes providing the electrode in which, in the absence of any applied forces:

the current-application longitudinal segment has an entire longitudinal length of between 5 and 35 mm, the lead longitudinal segment has an entire longitudinal length of between 5 and 80 mm, and the intermediate longitudinal segment has an entire longitudinal length of between 1 and 6 mm.

For some applications, providing the polymer boot includes providing a silicone boot.

There is still further provided, in accordance with an application of the present invention, apparatus including an electrode and an implantation system for implanting at least a portion of the electrode in a body of a subject, the implantation system including:

a hollow insertion needle configured to be inserted into an intervertebral disc of the subject;

an electrode loader, which (a) includes (i) a hollow loader needle in which the electrode is configured to be loaded, and (ii) a loader stylet, which is configured to be loaded partially in the hollow loader needle and to be disposed such that a distal end of the loader stylet abuts a proximal end of the electrode, and (b) is configured to be connected to the hollow insertion needle, such that (i) a distal end of the hollow loader needle abuts a proximal end of the hollow insertion needle, and (ii) the loader stylet pushes the electrode distally from the hollow loader needle into the insertion needle when the loader stylet is distally advanced within the hollow loader needle; and a needle-withdrawal handle, which (a) includes a handle stylet, and (b) is configured (i) to be connected to the hollow insertion needle, (ii) while held stationary, to proximally withdraw the hollow insertion needle from the intervertebral disc while the handle stylet abuts the proximal end of the electrode, thereby preventing proximal motion of the electrode, and (iii) by being proximally withdrawn, to release the electrode and leave the electrode implanted partially in the intervertebral disc and partially in the body of the subject outside the intervertebral disc.

For some applications, the implantation system further includes a spacer, which is configured to contact an external surface of an annulus fibrosis of the intervertebral disc so as to limit a depth of penetration of the hollow insertion needle into the intervertebral disc, and the hollow insertion needle passes through the spacer.

For some applications, the needle-withdrawal handle is configured to be connected to the hollow insertion needle by connecting the needle-withdrawal handle to the spacer.

For some applications, the needle-withdrawal handle is configured to be proximally withdrawn by proximally withdrawing the needle-withdrawal handle while the spacer is attached to the needle-withdrawal handle.

For some applications:

the implantation system further includes a needle-connection fitting, which is axially fixed to the hollow insertion needle, the needle-withdrawal handle is configured such that when the needle-withdrawal handle is connected to the hollow insertion needle, the needle-connection fitting is disposed within the needle-withdrawal handle, and a distal end of the handle stylet is disposed within the needle-connection fitting abutting the proximal end of the electrode, and the needle-connection fitting is configured to be proximally withdrawn within the needle-withdrawal handle, while the needle-withdrawal handle is held stationary, so as to proximally withdraw the hollow insertion needle.

There is additionally provided, in accordance with an application of the present invention, a method of implanting at least a portion of an electrode in a body of a subject, the method including:

inserting a hollow insertion needle into an intervertebral disc of the subject;

aligning an electrode loader with the hollow insertion needle, while (a) the electrode is preloaded in a hollow loader needle of the electrode loader, and (b) a loader stylet of the electrode loader is preloaded partially in the hollow loader needle and disposed such that a distal end of the loader stylet abuts a proximal end of the electrode;

connecting the electrode loader to the hollow insertion needle, such that a distal end of the hollow loader needle abuts a proximal end of the hollow insertion needle;

advancing the electrode into the hollow insertion needle by advancing the loader stylet distally within the hollow loader needle so that the loader stylet pushes the electrode distally from the hollow loader needle into the insertion needle;

aligning a needle-withdrawal handle and a handle stylet of the needle-withdrawal handle with the hollow insertion needle;

connecting the needle-withdrawal handle to the hollow insertion needle;

proximally withdrawing the hollow insertion needle from the intervertebral disc, while holding the needle-withdrawal handle stationary, and while the handle stylet abuts the proximal end of the electrode so as to prevent proximal motion of the electrode; and proximally withdrawing the needle-withdrawal handle, thereby releasing the electrode and leaving the electrode implanted partially in the intervertebral disc and partially in the body of the subject outside the intervertebral disc.

For some applications, inserting the hollow insertion needle includes limiting a depth of penetration of the hollow insertion needle into the intervertebral disc by inserting the hollow insertion needle into the intervertebral disc until a spacer, through which the hollow insertion needle passes, contacts an external surface of an annulus fibrosis of the intervertebral disc.

For some applications, connecting the needle-withdrawal handle to the hollow insertion needle includes connecting the needle-withdrawal handle to the spacer.

For some applications, proximally withdrawing the needle-withdrawal handle includes proximally withdrawing the needle-withdrawal handle while the spacer is attached to the needle-withdrawal handle.

For some applications:

the hollow insertion needle is axially fixed to a needle-connection fitting, connecting the needle-withdrawal handle to the hollow insertion needle includes disposing (a) the needle-connection fitting within the needle-withdrawal handle, and (b) a distal end of the handle stylet within the needle-connection fitting abutting the proximal end of the electrode, and proximally withdrawing the hollow insertion needle includes proximally withdrawing the needle-connection fitting within the needle-withdrawal handle, while the needle-withdrawal handle is held stationary.

There is yet additionally provided, in accordance with an application of the present invention, apparatus for treating an intervertebral disc of a subject, the apparatus including:

at least one intra-pulposus exposed electrode surface, which is configured to be implanted in a nucleus pulposus of the intervertebral disc;

a plurality of extra-pulposus exposed electrode surfaces, which are configured to be implanted outside the nucleus pulposus, in electrical communication with the intervertebral disc; and control circuitry, which is (a) electrically coupled to the at least one intra-pulposus exposed electrode surface and the plurality of extra-pulposus exposed electrode surfaces, (b) configured to separately control at least two of the plurality of extra-pulposus exposed electrode surfaces, and (c) configured to:

repeatedly assume a pressure-increasing mode of operation in alternation with an oxygen-generating mode of operation, in the pressure-increasing mode of operation, (a) configure the at least one intra-pulposus exposed electrode surface to be a cathode, and one or more of the plurality of extra-pulposus exposed electrode surfaces to be one or more respective anodes, and (b) electroosmotically drive fluid into the nucleus pulposus to increase pressure in the intervertebral disc, by applying a first mean voltage of less than 1.23 V between the at least one intra-pulposus exposed electrode surface and the one or more of the plurality of extra-pulposus exposed electrode surfaces, and in the oxygen-generating mode of operation, (a) configure the at least one intra-pulposus exposed electrode surface to be an anode, and the plurality of extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the plurality of extra-pulposus exposed electrode surfaces.

For some applications, the control circuitry is configured to separately control all of the plurality of extra-pulposus exposed electrode surfaces.

For some applications, the first mean voltage is less than 500 mV. For some applications, the first mean voltage is less than 300 mV.

For some applications, the second mean voltage is at least 2 V.

For some applications, the control circuitry is configured, during a period of time, to assume (a) the pressure-increasing mode of operation at least 10 times for an aggregate first duration and (b) the oxygen-generating mode of operation at least 10 times for an aggregate second duration that is less than 10% of the aggregate first duration. For some applications, the aggregate second duration is less than 5% of the aggregate first duration. For some applications, the aggregate second duration is less than 1% of the aggregate first duration.

For some applications, the plurality of extra-pulposus exposed electrode surfaces includes at least three extra-pulposus exposed electrode surfaces.

For some applications, the plurality of extra-pulposus exposed electrode surfaces includes up to 10 extra-pulposus exposed electrode surfaces.

For some applications, the control circuitry is configured to, in the oxygen-generating mode of operation, generate oxygen within the nucleus pulposus by electrolysis, by applying the second mean voltage between the at least one intra-pulposus exposed electrode surface and respective different subsets of the plurality of extra-pulposus exposed electrode surfaces at respective different times.

For some applications, each of the subsets consists of exactly one of the plurality of extra-pulposus exposed electrode surfaces.

For some applications, the apparatus further includes a sensor, which is configured to sense a parameter indicative of a quantity of the oxygen generated by the electrolysis, and the control circuitry is configured to modulate the oxygen-generating mode of operation responsively to the sensed parameter. For some applications, the control circuitry is configured to modulate the oxygen-generating mode of operation by modulating a duration of one or more occurrences of the oxygen-generating mode of operation. For some applications, the control circuitry is configured to modulate the oxygen-generating mode of operation by modulating an electrical parameter of the second mean voltage. For some applications, the sensed parameter is an oxygen concentration in the nucleus pulposus. For some applications, the sensed parameter is a pH in the nucleus pulposus.

There is also provided, in accordance with an application of the present invention, apparatus for treating an intervertebral disc of a subject, the apparatus including:

at least one intra-pulposus exposed electrode surface, which is configured to be implanted in a nucleus pulposus of the intervertebral disc;

one or more extra-pulposus exposed electrode surfaces, which (a) are configured to be implanted outside the nucleus pulposus, in electrical communication with the intervertebral disc, and (b) have an aggregate electrically-exposed surface area of at least 1 cm2; and control circuitry, which is (a) electrically coupled to the at least one intra-pulposus exposed electrode surface and one or more extra-pulposus exposed electrode surfaces, and (b) configured to:

repeatedly assume a pressure-increasing mode of operation in alternation with an oxygen-generating mode of operation, in the pressure-increasing mode of operation, (a) configure the at least one intra-pulposus exposed electrode surface to be a cathode, and the one or more extra-pulposus exposed electrode surfaces to be one or more respective anodes, and (b) electroosmotically drive fluid into the nucleus pulposus to increase pressure in the intervertebral disc, by applying a first mean voltage of less than 1.23 V between the at least one intra-pulposus exposed electrode surface and the one or more extra-pulposus exposed electrode surfaces, and in the oxygen-generating mode of operation, (a) configure the at least one intra-pulposus exposed electrode surface to be an anode, and the one or more extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the one or more extra-pulposus exposed electrode surfaces.

For some applications, the aggregate electrically-exposed surface area is at least 3 cm2.

For some applications, the first mean voltage is less than 500 mV. For some applications, the first mean voltage is less than 300 mV.

For some applications, the second mean voltage is at least 2 V.

For some applications, the control circuitry is configured, during a period of time, to assume (a) the pressure-increasing mode of operation at least 10 times for an aggregate first duration and (b) the oxygen-generating mode of operation at least 10 times for an aggregate second duration that is less than 10% of the aggregate first duration. For some applications, the aggregate second duration is less than 5% of the aggregate first duration. For some applications, the aggregate second duration is less than 1% of the aggregate first duration.

For some applications, the apparatus includes exactly one extra-pulposus exposed electrode surface having an electrically-exposed surface area of at least 1 cm2. For some applications, the surface area of the of the exactly one extra-pulposus exposed electrode surface is at least 3 cm2.

For some applications, the apparatus includes a plurality of extra-pulposus exposed electrode surfaces.

For some applications, the apparatus further includes a sensor, which is configured to sense a parameter indicative of a quantity of the oxygen generated by the electrolysis, and the control circuitry is configured to modulate the oxygen-generating mode of operation responsively to the sensed parameter. For some applications, the control circuitry is configured to modulate the oxygen-generating mode of operation by modulating a duration of one or more occurrences of the oxygen-generating mode of operation. For some applications, the control circuitry is configured to modulate the oxygen-generating mode of operation by modulating an electrical parameter of the second mean voltage. For some applications, the sensed parameter is an oxygen concentration in the nucleus pulposus. For some applications, the sensed parameter is a pH in the nucleus pulposus.

There is further provided, in accordance with an application of the present invention, a method for treating an intervertebral disc of a subject, the method including:
    implanting at least one intra-pulposus exposed electrode surface in a nucleus pulposus of the intervertebral disc;
    implanting a plurality of extra-pulposus exposed electrode surfaces outside the nucleus pulposus, in electrical communication with the intervertebral disc; and
    activating control circuitry, which is (a) electrically coupled to the at least one intra-pulposus exposed electrode surface and the plurality of extra-pulposus exposed electrode surfaces, and (b) configured to separately control at least two of the plurality of extra-pulposus exposed electrode surfaces, to:
        repeatedly assume a pressure-increasing mode of operation in alternation with an oxygen-generating mode of operation,
        in the pressure-increasing mode of operation, (a) configure the at least one intra-pulposus exposed electrode surface to be a cathode, and one or more of the plurality of extra-pulposus exposed electrode surfaces to be one or more respective anodes, and (b) electroosmotically drive fluid into the nucleus pulposus to increase pressure in the intervertebral disc, by applying a first mean voltage of less than 1.23 V between the at least one intra-pulposus exposed electrode surface and the one or more of the plurality of extra-pulposus exposed electrode surfaces, and
        in the oxygen-generating mode of operation, (a) configure the at least one intra-pulposus exposed electrode surface to be an anode, and the plurality of extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the plurality of extra-pulposus exposed electrode surfaces.

There is still further provided, in accordance with an application of the present invention, a method for treating an intervertebral disc of a subject, the method including:
    implanting at least one intra-pulposus exposed electrode surface in a nucleus pulposus of the intervertebral disc;
    implanting one or more extra-pulposus exposed electrode surfaces outside the nucleus pulposus, in electrical communication with the intervertebral disc, the one or more extra-pulposus exposed electrode surfaces having an aggregate electrically-exposed surface area of at least 1 cm2; and
    activating control circuitry, which is electrically coupled to the at least one intra-pulposus exposed electrode surface and one or more extra-pulposus exposed electrode surfaces, to:
        repeatedly assume a pressure-increasing mode of operation in alternation with an oxygen-generating mode of operation,
        in the pressure-increasing mode of operation, (a) configure the at least one intra-pulposus exposed electrode surface to be a cathode, and the one or more extra-pulposus exposed electrode surfaces to be one or more respective anodes, and (b) electroosmotically drive fluid into the nucleus pulposus to increase pressure in the intervertebral disc, by applying a first mean voltage of less than 1.23 V between the at least one intra-pulposus exposed electrode surface and the one or more extra-pulposus exposed electrode surfaces, and
        in the oxygen-generating mode of operation, (a) configure the at least one intra-pulposus exposed electrode surface to be an anode, and the one or more extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the one or more extra-pulposus exposed electrode surfaces.

There is additionally provided, in accordance with an application of the present invention, apparatus for treating an eye of a subject, the apparatus including:
    a first exposed electrode surface, which is configured to be implanted in a vitreous cavity of the eye;
    a second exposed electrode surface, which is configured to be implanted in a body of the subject at a site outside the vitreous cavity; and
    control circuitry, which is configured to:
    repeatedly assume a pressure-decreasing mode of operation in alternation with an oxygen-generating mode of operation,
    in both the pressure-decreasing mode of operation and the oxygen-generating mode of operation, configure the first exposed electrode surface to be an anode, and the second exposed electrode surface to be a cathode,
    in the pressure-decreasing mode of operation, electroosmotically drive fluid from the vitreous cavity to outside the vitreous cavity to decrease pressure in the vitreous cavity, by applying a first mean voltage of less than 1.23 V between the first and the second exposed electrode surfaces, and
    in the oxygen-generating mode of operation, generate oxygen within the vitreous cavity by electrolysis, by applying a second mean voltage of at least 1.23 V between the first and the second exposed electrode surfaces.

For some applications:
    the site is within a Schlemm's canal of the subject, and the second exposed electrode surface is configured to be implanted within the Schlemm's canal, and
    the control circuitry is configured to, in the pressure-decreasing mode of operation, electroosmotically drive the fluid from the vitreous cavity to the Schlemm's canal to decrease the pressure in the vitreous cavity, by applying the first mean voltage between the first and the second exposed electrode surfaces.

For some applications, the first mean voltage is less than 500 mV. For some applications, the first mean voltage is less than 300 mV.

For some applications, the second mean voltage is at least 2 V.

For some applications, the control circuitry is configured, during a period of time, to assume (a) the pressure-decreasing mode of operation at least 10 times for an aggregate first duration and (b) the oxygen-generating mode of operation at least 10 times for an aggregate second duration that is less than 10% of the aggregate first duration. For some applications, the aggregate second duration is less than 5% of the aggregate first duration. For some applications, the aggregate second duration is less than 1% of the aggregate first duration.

For some applications, the apparatus further includes a sensor, which is configured to sense a parameter indicative of a quantity of the oxygen generated by the electrolysis, and the control circuitry is configured to modulate the oxygen-generating mode of operation responsively to the sensed parameter. For some applications, the control circuitry is configured to modulate the oxygen-generating mode of operation by modulating a duration of one or more occurrences of the oxygen-generating mode of operation. For some applications, the control circuitry is configured to modulate the oxygen-generating mode of operation by modulating an electrical parameter of the second mean voltage. For some applications, the sensed parameter is an oxygen concentration in the vitreous cavity. For some applications, the sensed parameter is a pH in the vitreous cavity.

For some applications, the control circuitry is configured to detect a pressure difference between the vitreous cavity and outside the vitreous cavity, and modulate the pressure-decreasing mode of operation responsively to the pressure difference parameter in response to the detected pressure difference.

There is yet additionally provided, in accordance with an application of the present invention, a method for treating an eye of a subject, the method including:

implanting a first exposed electrode surface in a vitreous cavity of the eye;

implanting a second exposed electrode surface in a body of the subject at a site outside the vitreous cavity; and activating control circuitry to:
repeatedly assume a pressure-decreasing mode of operation in alternation with an oxygen-generating mode of operation,
in both the pressure-decreasing mode of operation and the oxygen-generating mode of operation, configure the first exposed electrode surface to be an anode, and the second exposed electrode surface to be a cathode,
in the pressure-decreasing mode of operation, electroosmotically drive fluid from the vitreous cavity to outside the vitreous cavity to decrease pressure in the vitreous cavity, by applying a first mean voltage of less than 1.23 V between the first and the second exposed electrode surfaces, and
in the oxygen-generating mode of operation, generate oxygen within the vitreous cavity by electrolysis, by applying a second mean voltage of at least 1.23 V between the first and the second exposed electrode surfaces.

For some applications:
the site is within a Schlemm's canal of the subject, and implanting the second exposed electrode surface includes implanting the second exposed electrode surface within the Schlemm's canal, and
activating the control circuitry includes activating the control circuitry to, in the pressure-decreasing mode of operation, electroosmotically drive the fluid from the vitreous cavity to the Schlemm's canal to decrease the pressure in the vitreous cavity, by applying the first mean voltage between the first and the second exposed electrode surfaces.

The present invention will be more fully understood from the following detailed description of embodiments thereof, taken together with the drawings, in which:

BRIEF DESCRIPTION OF THE DRAWINGS

FIG. 8 is schematic illustrations of an implantation system for implanting at least a portion of the electrode of FIG. 2 in a body of a subject, in accordance with an application of the present invention;

FIGS. 9A-B are schematic illustrations of several components of the implantation system of FIG. 8, in accordance with an application of the present invention;

FIGS. 11A-B are schematic illustrations of a needle insertion step of the implantation method of FIG. 10, in accordance with an application of the present invention;

FIG. 12 is a schematic illustration of an anti-coring stylet retraction step of the implantation method of FIG. 10, in accordance with an application of the present invention;

FIGS. 13A-C are schematic illustrations of an electrode loader alignment step of the implantation method of FIG. 10, in accordance with an application of the present invention;

FIGS. 14A-B are schematic illustrations of an electrode-loader connection step of the implantation method of FIG. 10, in accordance with an application of the present invention;

FIGS. 15A-B are schematic illustrations of an electrode advancement step of the implantation method of FIG. 10, in accordance with an application of the present invention;

FIGS. 17A-B are schematic illustrations of a needle-withdrawal-handle connection step of the implantation method of FIG. 10, in accordance with an application of the present invention;

FIGS. 18A-C are schematic illustrations of an insertion-needle withdrawal step of the implantation method of FIG. 10, in accordance with an application of the present invention;

FIG. 23 is a schematic illustration of a diabetic-retinopathy-treatment system for treating diabetic retinopathy, in accordance with an application of the present invention.

DETAILED DESCRIPTION OF APPLICATIONS

Figure 1:
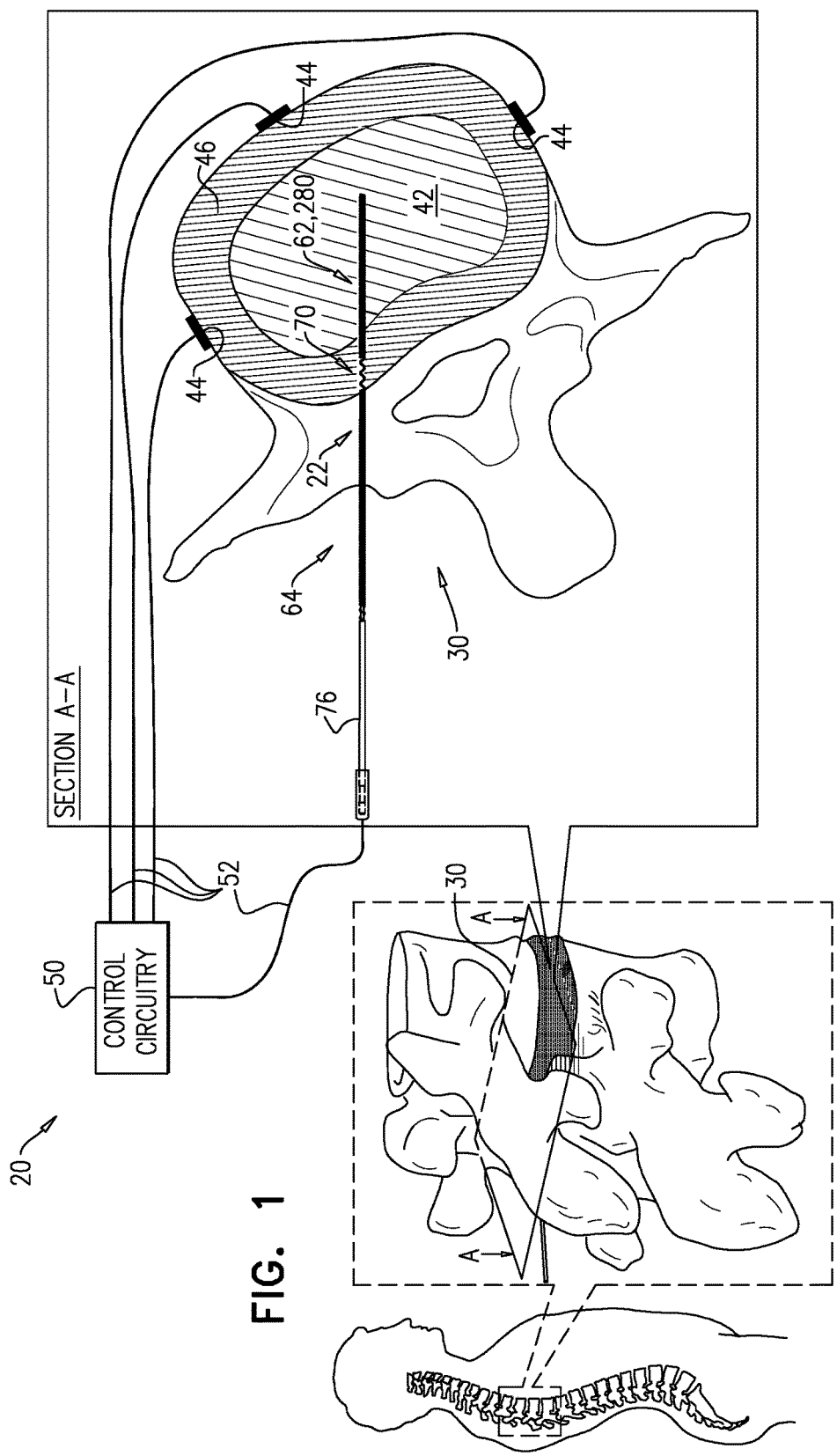
FIG. 1 is a schematic illustration of an intervertebral-disc-treatment system for treating an intervertebral disc of a subject, in accordance with an application of the present invention.

FIG. 1 is a schematic illustration of an intervertebral-disc-treatment system 20 for treating an intervertebral disc 30 of a subject, in accordance with an application of the present invention. Intervertebral-disc-treatment system 20 comprises (a) an electrode 22, which is configured to be implanted (typically chronically) partially within a nucleus pulposus 42 of disc 30, and (b) one or more extra-pulposus exposed electrode surfaces 44, which are configured to be implanted (typically chronically) outside nucleus pulposus 42, in electrical communication with disc 30, in a vicinity of an external surface of an annulus fibrosus 46 of disc 30, e.g., in physical contact with the external surface or not in physical contact with the external surface. Intervertebral-disc-treatment system 20 further comprises implantable (typically chronically implantable) or external control circuitry 50, which is typically electrically coupled, by one or more electrode leads 52, to (a) exposed electrode surfaces 44 and (b) electrode 22, such as via pin 76, described hereinbelow with reference to FIG. 2.

Typically, a healthcare worker, such as a physician, activates control circuitry 50 to provide the functions described herein. Activating the control circuitry may include configuring parameters and/or functions of the control circuitry (such as using a separate programmer or external controller), or activating the control circuitry to perform functions pre-programmed in the control circuitry. Control circuitry 50 typically comprises appropriate memory, processor(s), and hardware running software that is configured to provide the functionality of the control circuitry described herein.

Figure 2:
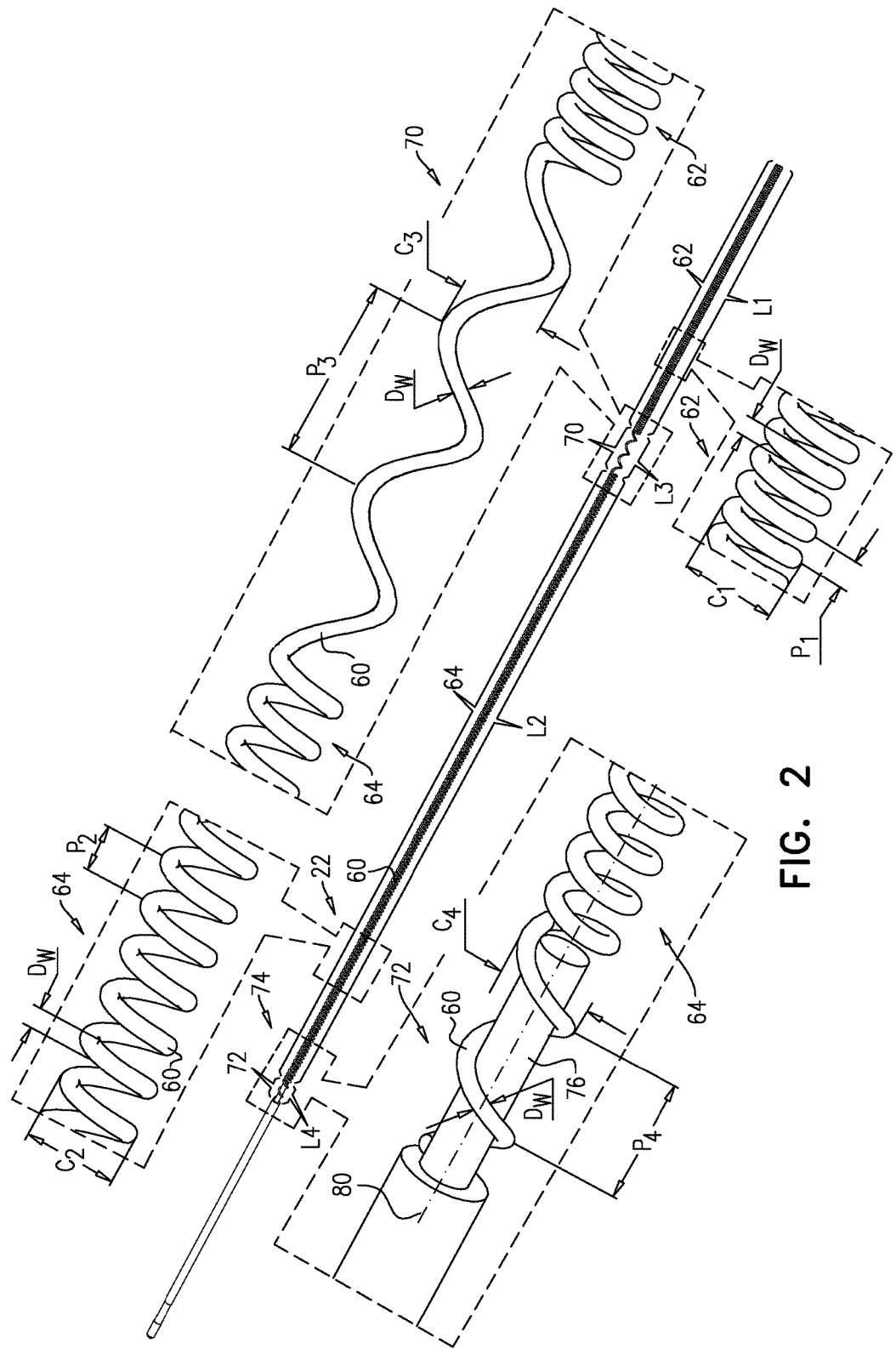
FIG. 2 is a schematic illustration of an electrode of the intervertebral-disc-treatment system of FIG. 1, in accordance with an application of the present invention.

Reference is made to FIG. 2, which is a schematic illustration of electrode 22, in accordance with an application of the present invention. Electrode 22 comprises a wire 60, which typically has a wire diameter $D_W$ of at least 50 microns (more typically at least 75 microns, such as at least 90 microns, e.g., at least 95 microns), no more than 150 microns (more typically no more than 125 microns, such as no more than 110 microns, e.g., no more than 105 microns), and/or between 50 microns (more typically 75 microns, such as 90 microns, e.g., 95 microns) and 150 microns (more typically 125 microns, such as 110 microns, e.g., 105 microns), such as 100 microns.

Wire 60 includes:
a non-electrically-insulated current-application longitudinal segment 62, which, in the absence of any applied forces, is helically coiled (referred to simply as "coiled" herein, including in the claims) and typically has (a) a mean pitch $P_1$ of at least 1.1 (e.g., at least 1.2, such as at least 1.4), no more than 2 (e.g., no more than 1.8, such as no more than 1.6), and/or between 1.1 and 2 (e.g., between 1.2 and 1.8, such as between 1.4 and 1.6, e.g., 1.5) times the wire diameter $D_W$, and (b) an entire longitudinal length $L_1$ of at least 5 mm (e.g., at least 10 mm), no more than 35 mm (e.g., no more than 25 mm), and/or between 5 and 35 mm (e.g., between 10 and 25 mm), and an electrically-insulated lead longitudinal segment 64, which typically has an entire longitudinal length $L_2$ of at least 5 mm (e.g., at least 10 mm), no more than 80 mm (e.g., no more than 50 mm), and/or between 5 and 80 mm (e.g., between 10 and 50 mm), in the absence of any applied forces.

As used in the present application, including in the claims, the pitch of a coil is the distance from any point on the coil to the corresponding point on an adjacent coil measured parallel to the central longitudinal axis. As used in the present application, including in the claims, the longitudinal length of segment is measured in a line along a central longitudinal axis of the segment (rather than being measured around the coil itself of the wire).

Typically, current-application longitudinal segment 62 extends to a distal end 66 of wire 60. For some applications, electrode 22 has a total length of at 50 mm (e.g., at least 70 mm), no more than 110 mm (e.g., no more than 90 mm), and/or between 50 and 110 mm (e.g., between 70 and 90 mm), such as 80 mm.

For some applications, electrically-insulated lead longitudinal segment 64 is coated with parylene, or another biocompatible non-conducting material known in the art.

For some applications, current-application longitudinal segment 62 has an outer coil diameter $C_1$ of at least 3 (e.g., at least 4), no more than 7 (e.g., no more than 6), and/or between 3 and 7 (e.g., between 4 and 6), e.g., 5, times the wire diameter $D_W$, in the absence of any applied forces. Alternatively or additionally, for some applications, the outer coil diameter $C_1$ is at least 400 microns (e.g., at least 450 microns), no more than 600 microns (e.g., no more than 550 microns), and/or between 400 and 600 microns (e.g., between 450 and 550 microns), e.g., 500 microns, in the absence of any applied forces.

Typically, because of the above-mentioned dimensions, including the pitch, current-application longitudinal segment 62 is highly flexible (both in its ability to bend and its ability to longitudinally stretch and contract), which reduces the application of forces on intervertebral disc 30, and thus generally causes no or less trauma to intervertebral disc 30, including nucleus pulposus 42, than a more rigid electrode might cause, particularly over time during repeated motion of the disc.

For some applications, lead longitudinal segment 64 is coiled, in the absence of any applied forces, such as shown in the figures. For some applications, lead longitudinal segment 64 has one or more of the following dimensions, in the absence of any applied forces:
- a mean pitch $P_2$ that is greater than (such as at least 125% of, e.g., at least 150% of, at least 175% of, at least 200% of, or at least 250% of) the mean pitch $P_1$ of current-application longitudinal segment 62,
- a mean pitch $P_2$ of at least 2 (e.g., at least 2.2, such as at least 2.4), no more than 3 (e.g., no more than 2.8, such as no more than 2.6), and/or between 2 and 3 (e.g., between 2.2 and 2.8, such as between 2.4 and 2.6), e.g., 2.5, times the wire diameter $D_W$,
- an outer coil diameter $C_2$ that equals between 90% and 110% (e.g., 100%) of the outer coil diameter $C_1$ of current-application longitudinal segment 62, and/or
- an outer coil diameter $C_2$ of at least 3 (e.g., at least 4), no more than 7 (e.g., no more than 6), and/or between 3 and 7 (e.g., between 4 and 6), e.g., 5, times the wire diameter $D_W$.

Typically, providing the above-mentioned pitches enables the thorough application of insulation to electrically-insulated lead longitudinal segment 64, particularly if a vapor deposition process is used to apply the insulation (e.g., parylene). In addition, lead longitudinal segment 64 may have a greater pitch than current-application longitudinal segment 62 in part because lead longitudinal segment 64 generally does not require as much flexibility as current-application longitudinal segment 62.

For other applications, lead longitudinal segment 64 is not coiled, in the absence of any applied forces; for example, lead longitudinal segment 64 may be straight or zigzag-shaped (configurations not shown).

Figure 3A:
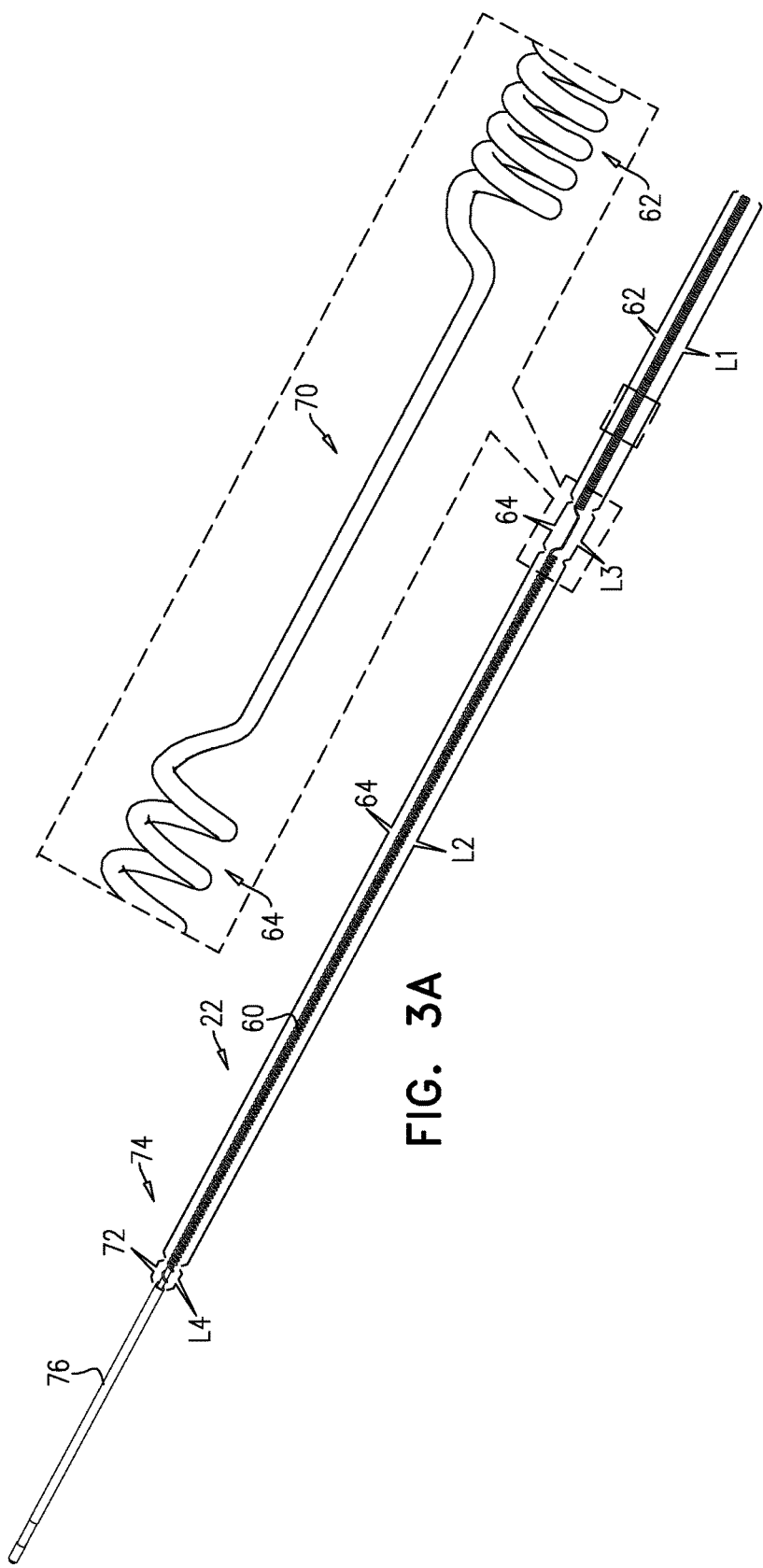
FIG. 3A is a schematic illustration of another configuration of the electrode of FIG. 2, in accordance with an application of the present invention.
Figure 3B:
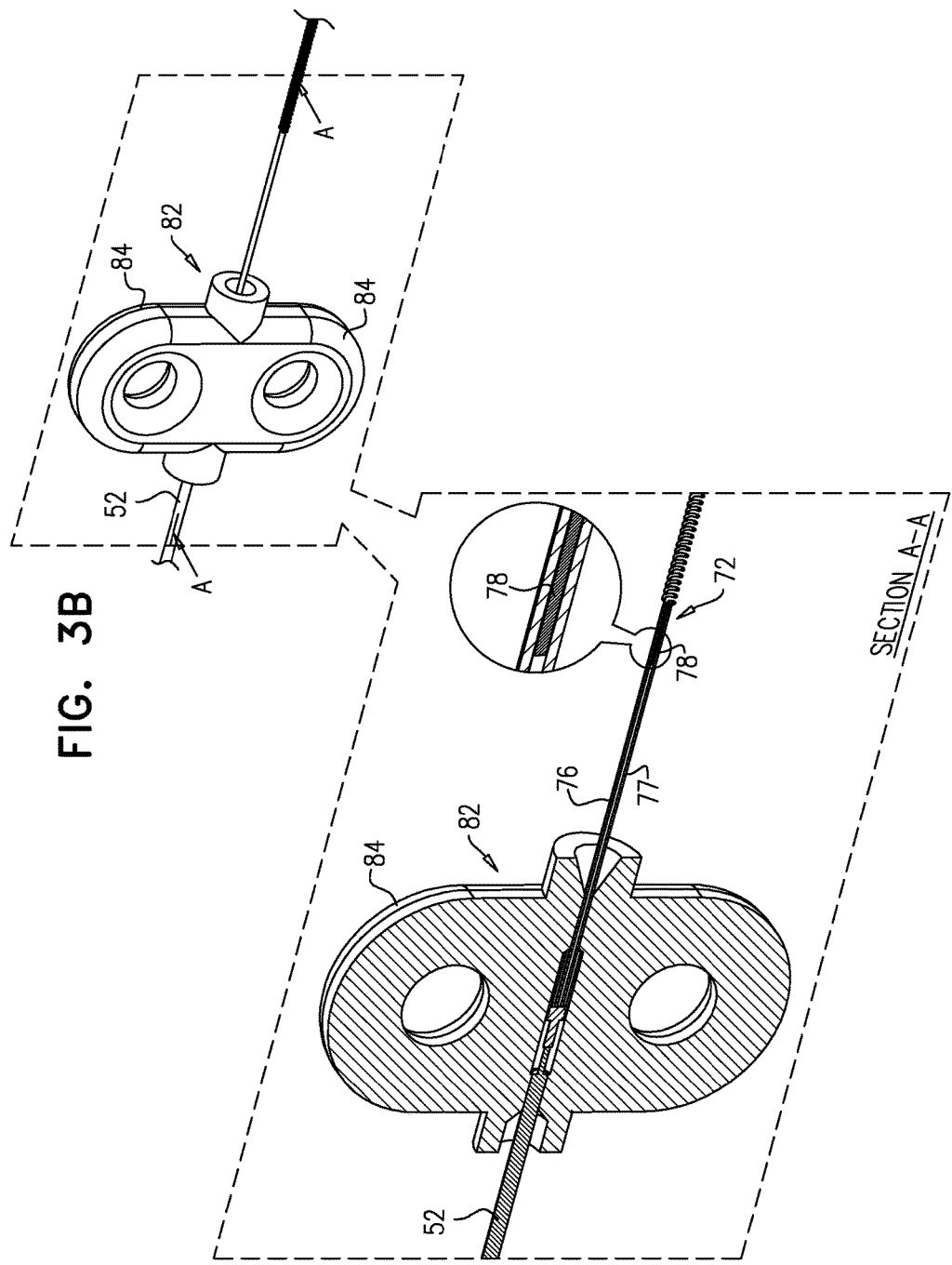
FIG. 3B is a schematic illustration of yet another configuration of the electrode of FIG. 2, in accordance with an application of the present invention.

For some applications, wire 60 further includes an intermediate longitudinal segment 70, which (a) is longitudinally between current-application longitudinal segment 62 and lead longitudinal segment 64, (b) typically has an entire longitudinal length $L_3$ of at least 1 mm (e.g., at least 2 mm), no more than 6 mm (e.g., no more than 4 mm), and/or between 1 and 6 mm (e.g., between 2 and 4 mm), in the absence of any applied forces, and (c) in the absence of any applied forces, either (i) is coiled, and has a mean pitch $P_3$ greater than outer coil diameter $C_1$ of current-application longitudinal segment 62, as shown in FIG. 2, or (ii) is not coiled, as shown in FIGS. 3A-B. (As used in the present application, including the claims, when a segment is described as "longitudinally between" two other segments, the segment is not necessarily adjacent to the two other segments. In other words, additional segments, which may or may not be mentioned, may longitudinally intervene between the segment and one or both of the two other segments.)

For some applications, intermediate longitudinal segment 70 is electrically insulated along at least a longitudinal portion of intermediate longitudinal segment 70.

For some applications in which intermediate longitudinal segment 70 is coiled, intermediate longitudinal segment 70 has one or more of the following dimensions, in the absence of any applied forces:
- a mean pitch $P_3$ of at least 125%, no more than 250%, and/or between 125% and 250% of the outer coil diameter $C_1$ of current-application longitudinal segment 62,
- a mean pitch $P_3$ of at least 5 (e.g., at least 6, such as at least 9), no more than 20 (e.g., no more than 13, such as no more than 11), and/or between 5 and 20 (e.g., between 6 and 13, such as between 9 and 11), e.g., 10, times the wire diameter $D_W$,
- a mean pitch $P_3$ that equals (a) at least mean pitch $P_1$ of current-application longitudinal segment 62, and (b) no more than mean pitch $P_2$ of lead longitudinal segment 64,
- an outer coil diameter $C_3$ equal to between 90% and 110% (e.g., 100%) of the outer coil diameter $C_1$ of current-application longitudinal segment 62, and/or
- an outer coil diameter $C_3$ of at least 3 (e.g., at least 4), no more than 7 (e.g., no more than 6), and/or between 3 and 7 (e.g., between 4 and 6) times the wire diameter $D_W$.

Reference is now made to FIG. 3A, which is a schematic illustration of another configuration of electrode 22, in accordance with an application of the present invention. This configuration is the same as the configuration described hereinabove with reference to FIG. 2, except that intermediate longitudinal segment 70 is not coiled, in the absence of any applied forces.

For some applications, wire 60 further includes a partially non-electrically-insulated pin-connector longitudinal segment 72. Lead longitudinal segment 64 is longitudinally between current-application longitudinal segment 62 and pin-connector longitudinal segment 72. For these applications, intervertebral-disc-treatment system 20 typically comprises an electrode assembly 74, which comprises electrode 22 and a pin 76, which is mechanically fixed to and in electrical communication with pin-connector longitudinal segment 72. Pin 76 and pin-connector longitudinal segment 72 are permanently connected, typically by welding (e.g., laser or spot welding).

For some applications, such as shown, pin-connector longitudinal segment 72 is coaxial with a central longitudinal axis 80 of electrically-insulated lead longitudinal segment 64, in the absence of any applied forces.

For some applications, such as shown in FIGS. 2 and 3A, pin-connector longitudinal segment 72 is coiled, in the absence of any applied forces. For some of these applications, such as shown in FIGS. 2 and 3A, coiled pin-connector longitudinal segment 72 is welded to the outside of pin 76.

For some applications, pin-connector longitudinal segment 72 has one or more of the following dimensions, in the absence of any applied forces:
- a mean pitch $P_4$ that equals at least 125%, no more than 250%, and/or between 125% and 250% of the outer coil diameter $C_2$ of current-application longitudinal segment 62,
- a mean pitch $P_4$ of at least 5, no more than 20 (e.g., no more than 10, such as no more than 7), and/or between 5 and 20 (e.g., between 5 and 10, such as between 3 and 7 times), e.g., 7, times the wire diameter $D_W$,
- an outer coil diameter $C_4$ that equals between 90% and 110% (e.g., 100%) of the outer coil diameter $C_2$ of current-application longitudinal segment 62,
- an outer coil diameter $C_4$ of at least 3 (e.g., at least 4), no more than 7 (e.g., no more than 6), and/or between 3 and 7 (e.g., between 4 and 6), e.g., 5, times the wire diameter $D_W$, and/or
- an entire longitudinal length $L_4$ of between 1 and 4 mm.

Reference is now made to FIG. 3B, which is a schematic illustration of yet another configuration of electrode 22, in accordance with an application of the present invention. In this configuration, pin 76 is shaped as a tube 77 that defines a lumen. An end portion 78 of pin-connector longitudinal segment 72 may be a straight section located along the axis of pin-connector longitudinal segment 72. For example, the connection may be fixated by crimping the tube of pin 76 on the wire of pin-connector longitudinal segment 72. The coating (e.g., parylene coating) covers this section as well. Typically, the only part of pin 76 that is not be coated is the proximal end thereof, which serves as an electrical connector pin (by being insertable into a female electrical connector, typically after the electrode has been implanted). The electrical path is thus electrically connected to the control circuitry 50 and insulated from the body. For some applications, a seal 82 (e.g., comprising silicone) is provided that surrounds the connector/pin interface with electrode lead 52 to control circuitry 50. Optionally, seal 82 is shaped so as to define wings 84, which may be used to anchor the system.

For some applications, one or more of current-application longitudinal segment 62, lead longitudinal segment 64, intermediate longitudinal segment 70, and pin-connector longitudinal segment 72 has an inner coil diameter of at least 0.25 (e.g., at least 0.27), no more than 0.36 (e.g., no more than 0.33), and/or between 0.25 and 0.36 (e.g., between 0.27 and 0.33). e.g., 0.6, times the respective outer coil diameter of the segment, in the absence of any applied forces.

Typically, wire 60 has the same diameter $D_W$ along all of current-application longitudinal segment 62, lead longitudinal segment 64, intermediate longitudinal segment 70, and pin-connector longitudinal segment 72. Alternatively, diameter $D_W$ varies between one or more of current-application longitudinal segment 62, lead longitudinal segment 64, intermediate longitudinal segment 70, and/or pin-connector longitudinal segment 72.

For some applications, the coil of one or more longitudinal segments of electrode 22 is filled with a pharmaceutical, such as an antibiotic pharmaceutical, an anti-inflammation pharmaceutical, or an analgesic pharmaceutical.

Figure 4:
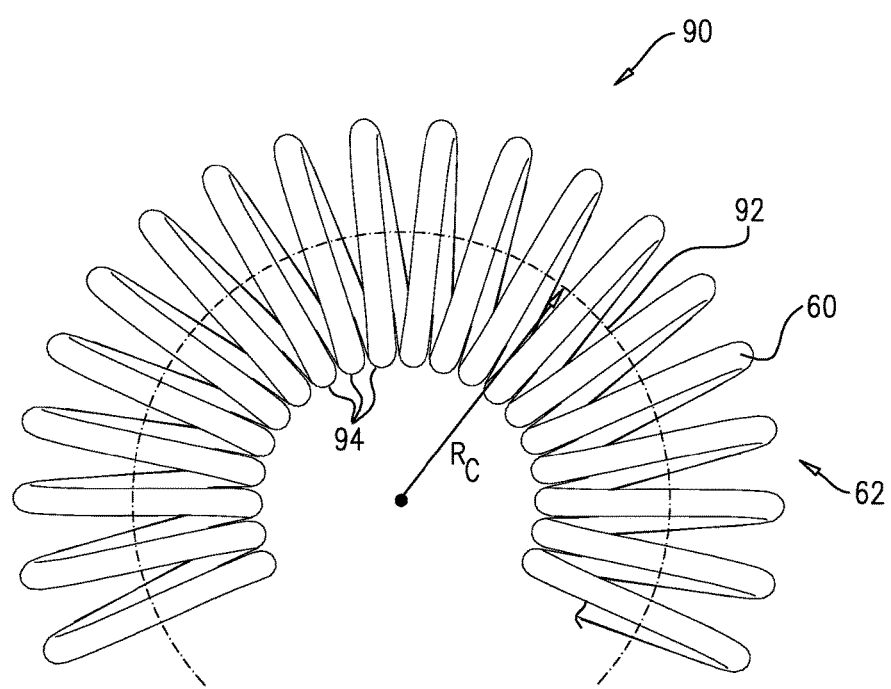
FIG. 4 is a schematic illustration of a 3-mm long portion of a current-application longitudinal segment of the electrode of FIG. 2, FIG. 3A, or FIG. 3B, in accordance with an application of the present invention.

Reference is now made to FIG. 4, which is a schematic illustration of a 3-mm long portion 90 of current-application longitudinal segment 62, in accordance with an application of the present invention. This configuration is applicable to the configurations of electrode 22 of FIGS. 2, 3, and/or 5. For some applications, when a central longitudinal axis 92 of 3-mm long portion 90 (measured along central longitudinal axis 92 when the portion is straight, in the absence of any applied forces) of current-application longitudinal segment 62 is curved in a plane only until all adjacent turns 94 of coiled wire 60 of portion 90 touch one another, central longitudinal axis 92 of the portion has a radius of curvature $R_C$ of at least 5 mm, no more than 10 mm, and/or between 5 and 10 mm.

Such a radius of curvature provides current-application longitudinal segment 62 with the flexibility to curve and flex. If, on the one hand, adjacent turns 94 of coiled wire 60 instead touched one other in the absence of any applied forces, current-application longitudinal segment 62 would not have such flexibility to curve. If, on the other hand, mean pitch $P_1$ of current-application longitudinal segment 62 were substantially larger, current-application longitudinal segment 62 might be too stiff.

For some applications, lead longitudinal segment 64 has the curvature parameters described hereinabove with reference to FIG. 4.

Figure 5:
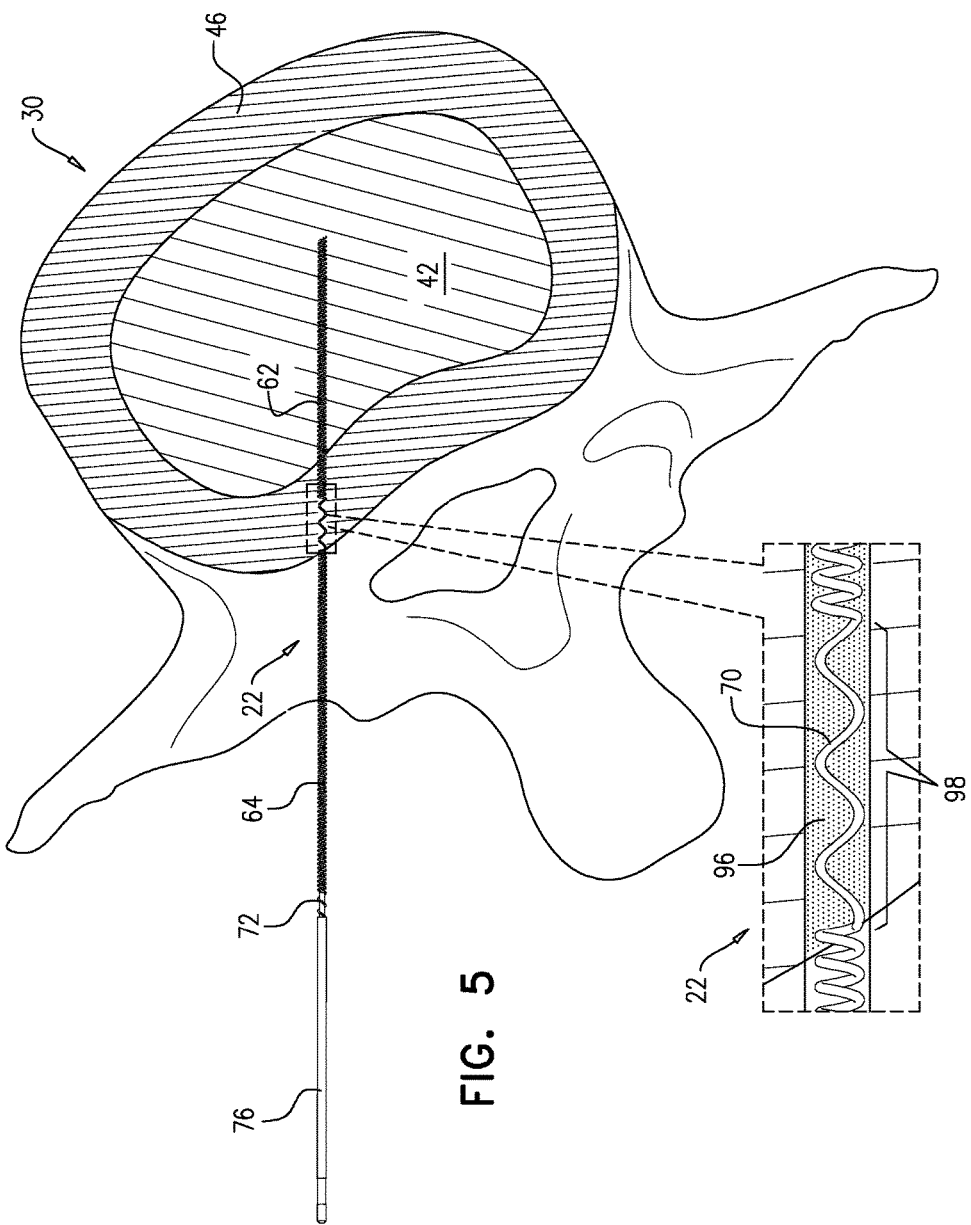
FIG. 5 is a schematic illustration of another configuration of the electrode of FIG. 2, in accordance with an application of the present invention.

Reference is now made to FIG. 5, which is a schematic illustration of another configuration of electrode 22, in accordance with an application of the present invention. In this configuration, electrode 22 further comprises a water-permeable element 96 that runs along at least a longitudinal portion 98 of intermediate longitudinal segment 70, thereby enhancing fluid flow through annulus fibrosus 46 caused by the application of the voltage, to a level greater than possible through other portions of annulus fibrosus 46. For some applications, water-permeable element 96 comprises a membrane. Alternatively or additionally, for some applications, water-permeable element 96 comprises an acid selected from the group consisting of: glycolic acid and lactic acid. For some applications, water-permeable element 96 is pre-attached to longitudinal portion 98. Alternatively, water-permeable element 96 may be placed separately into the bore through annulus fibrosus 46.

For some of these applications, intermediate longitudinal segment 70 is coiled, in the absence of any applied forces, such as described hereinabove with reference to FIG. 2, and water-permeable element 96 is disposed within the channel defined by the coil. Alternatively or additionally, intermediate longitudinal segment 70 is partially or entirely embedded in intermediate longitudinal segment 70.

Reference is again made to FIG. 1. At least a portion of electrode 22 is implanted in a body of a subject, typically such that:
    current-application longitudinal segment 62 is disposed at least partially in intervertebral disc 30 of the subject, typically entirely in intervertebral disc 30 (either entirely in nucleus pulposus 42 of intervertebral disc 30, or partially in a nucleus pulposus of intervertebral disc 30 and partially in annulus fibrosus 46 of intervertebral disc 30, as shown in FIG. 1),
    at least a portion of lead longitudinal segment 64 is disposed in the body of the subject outside intervertebral disc 30, and
    if provided, intermediate longitudinal segment 70 is disposed at least in part in annulus fibrosus 46 of intervertebral disc 30, providing the relatively large pitch for intermediate longitudinal segment 70, or not coiling intermediate longitudinal segment 70 (as described hereinabove with reference to FIG. 3), may reduce the likelihood that the portion of intermediate longitudinal segment 70 that is within annulus fibrosus 46 forms a tunnel, which might cause leakage of fluid from nucleus pulposus 42.

Figure 6:
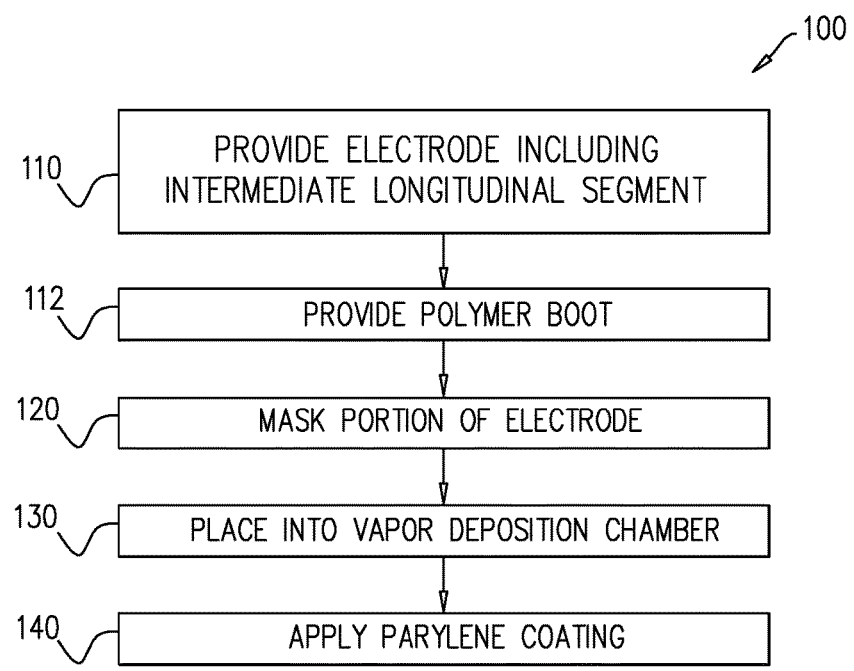
FIG. 6 is a flow chart illustrating a method of manufacturing the electrode of FIG. 2, of FIG. 3A, or of FIG. 3B, in accordance with an application of the present invention.
Figure 7:
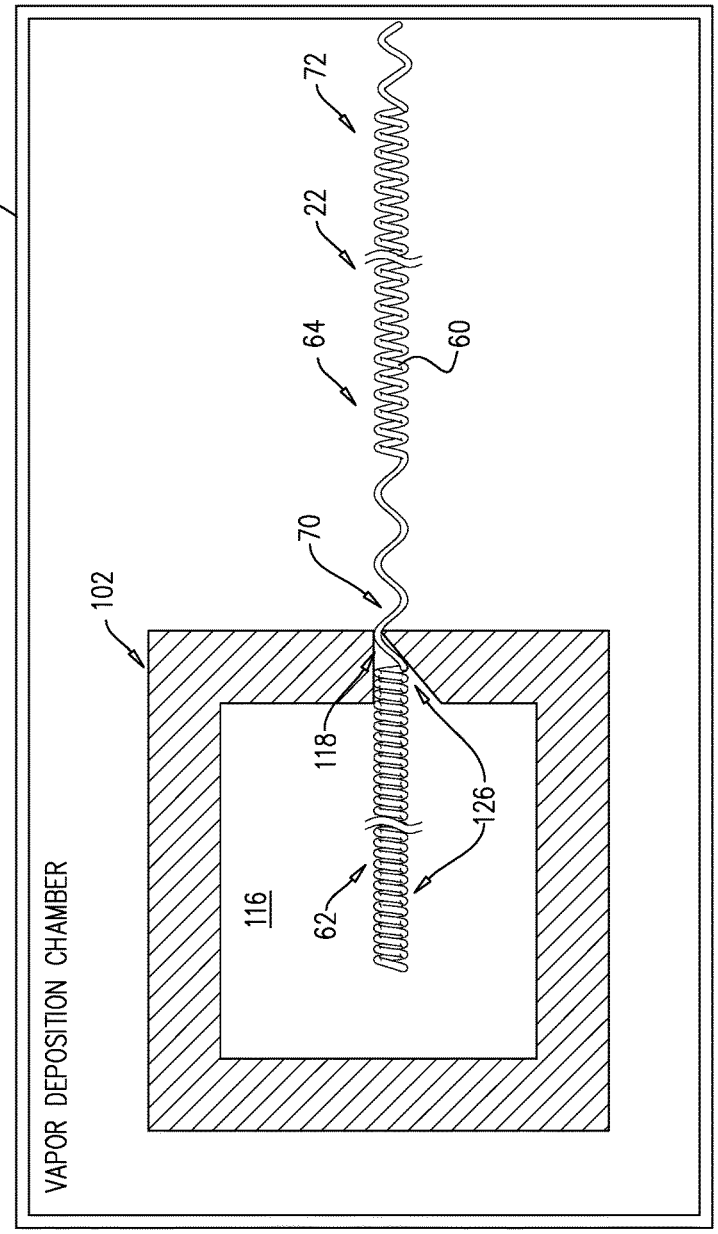
FIG. 7 is a schematic illustration of a polymer boot used in the manufacturing method of FIG. 6, in accordance with an application of the present invention.

Reference is now made to FIG. 6, which is a flow chart illustrating a method 100 of manufacturing electrode 22, in accordance with an application of the present invention, and to FIG. 7, which is a schematic illustration of a polymer boot 102 used in manufacturing method 100, in accordance with an application of the present invention. Manufacturing method 100 may be used to manufacture the configurations of electrode 22 of FIGS. 2, 3, and/or 5. Manufacturing method 100 begins at an electrode provision step 110 by providing electrode 22, in any of the configurations described hereinabove that include intermediate longitudinal segment 70, before electrically-insulated lead longitudinal segment 64 has been coated with an electrically-insulating coating. As mentioned above, intermediate longitudinal segment 70, in the absence of any applied forces, either (a) is coiled and has a mean pitch $P_3$ that is greater than an outer coil diameter $C_1$ of current-application longitudinal segment 62 or (b) is not coiled.

At a polymer boot provision step 112, polymer boot 102 is provided; for some applications, polymer boot 102 comprises a silicone boot. Polymer boot 102 is shaped so as to define an enclosed space 116 with an opening 118 having a perimeter.

At masking step 120, a portion 126 of electrode 22 is masked by placing boot 102 on portion 126 of electrode 22, such that:

current-application longitudinal segment 62 is within enclosed space 116, lead longitudinal segment 64 is outside boot 102, and intermediate longitudinal segment 70 passes through opening 118 such that the perimeter of opening 118 forms a tight seal with at least a portion of intermediate longitudinal segment 70.

At a vapor deposition chamber step 130, boot 102 and electrode 22 are placed into a vapor deposition chamber 134 (which is illustrated highly schematically in FIG. 7). At a parylene coating step 140, a parylene coating (or another biocompatible non-conducting material known in the art) is applied to lead longitudinal segment 64 by vapor deposition within deposition chamber 134, as is known in the vapor deposition art. Boot 102 and electrode 22 are removed from vapor deposition chamber 134, and boot 102 is removed from electrode 22.

This masking technique, in combination with the geometry of electrode 22, solves the problem of how to tightly mask current-application longitudinal segment 62 during vapor deposition of electrically-insulating parylene onto lead longitudinal segment 64. The perimeter of opening 118 of boot 102, when applied to the high-coil-pitch, or coil-lacking, intermediate longitudinal segment 70, tightly squeezes the intermediate longitudinal segment, thereby preventing gaseous leakage of the parylene into the boot and onto current-application longitudinal segment 62. Such tight squeezing would not be possible if intermediate longitudinal segment 70 were more tightly coiled (i.e., had a lower coil pitch).

Reference is now made to FIG. 8, which is schematic illustrations of an implantation system 200 for implanting at least a portion of electrode 22 in a body of a subject, in accordance with an application of the present invention. Implantation system 200 may be used to implant the configurations of electrode 22 of FIGS. 2, 3, and/or 5. Implantation system 200 comprises the following components, each of which is described in detail hereinbelow:

a hollow insertion needle 210, which, at a proximal end thereof, is axially fixed to a needle-connection fitting 212; insertion needle 210 is used for inserting electrode 22 partially into intervertebral disc 30, as described hereinbelow with reference to FIGS. 11A-B; typically, insertion needle 210 has a length of between 60 and 120 mm, such as between 80 and 100 mm, e.g., 90 mm;

a spacer 216, which defines a channel therethrough for insertion of insertion needle 210 from a proximal side 218 of spacer 216 to a distal side 220 of spacer 216, until needle-connection fitting 212 abuts proximal side 218 of spacer 216; spacer 216 serves to limit a depth of penetration of insertion needle 210, as described hereinbelow with reference to FIGS. 11A-B;

an electrode loader 224, which is used to advance electrode 22 into insertion needle 210, as described hereinbelow with reference to FIGS. 13A-15B; and a needle-withdrawal handle 228, which is used to withdrawn insertion needle 210 from disc 30 after delivery of electrode 22 into the disc, as described hereinbelow with reference to FIGS. 16A-18C.

For some applications, one or more (e.g., all) of the components of implantation system 200 are provided as a kit, typically in sterile packaging 202. The components of implantation system 200 may be provided in various stages of assembly, depending on packaging needs and other factors. Typically, electrode 22 is also provided in the kit, such as in the same sterile packaging 202 as the components of implantation system 200.

Figure 9A:
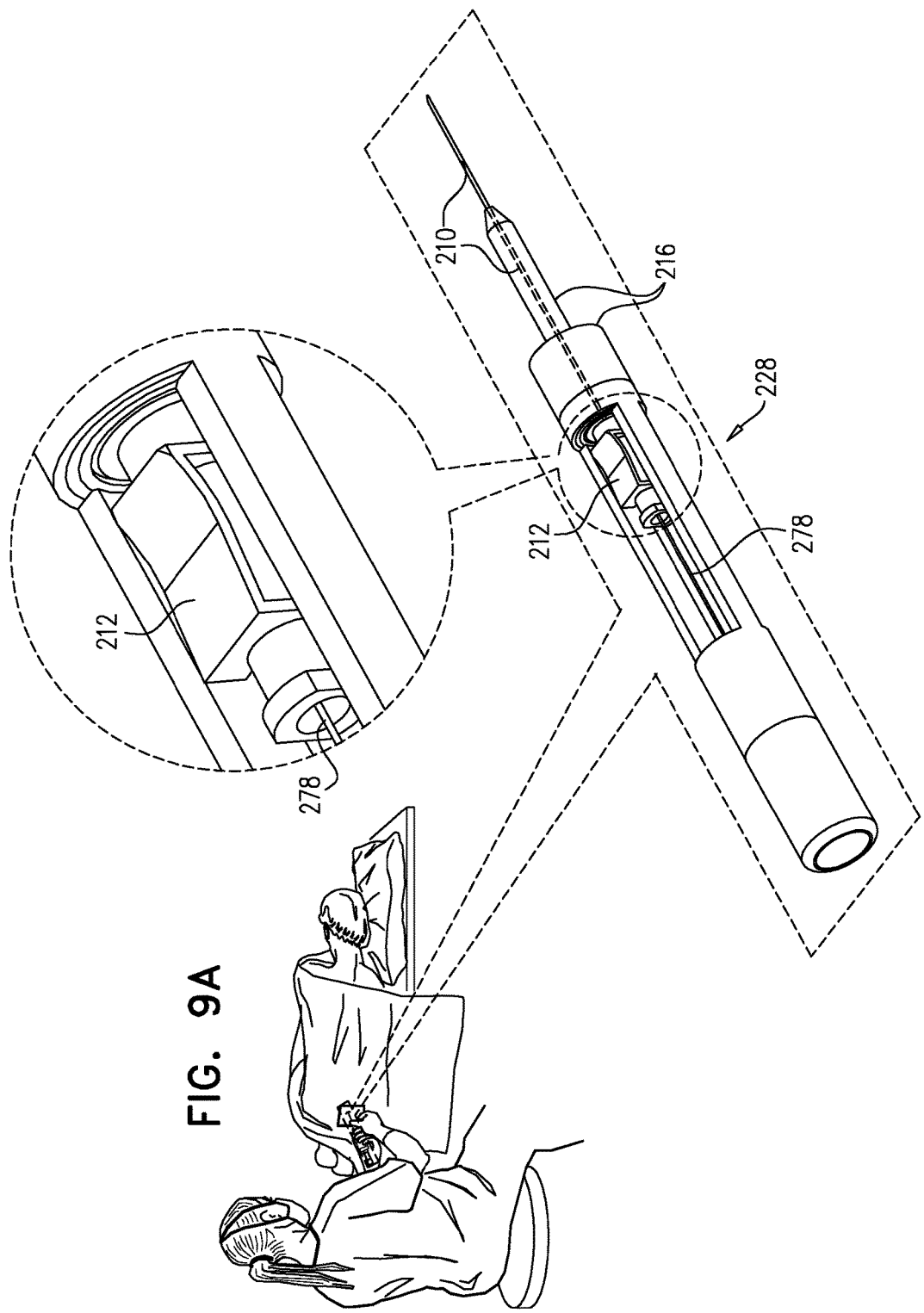

Reference is now made to FIGS. 9A-B, which are schematic illustrations of several components of implantation system 200, in accordance with an application of the present invention. FIG. 9A shows needle-withdrawal handle 228 attached to spacer 216, while insertion needle 210 passes through the channel of spacer 216. FIG. 9A also shows needle-connection fitting 212 fixed to insertion needle 210 and disposed within needle-withdrawal handle 228. FIG. 9B shows the relationship of the above-mentioned components.

Figure 10:
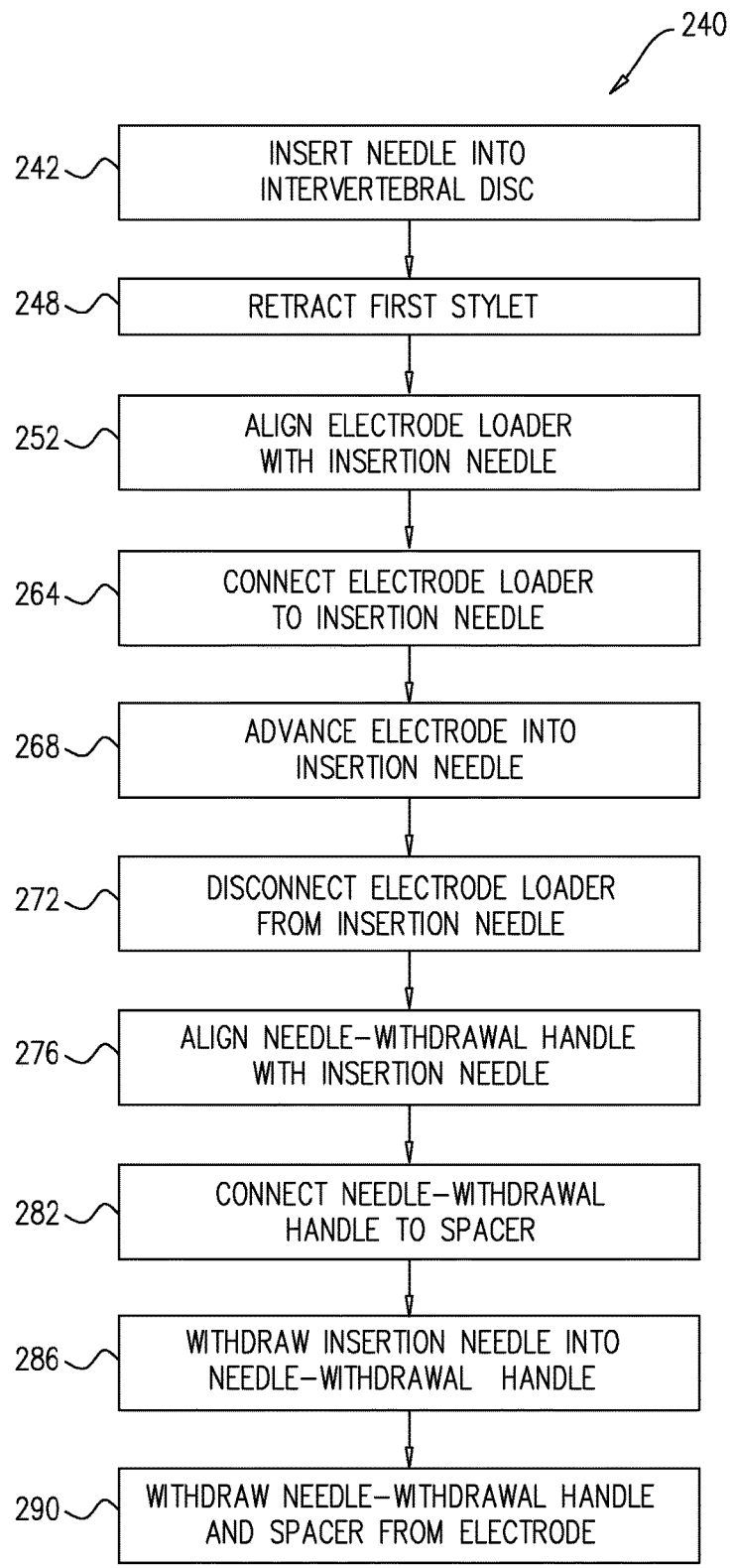
FIG. 10 is a flow chart illustrating a method of implanting at least a portion of the electrode of FIG. 2 in a body of a subject, in accordance with an application of the present invention.

Reference is now made to FIG. 10, which is a flow chart illustrating a method 240 of implanting at least a portion of electrode 22 in a body of a subject, in accordance with an application of the present invention, and FIGS. 11A-20, which are schematic illustrations of steps of implantation method 240, in accordance with an application of the present invention. Implantation method 240 may be used to implant the configurations of electrode 22 of FIGS. 2, 3, and/or 5. Implantation method 240 uses implantation system 200, described hereinabove with reference to FIGS. 8 and 9A-B.

FIGS. 11A-B are schematic illustrations of a needle insertion step 242 of implantation method 240, in accordance with an application of the present invention. Before inserting insertion needle 210 into intervertebral disc 30, insertion needle 210 (which is axially fixed to a needle-connection fitting 212) is inserted through spacer 216. For example, needle-connection fitting 212 may be female, in which case needle-connection fitting 212 typically comprises a female Luer taper. Spacer 216 serves to limit a depth penetration of insertion needle 210, so that the insertion needle does not penetrate the far side of annulus fibrosus 46 of disc 30. Optionally, a length of spacer 216 is adjustable, or a set of spacers 216 having different respective lengths is provided, in order to accommodate discs 30 of different sizes.

Also before inserting insertion needle 210 into intervertebral disc 30, an anti-coring stylet 244 is inserted through needle-connection fitting 212 and spacer 216 and into insertion needle 210, with the distal end of anti-coring stylet 244 advanced to the distal end of insertion needle 210. For some applications, anti-coring stylet 244 has a beveled distal end 246 that conforms to the beveled distal end of insertion needle 210.

At needle insertion step 242, insertion needle 210 (with anti-coring stylet 244 therein) is partially inserted into disc 30, until spacer 216 contacts an external surface of annulus fibrosus 46. After insertion, the distal end of insertion needle 210 (and the distal end of anti-coring stylet 244) typically is near, but does not penetrate, the far side of annulus fibrosus 46. Alternatively, the distal end of insertion needle 210 (and the distal end of anti-coring stylet 244) is inserted into the far side of annulus fibrosus 46, e.g., to ultimately allow electrode 22 serve as an anchor. For some applications, the angle of penetration of the insertion needle is about 30 degrees.

FIG. 12 is a schematic illustration of an anti-coring stylet 244 retraction step 248 of implantation method 240, in accordance with an application of the present invention. At anti-coring stylet 244 retraction step 248, anti-coring stylet 244 is retracted, leaving insertion needle 210 in disc 30, and spacer 216 contacting the external surface of annulus fibrosus 46.

Figure 13A:
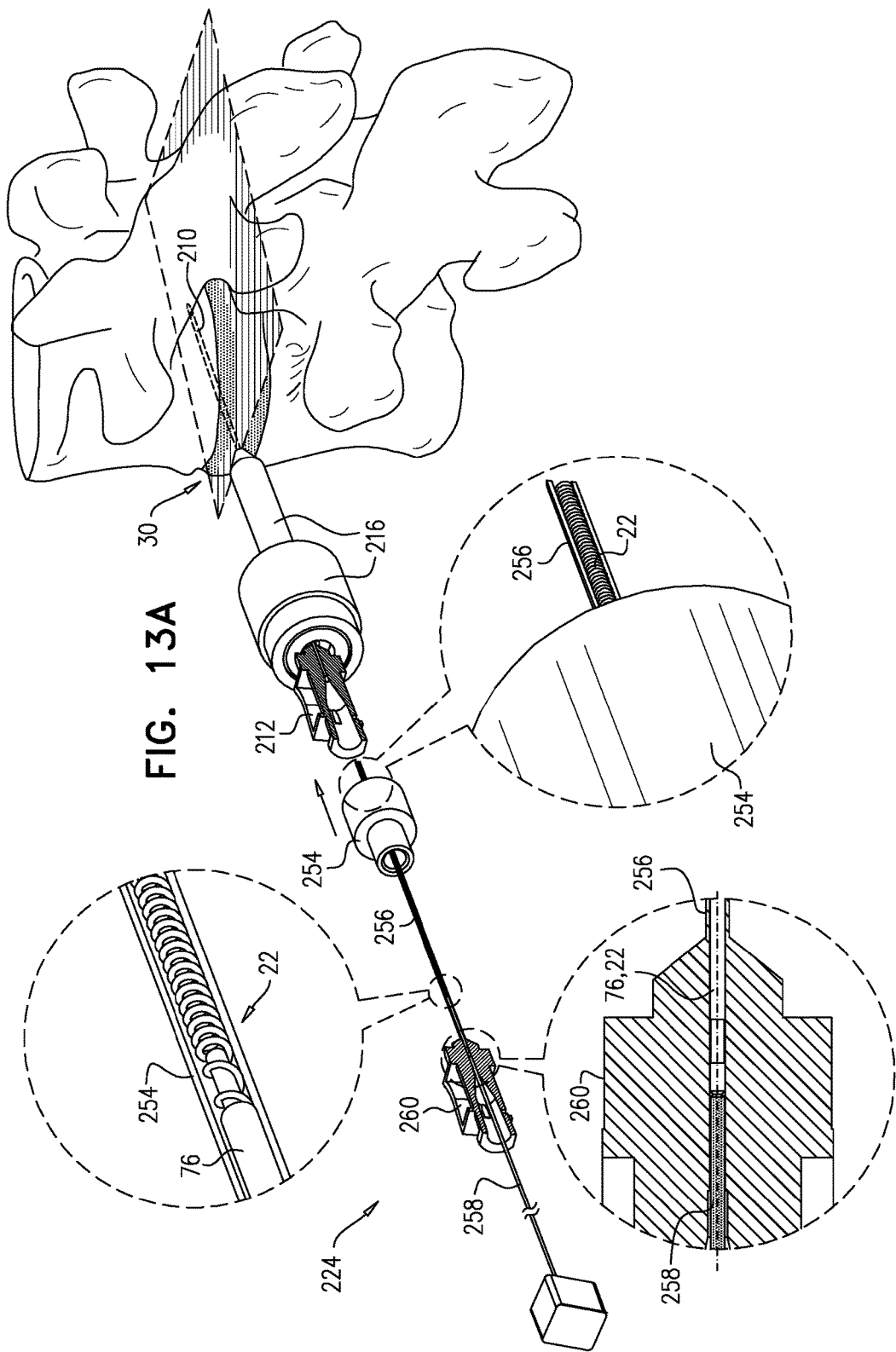

FIGS. 13A-C are schematic illustrations of an electrode loader alignment step 252 of implantation method 240, in accordance with an application of the present invention. Electrode loader 224 comprises an electrode-loader connection fitting 254, which, for example, may be male, in which case electrode-loader connection fitting 254 typically comprises a male Luer taper, which is mounted near a distal end of a hollow loader needle 256. Typically, loader needle 256 has a length of between 60 and 120 mm, such as between 80 and 100 mm, e.g., 90 mm.

Electrode 22 is loaded in loader needle 256, with a distal end of electrode 22 disposed near a distal end of loader needle 256. Electrode loader 224 also comprises a loader stylet 258, which is loaded partially within loader needle 256 and disposed such that a distal end of loader stylet 258 abuts a proximal end of electrode 22 (typically a proximal end of pin 76 of electrode 22). Typically, loader stylet 258 is not beveled at its distal end (i.e., it typically has a straight distal end). Loader stylet 258 is held in place by a connecting element 260, which may comprise a Luer connector, such that the distal end of loader stylet 258 can push electrode 22 distally, as described hereinbelow with reference to FIGS. 15A-B. At electrode loader alignment step 252, electrode loader 224 is aligned with insertion needle 210.

FIGS. 14A-B are schematic illustrations of an electrode-loader connection step 264 of implantation method 240, in accordance with an application of the present invention. At electrode-loader connection step 264, electrode loader 224 is connected to insertion needle 210, such as by connecting electrode-loader connection fitting 254 to needle-connection fitting 212, such as, for example, by way of rotation. As a result of this connection, a distal end of loader needle 256 abuts a proximal end of insertion needle 210.

FIGS. 15A-B are schematic illustrations of an electrode advancement step 268 of implantation method 240, in accordance with an application of the present invention. At electrode advancement step 268, loader stylet 258 is gently advanced distally within loader needle 256 and pushes electrode 22 distally from loader needle 256 into insertion needle 210, which, as mentioned above, is disposed partially in disc 30. For example, electrode 22 may penetrate about 2 cm into disc 30. Electrode-loader connection fitting 254 is disconnected from needle-connection fitting 212, at an electrode-loader disconnection step 272 (not shown), and electrode loader 224 is removed.

Figure 16A:
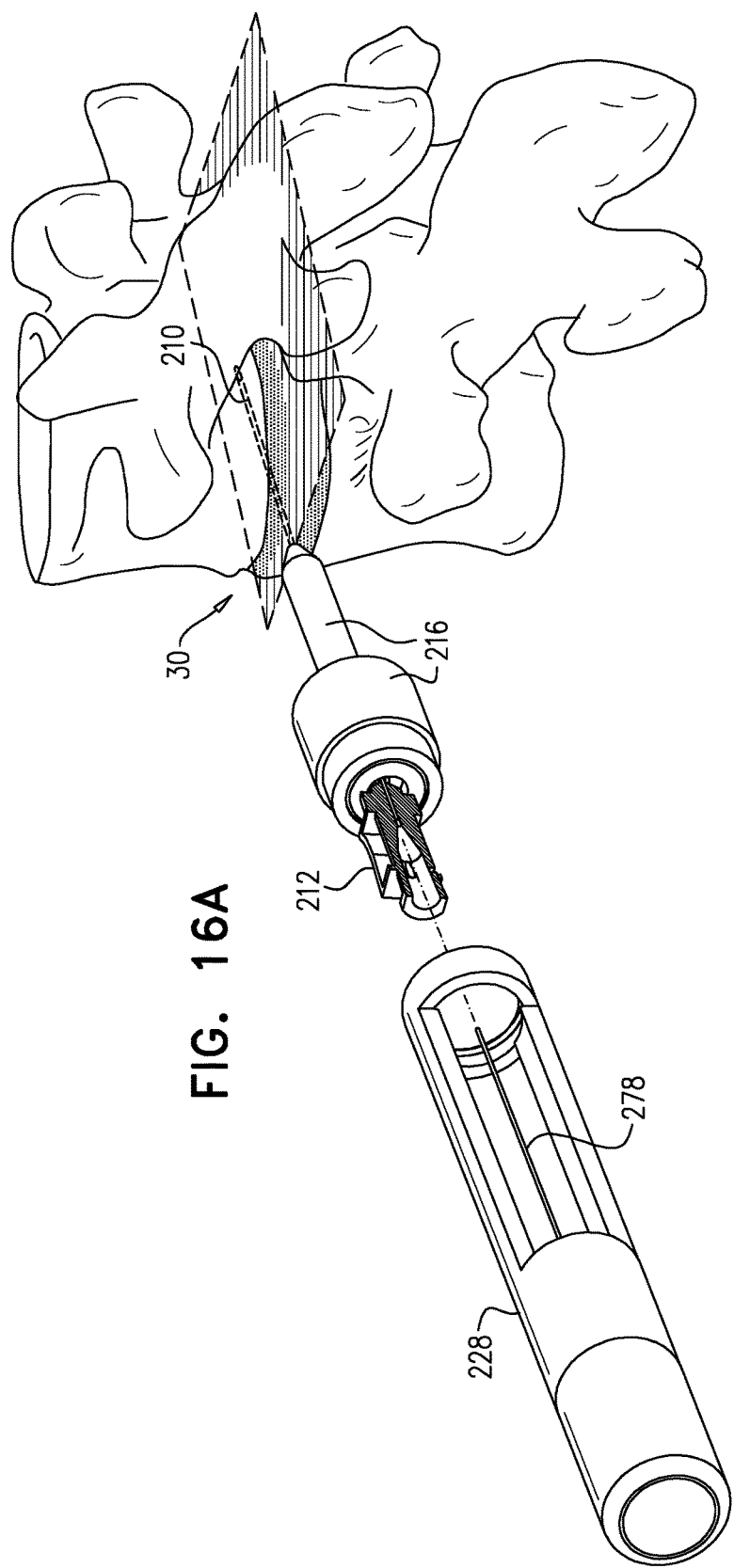
FIGS. 16A-C are schematic illustrations of a needle-withdrawal-handle alignment step of the implantation method of FIG. 10, in accordance with an application of the present invention.
Figures 16B, 16C:
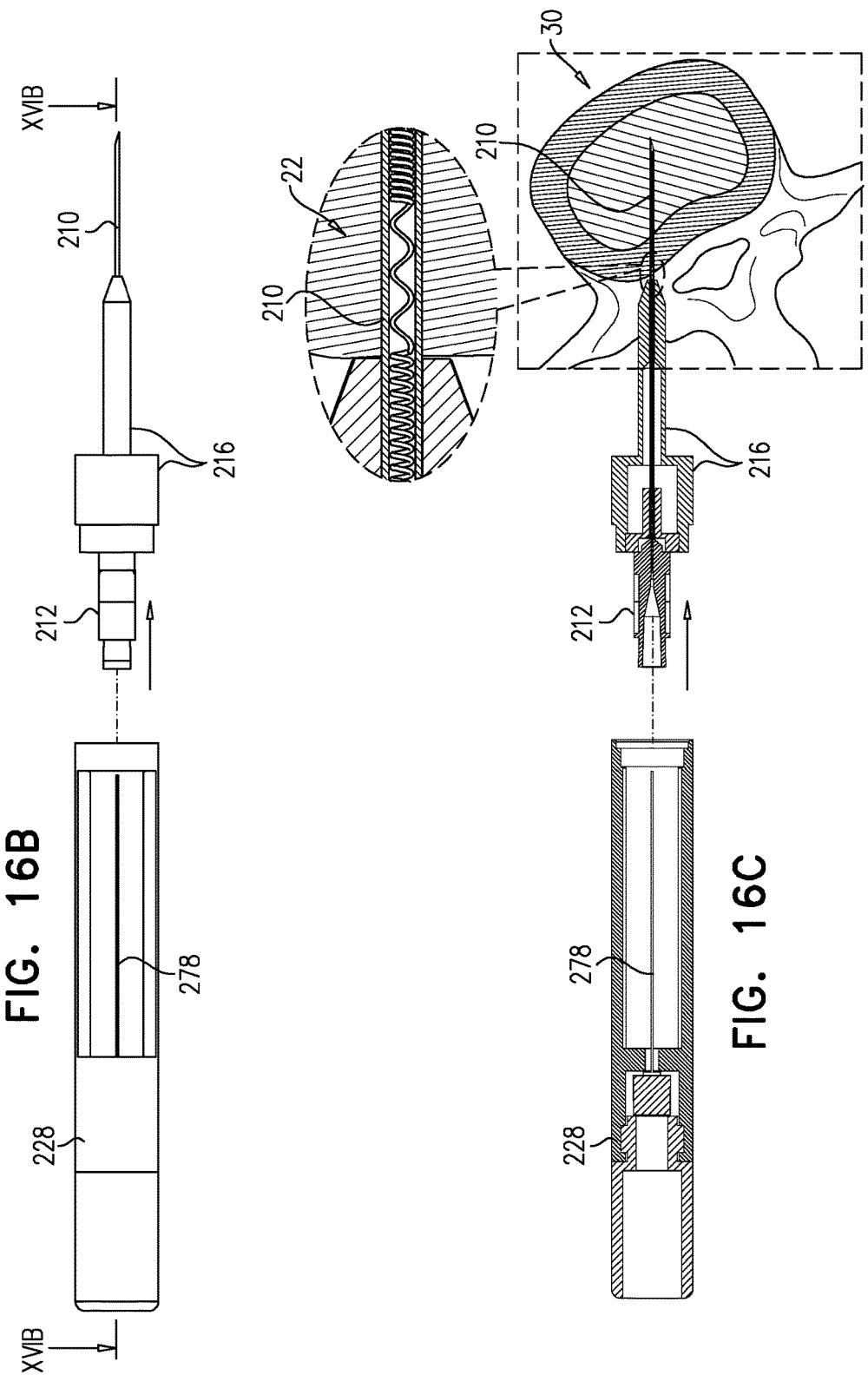

FIGS. 16A-C are schematic illustrations of a needle-withdrawal-handle alignment step 276 of implantation method 240, in accordance with an application of the present invention. Needle-withdrawal handle 228 comprises a handle stylet 278, which is typically axially fixed within the needle-withdrawal handle. At needle-withdrawal-handle alignment step 276, needle-withdrawal handle 228 and handle stylet 278 are aligned with insertion needle 210 (and spacer 216).

FIGS. 17A-B are schematic illustrations of a needle-withdrawal-handle connection step 282 of implantation method 240, in accordance with an application of the present invention. At needle-withdrawal-handle connection step 282, needle-withdrawal handle 228 is connected to insertion needle 210, such as by connecting needle-withdrawal handle 228 to spacer 216 (such as by friction, snapping on, and/or rotation). Upon the connection being made, needle-connection fitting 212 is disposed within needle-withdrawal handle 228, near a distal end of the needle-withdrawal handle, and the distal end of handle stylet 278 is disposed within needle-connection fitting 212 abutting the proximal end of electrode 22 (typically the proximal end of pin 76 of electrode 22).

Figure 18A:
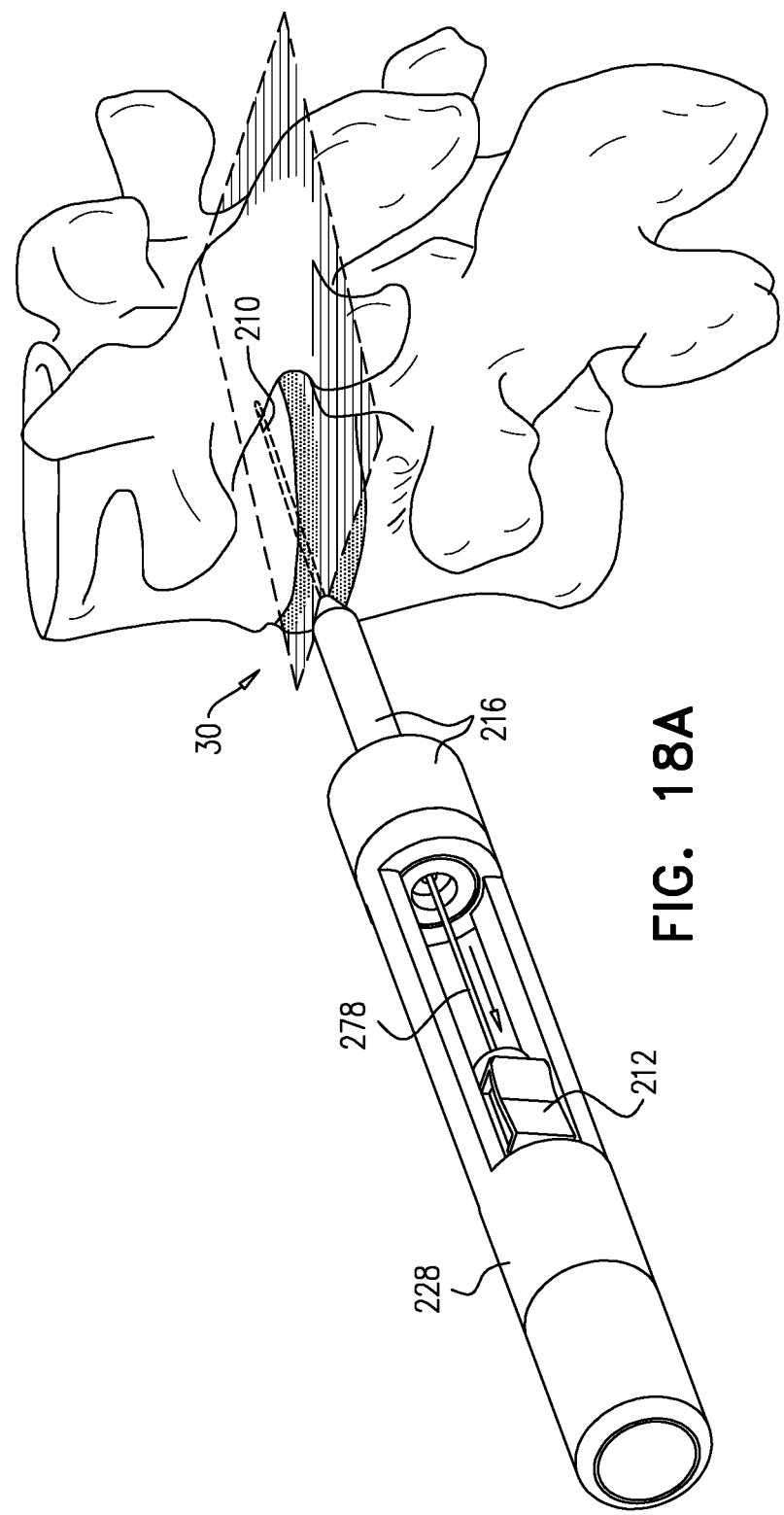

FIGS. 18A-C are schematic illustrations of an insertion-needle withdrawal step 286 of implantation method 240, in accordance with an application of the present invention. At insertion-needle withdrawal step 286, needle-connection fitting 212 is withdrawn proximally within needle-withdrawal handle 228, while needle-withdrawal handle 228 is held stationary. As mentioned above with reference to FIGS. 11A-B, insertion needle 210 is axially fixed to needle-connection fitting 212. As a result, needle-connection fitting 212, as it is proximally withdrawn, withdraws insertion needle 210 from disc 30 (insertion needle 210 is slidable with respect to spacer 216). Handle stylet 278, which is axially fixed with respect to needle-withdrawal handle 228 and abuts the proximal end of electrode 22, prevents proximal motion of electrode 22. As a result, electrode 22 remains generally axially stationary, partially inserted in disc 30.

Figure 19:
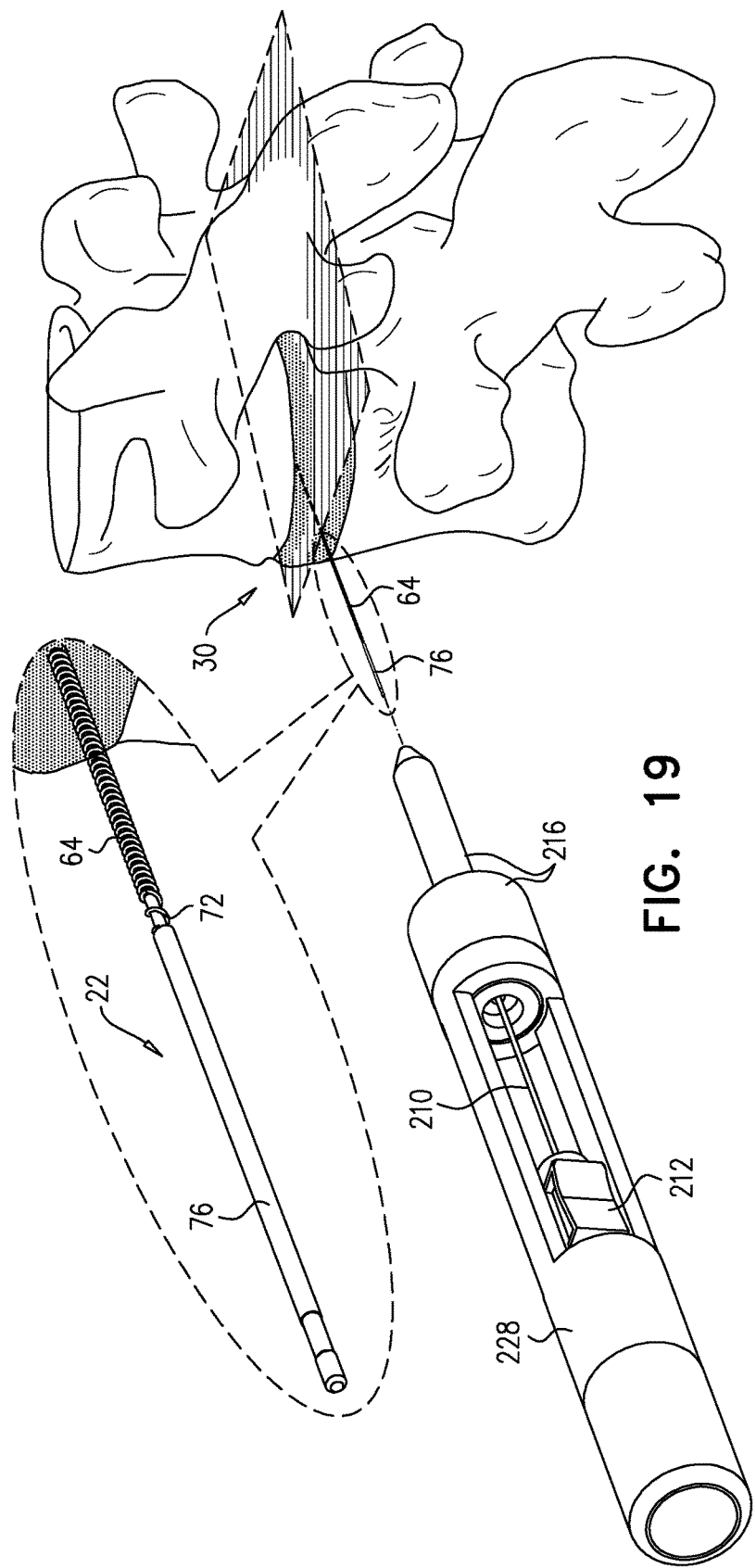
FIG. 19 is a schematic illustration of a needle-withdrawal-handle withdrawal step of the implantation method of FIG. 10, in accordance with an application of the present invention.

FIG. 19 is a schematic illustration of a needle-withdrawal-handle withdrawal step 290 of implantation method 240, in accordance with an application of the present invention. At needle-withdrawal-handle withdrawal step 290, needle-withdrawal handle 228, with spacer 216 still attached thereto, is gently withdrawn proximally, thereby releasing electrode 22 and leaving electrode 22 implanted partially in disc 30 and partially in the body of the subject outside the disc.

Figure 20:
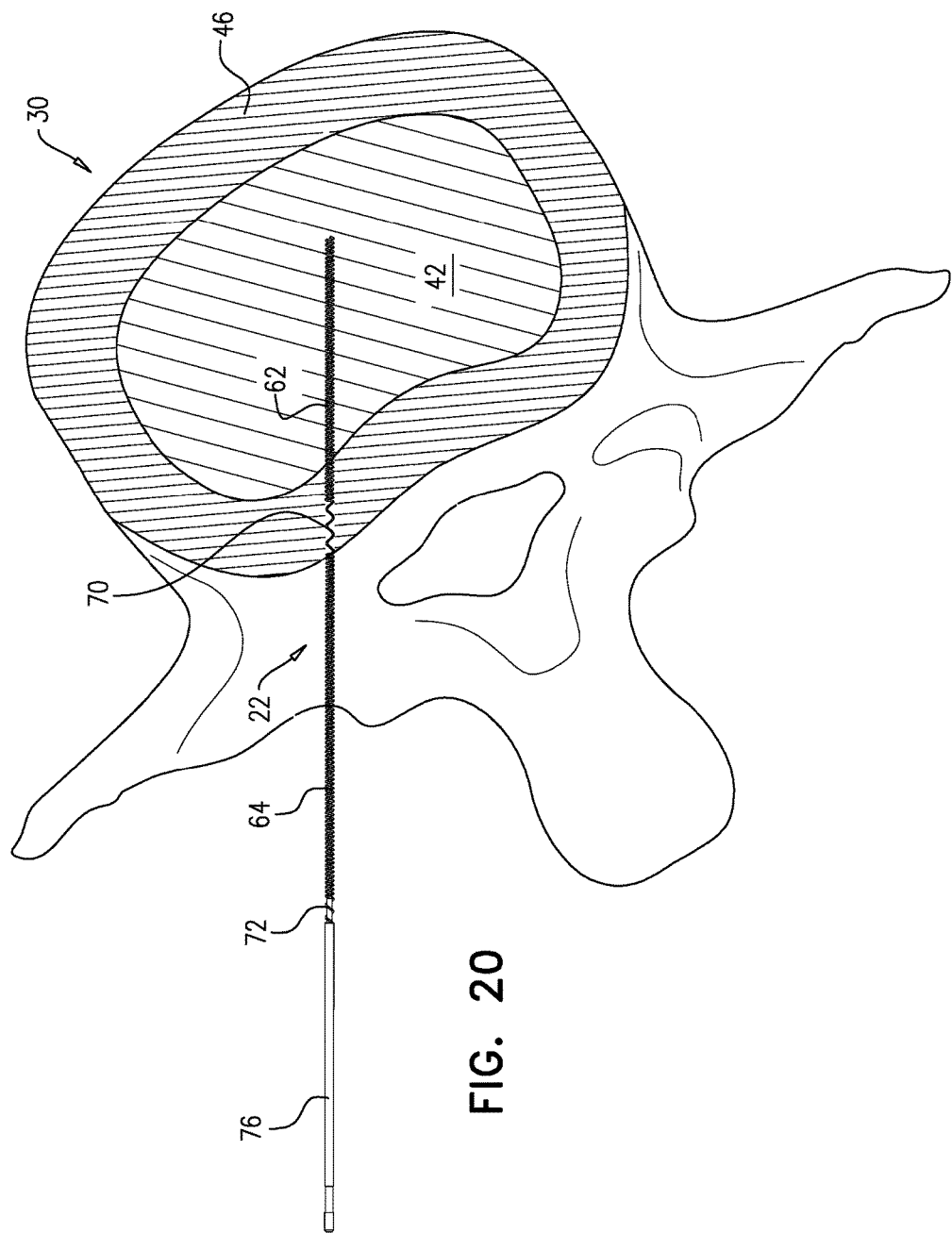
FIG. 20 is a schematic illustration of the electrode of FIG. 2 implanted partially in the disc and partially in the body of the subject outside the disc, in accordance with an application of the present invention.

FIG. 20 is a schematic illustration of electrode 22 implanted partially in disc 30 and partially in the body of the subject outside the disc, in accordance with an application of the present invention. For example, about 2 cm of electrode 22 may be disposed in disc 30, and the remainder (e.g., about 5 to 6 cm) may be disposed outside the disc.

Reference is again made to FIG. 1. In some applications of the present invention, intervertebral-disc-treatment system 20 comprises:
- at least one intra-pulposus exposed electrode surface 280 (which is electrically conductive), which is configured to be implanted in nucleus pulposus 42 of intervertebral disc 30;
- a plurality of extra-pulposus exposed electrode surfaces 44 (e.g., at least 3, no more than 10, and/or between 3 and 10, such as exactly 3), which are configured to be implanted outside nucleus pulposus 42, in electrical communication with intervertebral disc 30; and
- control circuitry 50, which is (a) electrically coupled to the at least one intra-pulposus exposed electrode surface 280 and the plurality of extra-pulposus exposed electrode surfaces 44, (b) configured to separately control at least two of the plurality of extra-pulposus exposed electrode surfaces 44; for example, control circuitry 50 may be electrically coupled to the extra-pulposus exposed electrode surfaces separately via separate electrical conductors.

Providing the plurality of separately-controllable extra-pulposus exposed electrode surfaces 44 distributes the generation of hydrogen, thereby reducing any local build-up of hydrogen at any single electrode surface.

For some applications, control circuitry 50 is configured to:
- repeatedly assume a pressure-increasing mode of operation in alternation with an oxygen-generating mode of operation,
- in the pressure-increasing mode of operation, (a) configure the at least one intra-pulposus exposed electrode surface 280 to be a cathode, and one or more of the plurality of extra-pulposus exposed electrode surfaces 44 to be one or more respective anodes, and (b) electroosmotically drive fluid into nucleus pulposus 42 to increase pressure in intervertebral disc 30, by applying a first mean voltage of less than 1.23 V (sometimes known in the art as the "electrolysis voltage") (e.g., less than 1 V, such as less than 500 mV, e.g., less than 300 mV) between the at least one intra-pulposus exposed electrode surface 280 and the one or more of the plurality of extra-pulposus exposed electrode surfaces 44, and in the oxygen-generating mode of operation, (a) configure the at least one intra-pulposus exposed electrode surface 280 to be an anode, and the plurality of extra-pulposus exposed electrode surfaces 44 to be a respective plurality of cathodes, and (b) generate oxygen within nucleus pulposus 42 by electrolysis, by applying a second mean voltage of at least 1.23 V (e.g., at least 1.5 V, such as at least 2 V) between the at least one intra-pulposus exposed electrode surface 280 and the plurality of extra-pulposus exposed electrode surfaces 44.

The increase in fluid in nucleus pulposus 42 during the pressure-increasing mode of operation generally treats or prevents further degeneration of the disc caused at least in part by loss of fluid. The applied current may also help introduce nutritional substances into the disc. The generation of oxygen within nucleus pulposus 42 during the oxygen-generating mode generally treats hypoxia, which, if untreated, sometimes causes disc degeneration. The generation of oxygen may also improve glucose metabolism, while reducing lactic acid generation.

For some applications, control circuitry 50 is configured to apply direct current, e.g., with an average amplitude of between 1 and 5 mA. For some applications, the control unit is configured to apply the direct current as a series of pulses. For some applications, the control unit is configured to apply the direct current as the series of pulses with a duty cycle of between 1% and 50%.

Typically, control circuitry 50 is not configured to actively balance the applied positive and negative charges. Rather, control circuitry 50 is configured to allow the passive balancing of the applied positive and negative charges.

Typically, control circuitry 50 is configured to separately control all of the plurality of extra-pulposus exposed electrode surfaces 44; for example, control circuitry 50 may be electrically coupled to the extra-pulposus exposed electrode surfaces separately via separate electrical conductors.

For some applications, as shown in FIG. 1, the at least one intra-pulposus exposed electrode surface 280 comprises non-electrically-insulated current-application longitudinal segment 62 of electrode 22, described hereinabove. Alternatively, the at least one intra-pulposus exposed electrode surface 280 does not comprise non-electrically-insulated current-application longitudinal segment 62 of electrode 22; instead, another electrode is provided; for example, electrodes may be used that are described in U.S. Pat. No. 8,577,469 and/or U.S. application Ser. No. 14/982,187, filed Dec. 29, 2015, which published as US Patent Application Publication 2017/0182317, both of which are assigned to the assignee of the present application and incorporated herein by reference, and are optionally implanted during a conventional surgical procedure to repair disc 30 and/or nucleus pulposus 42, including a standard approach for inserting a needle in disc 30. Alternatively, an electrode known in the art is used.

For some applications, control circuitry 50 is configured, during a period of time, to assume (a) the pressure-increasing mode of operation at least 10 times for an aggregate first duration and (b) the oxygen-generating mode of operation at least 10 times for an aggregate second duration that is less than 10% (e.g., less than 5%, such as less than 1%) of the aggregate first duration. By way of example and not limitation, control circuitry 50 may assume the oxygen-generating mode of operation for 1-30 seconds (e.g., 1-30 seconds every hour), and assume the pressure-increasing mode of operation at other times. Although control circuitry 50, when in the oxygen-generating mode of operation, may electroosmotically drive fluid out of nucleus pulposus 42 and thus decrease pressure in intervertebral disc 30, because the aggregate second duration is so much less than the aggregate first duration, the aggregate effect of the application of voltages is an increase in pressure in intervertebral disc 30.

For some applications, control circuitry 50 is configured to, in the oxygen-generating mode of operation, generate oxygen within nucleus pulposus 42 by electrolysis, by applying the second mean voltage between the at least one intra-pulposus exposed electrode surface 280 and respective different subsets of the plurality of extra-pulposus exposed electrode surfaces 44 at respective different times. For some applications, each of the subsets consists of exactly one of the plurality of extra-pulposus exposed electrode surfaces 44. Activating extra-pulposus exposed electrode surfaces 44 at different times further distributes the generation of hydrogen, thereby further reducing any local build-up of hydrogen at any single electrode surface.

For some applications, intervertebral-disc-treatment system 20 further comprises a sensor, which is configured to sense a parameter indicative of a quantity of the oxygen generated by the electrolysis. Control circuitry 50 is configured to modulate the oxygen-generating mode of operation responsively to the sensed parameter. For some applications, control circuitry 50 is configured to modulate the oxygen-generating mode of operation by modulating a duration of one or more occurrences of the oxygen-generating mode of operation. Alternatively or additionally, control circuitry 50 is configured to modulate the oxygen-generating mode of operation by modulating an electrical parameter of the second mean voltage (e.g., the voltage, amplitude, duty cycle, and/or frequency). For some applications, the sensed parameter is an oxygen concentration in nucleus pulposus 42 and/or a pH in nucleus pulposus 42. The sensor may be provided in the application of the present invention described immediately hereinbelow with reference to FIGS. 1 and 21.

Figure 21:
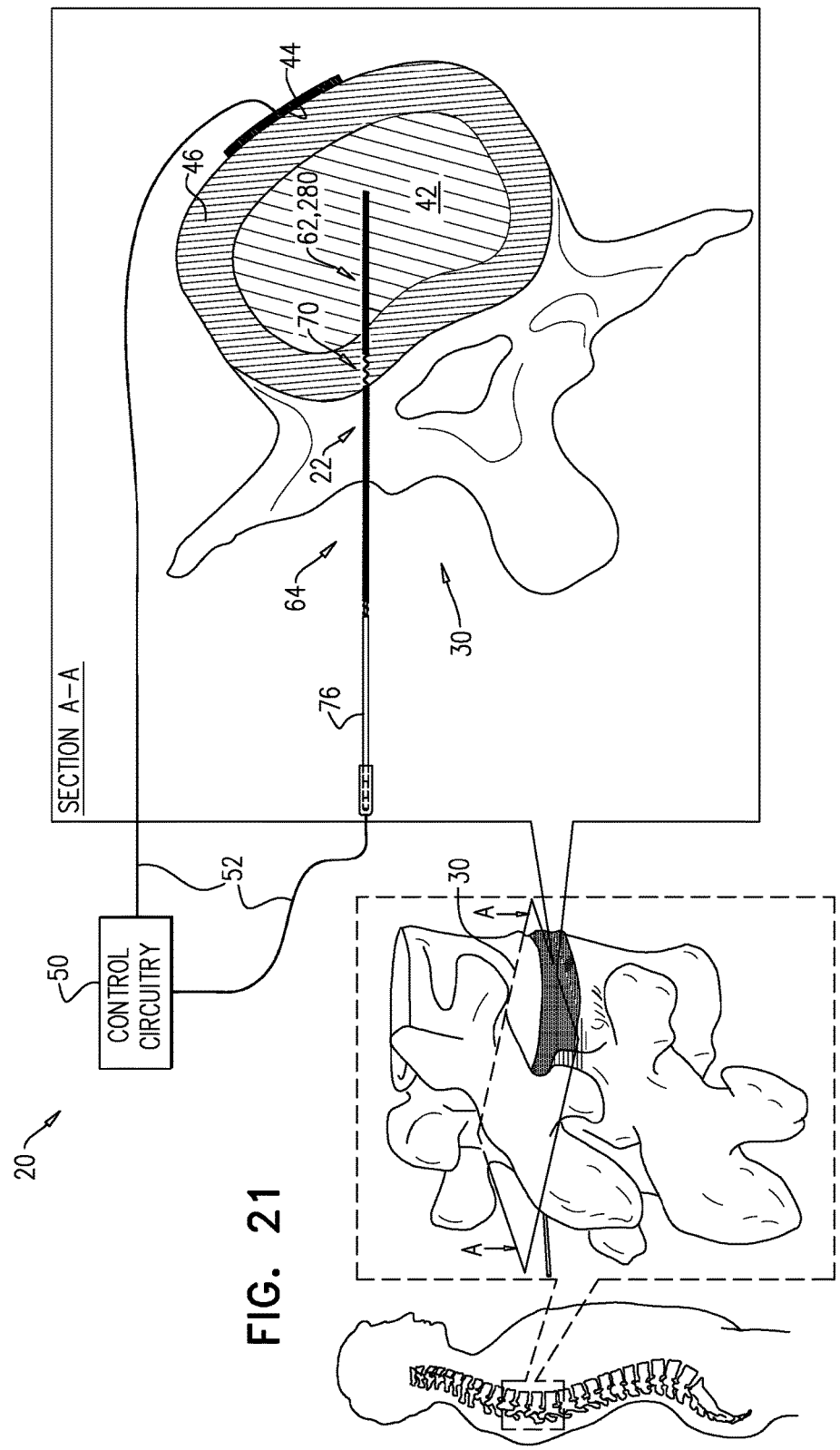
FIG. 21 is a schematic illustration of another configuration of the intervertebral-disc-treatment system of FIG. 1, in accordance with an application of the present invention.

Reference is still made to FIG. 1, and is additionally made to FIG. 21, which is a schematic illustration of another configuration of intervertebral-disc-treatment system 20, in accordance with an application of the present invention. In some applications of the present invention, intervertebral-disc-treatment system 20 comprises:

at least one intra-pulposus exposed electrode surface 280, which is configured to be implanted in nucleus pulposus 42 of intervertebral disc 30;

one or more extra-pulposus exposed electrode surfaces 44, which (a) are configured to be implanted outside nucleus pulposus 42, in electrical communication with intervertebral disc 30, and (b) have an aggregate electrically-exposed surface area of at least 3 cm2, such as at least 4 cm2, e.g., at least 5 cm2; and control circuitry 50, which is electrically coupled to the at least one intra-pulposus exposed electrode surface 280 and one or more extra-pulposus exposed electrode surfaces 44.

For some applications, control circuitry 50 is configured to:

repeatedly assume a pressure-increasing mode of operation in alternation with an oxygen-generating mode of operation, in the pressure-increasing mode of operation, (a) configure the at least one intra-pulposus exposed electrode surface 280 to be a cathode, and the one or more extra-pulposus exposed electrode surfaces 44 to be one or more respective anodes, and (b) electroosmotically drive fluid into nucleus pulposus 42 to increase pressure in intervertebral disc 30, by applying a first mean voltage of less than 1.23 V (e.g., less than 1 V, such as less than 500 mV, e.g., less than 300 mV) between the at least one intra-pulposus exposed electrode surface 280 and the one or more extra-pulposus exposed electrode surfaces 44, and in the oxygen-generating mode of operation, (a) configure the at least one intra-pulposus exposed electrode surface 280 to be an anode, and the one or more extra-pulposus exposed electrode surfaces 44 to be a respective plurality of cathodes, and (b) generate oxygen within nucleus pulposus 42 by electrolysis, by applying a second mean voltage of at least 1.23 V (e.g., at least 2 V) between the at least one intra-pulposus exposed electrode surface 280 and the one or more extra-pulposus exposed electrode surfaces 44.

The increase in fluid in nucleus pulposus 42 during the pressure-increasing mode of operation generally treats or prevents further degeneration of the disc caused at least in part by loss of fluid. The applied current may also help introduce nutritional substances into the disc. The generation of oxygen within nucleus pulposus 42 during the oxygen-generating mode generally treats hypoxia, which, if untreated, sometimes causes disc degeneration. The generation of oxygen may also improve glucose metabolism, while reducing lactic acid generation. Providing the relatively large aggregate electrically-exposed surface area of at least 3 cm2 distributes the generation of hydrogen, thereby reducing any local build-up of hydrogen at the electrode-tissue interface.

For some applications, such as shown in FIG. 21, intervertebral-disc-treatment system 20 comprises exactly one extra-pulposus exposed electrode surface 44 having an electrically-exposed surface area of at least 3 cm2. Alternatively, an external surface of a can of control circuitry 50 serves as extra-pulposus exposed electrode surface 44 (configuration not shown). For other applications, such as shown in FIG. 1, intervertebral-disc-treatment system 20 comprises a plurality of extra-pulposus exposed electrode surfaces 44.

For some applications, control circuitry 50 is configured to apply direct current, e.g., with an average amplitude of between 1 and 5 mA. For some applications, the control unit is configured to apply the direct current as a series of pulses. For some applications, the control unit is configured to apply the direct current as the series of pulses with a duty cycle of between 1% and 50%.

For some applications, control circuitry 50 is configured, during a period of time, to assume (a) the pressure-increasing mode of operation at least 10 times for an aggregate first duration and (b) the oxygen-generating mode of operation at least 10 times for an aggregate second duration that is less than 10% (e.g., less than 5%, such as less than 1%) of the aggregate first duration. By way of example and not limitation, control circuitry 50 may assume the oxygen-generating mode of operation for a few seconds every hour, and assume the pressure-increasing mode of operation at other times. Although control circuitry 50, when in the oxygen-generating mode of operation, may electroosmotically drive fluid out of nucleus pulposus 42 and thus decrease pressure in intervertebral disc 30, because the aggregate second duration is so much less than the aggregate first duration, the aggregate effect of the application of voltages is an increase in pressure in intervertebral disc 30.

Reference is again made to FIGS. 1 and 21. For some applications, control circuitry 50 is configured to drive intra-pulposus exposed electrode surface 280 and the one or more extra-pulposus exposed electrode surfaces 44 to electroosmotically drive fluid between inside and outside nucleus pulposus 42 based on a circadian cycle of the subject. For some applications, a housing containing control circuitry 50 is injectable, with an anchor at the proximal end. One or more extra-pulposus exposed electrode surfaces 44 are fixed to an external surface of the housing. For example, the housing may be implanted immediately posterior to the spinal column. For some applications, control circuitry 50 is configured to be implanted subcutaneously, if the housing containing the control circuitry is small. Alternatively, for some applications, control circuitry 50 is configured to be implanted or elsewhere in the subject's body, if the housing of the control circuitry is larger (e.g., includes batteries).

For some applications, control circuitry 50 is driven by an external controller that is in wireless or wired communication with control circuitry 50. For some applications, the external controller is mounted on a bed of the subject (e.g., disposed within a mattress), and is configured to activate control circuitry 50 only at night, and/or only when the subject is sleeping. Such nighttime activation may coincide with and support the filling phase of the disc, and thus be therapeutic even though the patient experiences more pain during the day. Alternatively or additionally, control circuitry 50 is activated during the daytime, i.e., over the course of the day, because the pressure is higher in the disc during application of vertical and mechanical load on the disc, which causes the disc to lose fluid; the activation may this reduce maximum damage to the disc. Further alternatively, the control circuitry is activated generally constantly or regularly intermittently (e.g., one hour on/one hour off). For some applications, control circuitry 50 is activated during rest of the subject, rather than during activity; for example, an accelerometer may be provided to identify movement vs. rest of the subject.

For some applications, control circuitry 50 is configured to provide the subject with control of activation of control circuitry 50, e.g., in response to activity or pain. For example, the control may be provided from the subject's telephone (e.g., smartphone) or other electronic device.

For some applications, the method further comprises replacing nucleus pulposus 42 with an artificial substitute material before implanting intra-pulposus exposed electrode surface 280.

A first experiment was conducted on behalf of the inventors to study the feasibility of using some of the techniques described hereinabove with reference to FIG. 1 to hydrate and dehydrate a spinal disc, and the impact of the voltage application on the disc mass. The experiment evaluated three electrical protocols: (a) negative voltage inside the nucleus pulposus of the disc vs. outside the disc, (b) positive voltage inside the nucleus pulposus of the disc vs. outside the disc, and (c) control (no voltage applied to the nucleus pulposus of the disc). It was found that application of a negative voltage inside the nucleus pulposus of the disc enhanced the hydration of the disc, as compared to a positive voltage or no voltage. No dehydration effect was observed with application of a positive voltage to the nucleus pulposus.

The experiment used a total of six fresh bovine tail discs. In order to achieve equilibrium, the discs were placed in a saline solution for a period of one hour prior to application of the voltages. The discs were then weighed. The discs were randomly assigned to the experimental groups as follows: (a) two specimens—negative voltage inside the nucleus pulposus of the disc vs. outside the disc, (b) two specimens—positive voltage inside the nucleus pulposus of the disc vs. outside the disc, and (c) two specimens—control (no voltage applied to the nucleus pulposus of the disc).

The discs were placed inside a vessel and fully submerged in saline solution. One electrode was inserted in the approximate center of the nucleus pulposus of each of the discs in experimental groups (a) and (b). The electrode was electrically-insulated except at its tip, and was designed to allow submersion in liquid. The electrode was inserted laterally (i.e., through the annulus of the disc). A second, ring electrode was placed within the saline solution surrounding the disc.

Voltages of (a) −1 V and (b) +1 V were applied between the electrodes in the two experimental groups (a) and (b), respectively. These voltages were selected to be lower than the electrolysis voltage of water of about 1.2 V. After a period of two hours, the discs were removed and weighed again.

As set forth in Table 1 below, all of the discs increased in mass during the voltage-application period. The mass of the discs to which the negative internal voltage was applied increased by 4.7% and 5.5%, while the mass of the other discs (positive internal voltage and control) increased by between 2.0% and 2.6%.

The inventors hypothesize that all of the discs absorbed liquid, while the application of the negative internal voltage contributed to an additional absorption of 2-3%. The application of the positive internal voltage did not result in dehydration of the disc.

TABLE 1

| Disc # | Mass after 1 hour immersion [g] | Voltage (internal) | Mass after 2 hours voltage application [g] | Mass change [g] | Mass change [%] |
|---|---|---|---|---|---|
| 1 | 3.342 | −1 V | 3.527 | 0.185 | 5.5% |
| 2 | 4.384 | −1 V | 4.590 | 0.206 | 4.7% |
| 3 | 6.552 | +1 V | 6.720 | 0.168 | 2.6% |
| 4 | 4.558 | +1 V | 4.651 | 0.093 | 2.0% |
| 5 | 7.346 | 0 | 7.531 | 0.185 | 2.5% |
| 6 | 6.074 | 0 | 6.209 | 0.135 | 2.2% |

A second experiment was conducted on behalf of the inventors to study the feasibility of using some of the techniques described hereinabove with reference to FIG. 1 to hydrate a spinal disc and the impact of the voltage application on the disc mass. The experiment evaluated two electrical protocols: (a) negative voltage inside the nucleus pulposus of the disc vs. outside the disc, and (b) control (no voltage applied to the nucleus pulposus of the disc). It was found that application of a negative voltage inside the nucleus pulposus of the disc enhanced the hydration of the disc, as compared to no voltage. Higher voltage markedly increased the mass gain.

The experiment used a total of six fresh bovine tail discs. The discs were randomly assigned to the experimental groups as follows: (a) three specimens—negative voltage inside the nucleus pulposus of the disc vs. outside the disc, and (b) three specimens—control (no voltage applied to the nucleus pulposus of the disc).

The discs were weighed, and then placed inside a vessel and fully submerged in saline solution. One electrode was inserted in the approximate center of the nucleus pulposus of each of the discs in the experimental group (a). The electrode was electrically-insulated except at its tip, and was designed to allow submersion in liquid. The electrode was inserted laterally (i.e., through the annulus of the disc). A second, ring electrode was placed within the saline solution surrounding the disc.

A voltage of −1 V was applied between the electrodes in the experimental group (a). One hour after the beginning of application of the voltage, a first pair of two of the discs (one negative voltage, one control) were removed and weighed. In the two remaining negative voltage discs, the voltage was increased to −3 V.

Two hours after the beginning of application of the voltage, a second pair of two of the discs (one negative voltage, one control) were removed and weighed.

Three hours after the beginning of application of the voltage, a third pair of two of the discs (one negative voltage, one control) were removed and weighed.

As set forth in Table 2 below, all of the discs increased in mass during the voltage-application period. In each pair, the disc to which the voltage was applied increased in mass more than the control disc did. Increasing the voltage from −1 V to −3 V resulted in a markedly increased mass gain. It was noted, however, that the −3 V voltage application resulted in electrolysis of the solution, which was expected since the electrolysis threshold of water is about 1.2 V. This electrolysis was observed as bubbles and discoloration in the solution.

The inventors hypothesize that all of the discs absorbed liquid, while the application of the negative internal voltage contributed to an additional absorption.

TABLE 2

| Disc # | Starting mass [g] | Voltage (internal) | Duration of voltage application | Ending mass [g] | Mass change [%] |
|---|---|---|---|---|---|
| 1 | 6.047 | −1 V | 1 hour | 6.345 | 4.93% |
| 2 | 6.227 | 0 | 1 hour | 6.420 | 3.10% |
| 3 | 5.988 | −1 V, −3 V | 2 hours | 6.605 | 10.30% |
| 4 | 5.192 | 0 | 2 hours | 5.444 | 4.85% |
| 5 | 4.484 | −1 V, −3 V | 3 hours | 5.262 | 17.35% |
| 6 | 4.236 | 0 | 3 hours | 4.619 | 9.04% |

The inventors hypothesize that application of −3 V, although possibly not suitable for clinical use, served as a proxy for the effectiveness of longer-term voltage application at a lower voltage, such as −1 V.

As mentioned above, the discs were placed in a saline-dye solution during the experiment. The dye was methylene blue. After weighing the discs, the discs were also dissected and inspected for dye penetration. In general, dye penetration was not observed in the discs.

Figure 22:
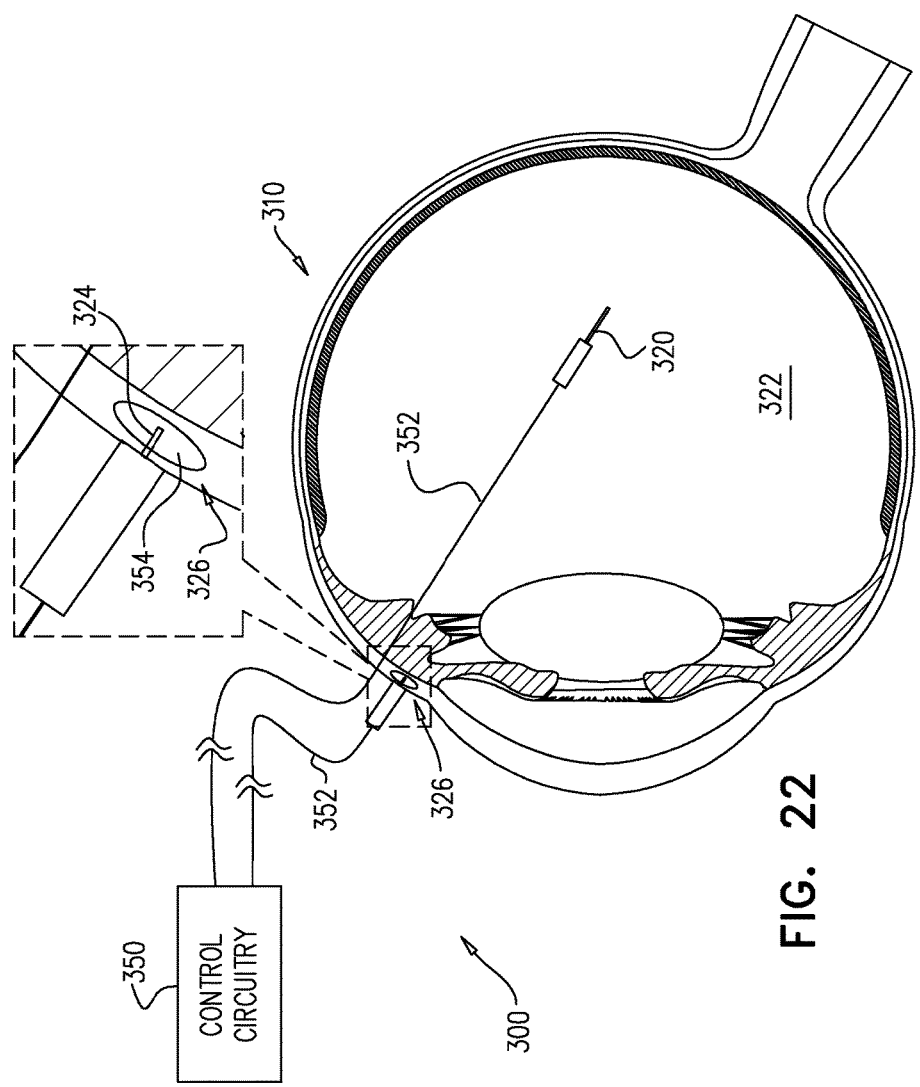
FIG. 22 is a schematic illustration of an eye-treatment system for treating an eye of a subject, in accordance with an application of the present invention.

Reference is now made to FIG. 22, which is a schematic illustration of an eye-treatment system 300 for treating an eye 310 of a subject, in accordance with an application of the present invention. Eye-treatment system 300 is typically used for treating glaucoma. Eye-treatment system 300 comprises:

a first exposed electrode surface 320, which is configured to be implanted in a vitreous cavity 322 of eye 310;

a second exposed electrode surface 324, which is configured to be implanted in a body of the subject at a site 326 outside vitreous cavity 322; and control circuitry 350, which is typically electrically coupled, by one or more electrode leads 352, to first and second exposed electrode surfaces 320 and 324.

For some applications, control circuitry 350 is configured to:

repeatedly assume a pressure-decreasing mode of operation in alternation with an oxygen-generating mode of operation, in both the pressure-decreasing mode of operation and the oxygen-generating mode of operation, configure first exposed electrode surface 320 to be an anode, and second exposed electrode surface 324 to be a cathode, in the pressure-decreasing mode of operation, electroosmotically drive fluid from vitreous cavity 322 to outside vitreous cavity 322 to decrease pressure in vitreous cavity 322, by applying a first mean voltage of less than 1.23 V (e.g., less than 1 V, such as less than 500 mV, e.g., less than 300 mV) between first and second exposed electrode surfaces 320 and 324, and in the oxygen-generating mode of operation, generate oxygen within vitreous cavity 322 by electrolysis, by applying a second mean voltage of at least 1.23 V (e.g., at least 2 V) between first and second exposed electrode surfaces 320 and 324.

The decrease in fluid in vitreous cavity 322 during the pressure-decreasing mode of operation generally treats glaucoma by reducing intraocular pressure. The generation of oxygen within vitreous cavity 322 during the oxygen-generating mode treats diabetic retinopathy, in which insufficient oxygen is naturally provided to the retina.

For some applications, site 326 is within a Schlemm's canal 354 of the subject, and second exposed electrode surface 324 is configured to be implanted within Schlemm's canal 354. In these applications, control circuitry 50 is configured to, in the pressure-decreasing mode of operation, electroosmotically drive the fluid from vitreous cavity 322 to Schlemm's canal 354 to decrease the pressure in vitreous cavity 322, by applying the first mean voltage between first and second exposed electrode surfaces 320 and 324.

For some applications, control circuitry 50 is configured, during a period of time, to assume (a) the pressure-decreasing mode of operation at least 10 times for an aggregate first duration and (b) the oxygen-generating mode of operation at least 10 times for an aggregate second duration that is less than 10% (e.g., less than 5%, such as less than 1%) of the aggregate first duration.

For some applications, control circuitry 50 is configured to apply direct current, e.g., with an average amplitude of between 1 and 5 mA. For some applications, the control unit is configured to apply the direct current as a series of pulses. For some applications, the control unit is configured to apply the direct current as the series of pulses with a duty cycle of between 1% and 50%.

For some applications, eye-treatment system 300 further comprises a sensor, which is configured to sense a parameter indicative of a quantity of the oxygen generated by the electrolysis. Control circuitry 50 is configured to modulate the oxygen-generating mode of operation responsively to the sensed parameter. For some applications, control circuitry 50 is configured to modulate the oxygen-generating mode of operation by modulating a duration of one or more occurrences of the oxygen-generating mode of operation. Alternatively or additionally, control circuitry 50 is configured to modulate the oxygen-generating mode of operation by modulating an electrical parameter of the second mean voltage (e.g., the voltage, amplitude, duty cycle, and/or frequency). For some applications, the sensed parameter is an oxygen concentration in vitreous cavity 322 and/or a pH in vitreous cavity 322.

For some applications, control circuitry 50 is configured to detect a pressure difference between vitreous cavity 322 and outside vitreous cavity 322, and modulate the pressure-decreasing mode of operation responsively to the pressure difference parameter in response to the detected pressure difference.

Reference is now made to FIG. 23, which is a schematic illustration of a diabetic-retinopathy-treatment system 400 for treating diabetic retinopathy, in accordance with an application of the present invention. Diabetic-retinopathy-treatment system 400 comprises control circuitry 420 and one or more electrodes 430 (e.g., at least 2, no more than 20, and/or between 2 and 20). The one or more electrodes 430 are configured to be implanted penetrating a retina 440 of eye 310 (as shown), or placed against an external surface of retina 440 (i.e., the surface facing into the interior of the eye) (configuration not shown).

Control circuitry 420 is configured to generate oxygen within retina 440 by electrolysis, by (a) configuring the one or more electrodes 430 to be anodes, and (b) applying a mean voltage of at least 1.23 V (e.g., at least 1.5 V, such as at least 2 V) between the one or more electrodes 430 and one or more return cathodes 444 (e.g., an electrically-conductive casing of control circuitry 420). The generated oxygen treats diabetic retinopathy, which is characterized by damage to blood vessels in the retina, which reduces the oxygen supply to the retina.

For some applications, diabetic-retinopathy-treatment system 400 comprises an antenna 446, which is configured to wirelessly receive energy for powering control circuitry 420. For example, antenna 446 may have an annular shape and be mounted around a lens 448 of the eye, either the natural lens or an intraocular lens (IOL) that is implanted to serve as a support for antenna 446. Alternatively, antenna 446 has a different structure and/or is implanted at a different site in the eye or near the eye. Antenna 446 may be connected to control circuitry 420 by one or more conductive wires 449.

Typically, electrodes 430 are implanted near a macula 442 of retina 440, most typically not on macula 442 itself, in order to avoid interfering with the patient's vision. For example, as shown, diabetic-retinopathy-treatment system 400 may comprise a ring 450 that is sized to be placed around macula 442, and electrodes 430 are fixed at different respective sites along ring 450 around macula 442. Optionally, control circuitry 420 is also disposed along, or slightly outside, ring 450.

In some applications of the present invention, the techniques and apparatus described herein are combined with techniques and apparatus described in one or more of the following applications, which are assigned to the assignee of the present application and are incorporated herein by reference:

U.S. Pat. No. 8,577,469 to Gross;

US Patent Application Publication 2014/0324128 to Gross; and

U.S. patent application Ser. No. 14/982,187, filed Dec. 29, 2015, which published as US Patent Application Publication 2017/0182317.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating an intervertebral disc of a subject, the apparatus comprising:
   at least one intra-pulposus exposed electrode surface, which is configured to be implanted in a nucleus pulposus of the intervertebral disc;
   a plurality of extra-pulposus exposed electrode surfaces, which are configured to be implanted outside the nucleus pulposus, in electrical communication with the intervertebral disc; and
   control circuitry, which is (a) electrically coupled to the at least one intra-pulposus exposed electrode surface and the plurality of extra-pulposus exposed electrode surfaces, (b) configured to separately control at least two of the plurality of extra-pulposus exposed electrode surfaces, and (c) configured to:
   repeatedly assume a pressure-increasing mode of operation in alternation with an oxygen-generating mode of operation,
   in the pressure-increasing mode of operation, (a) configure the at least one intra-pulposus exposed electrode surface to be a cathode, and one or more of the plurality of extra-pulposus exposed electrode surfaces to be one or more respective anodes, and (b) electroosmotically drive fluid into the nucleus pulposus to increase pressure in the intervertebral disc, by applying a first mean voltage of less than 1.23 V between the at least one intra-pulposus exposed electrode surface and the one or more of the plurality of extra-pulposus exposed electrode surfaces, and
   in the oxygen-generating mode of operation, (a) configure the at least one intra-pulposus exposed electrode surface to be an anode, and the plurality of extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the plurality of extra-pulposus exposed electrode surfaces.

2. The apparatus according to claim 1, wherein the control circuitry is configured to separately control all of the plurality of extra-pulposus exposed electrode surfaces.

3. The apparatus according to claim 1, wherein the first mean voltage is less than 500 mV.

4. The apparatus according to claim 1, wherein the second mean voltage is at least 2 V.

5. The apparatus according to claim 1, wherein the control circuitry is configured, during a period of time, to assume (a) the pressure-increasing mode of operation at least 10 times for an aggregate first duration and (b) the oxygen-generating mode of operation at least 10 times for an aggregate second duration that is less than 10% of the aggregate first duration.

6. The apparatus according to claim 5, wherein the aggregate second duration is less than 1% of the aggregate first duration.

7. The apparatus according to claim 1, wherein the plurality of extra-pulposus exposed electrode surfaces comprises at least three extra-pulposus exposed electrode surfaces.

8. The apparatus according to claim 1, wherein the control circuitry is configured to, in the oxygen-generating mode of operation, generate oxygen within the nucleus pulposus by electrolysis, by applying the second mean voltage between the at least one intra-pulposus exposed electrode surface and respective different subsets of the plurality of extra-pulposus exposed electrode surfaces at respective different times.

9. The apparatus according to claim 8, wherein each of the subsets consists of exactly one of the plurality of extra-pulposus exposed electrode surfaces.

10. The apparatus according to claim 1,
    wherein the apparatus further comprises a sensor, which is configured to sense a parameter indicative of a quantity of the oxygen generated by the electrolysis, and
    wherein the control circuitry is configured to modulate the oxygen-generating mode of operation responsively to the sensed parameter.

11. The apparatus according to claim 10, wherein the sensed parameter is an oxygen concentration in the nucleus pulposus.

12. The apparatus according to claim 10, wherein the sensed parameter is a pH in the nucleus pulposus.

13. Apparatus for treating an intervertebral disc of a subject, the apparatus comprising:
    at least one intra-pulposus exposed electrode surface, which is configured to be implanted in a nucleus pulposus of the intervertebral disc;
    one or more extra-pulposus exposed electrode surfaces, which (a) are configured to be implanted outside the nucleus pulposus, in electrical communication with the intervertebral disc, and (b) have an aggregate electrically-exposed surface area of at least 1 cm2; and
    control circuitry, which is (a) electrically coupled to the at least one intra-pulposus exposed electrode surface and one or more extra-pulposus exposed electrode surfaces, and (b) configured to:
    repeatedly assume a pressure-increasing mode of operation in alternation with an oxygen-generating mode of operation,
    in the pressure-increasing mode of operation, (a) configure the at least one intra-pulposus exposed electrode surface to be a cathode, and the one or more extra-pulposus exposed electrode surfaces to be one or more respective anodes, and (b) electroosmotically drive fluid into the nucleus pulposus to increase pressure in the intervertebral disc, by applying a first mean voltage of less than 1.23 V between the at least one intra-pulposus exposed electrode surface and the one or more extra-pulposus exposed electrode surfaces, and
    in the oxygen-generating mode of operation, (a) configure the at least one intra-pulposus exposed electrode surface to be an anode, and the one or more extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the one or more extra-pulposus exposed electrode surfaces.

14. The apparatus according to claim 13, wherein the aggregate electrically-exposed surface area is at least 3 cm2.

15. The apparatus according to claim 13, wherein the first mean voltage is less than 500 mV.

16. The apparatus according to claim 13, wherein the second mean voltage is at least 2 V.

17. The apparatus according to claim 13, wherein the control circuitry is configured, during a period of time, to assume (a) the pressure-increasing mode of operation at least 10 times for an aggregate first duration and (b) the oxygen-generating mode of operation at least 10 times for an aggregate second duration that is less than 10% of the aggregate first duration.

18. The apparatus according to claim 17, wherein the aggregate second duration is less than 1% of the aggregate first duration.

19. The apparatus according to claim 13, wherein the apparatus comprises exactly one extra-pulposus exposed electrode surface having an electrically-exposed surface area of at least 1 cm2.

20. The apparatus according to claim 19, wherein the surface area of the of the exactly one extra-pulposus exposed electrode surface is at least 3 cm2.

21. The apparatus according to claim 13, wherein the apparatus comprises a plurality of extra-pulposus exposed electrode surfaces.

22. The apparatus according to claim 13,
wherein the apparatus further comprises a sensor, which is configured to sense a parameter indicative of a quantity of the oxygen generated by the electrolysis, and
wherein the control circuitry is configured to modulate the oxygen-generating mode of operation responsively to the sensed parameter.

23. The apparatus according to claim 22, wherein the sensed parameter is an oxygen concentration in the nucleus pulposus.

24. The apparatus according to claim 22, wherein the sensed parameter is a pH in the nucleus pulposus.

25. A method for treating an intervertebral disc of a subject, the method comprising:
implanting at least one intra-pulposus exposed electrode surface in a nucleus pulposus of the intervertebral disc;
implanting a plurality of extra-pulposus exposed electrode surfaces outside the nucleus pulposus, in electrical communication with the intervertebral disc; and
activating control circuitry, which is (a) electrically coupled to the at least one intra-pulposus exposed electrode surface and the plurality of extra-pulposus exposed electrode surfaces, and (b) configured to separately control at least two of the plurality of extra-pulposus exposed electrode surfaces, to:
repeatedly assume a pressure-increasing mode of operation in alternation with an oxygen-generating mode of operation,
in the pressure-increasing mode of operation, (a) configure the at least one intra-pulposus exposed electrode surface to be a cathode, and one or more of the plurality of extra-pulposus exposed electrode surfaces to be one or more respective anodes, and (b) electroosmotically drive fluid into the nucleus pulposus to increase pressure in the intervertebral disc, by applying a first mean voltage of less than 1.23 V between the at least one intra-pulposus exposed electrode surface and the one or more of the plurality of extra-pulposus exposed electrode surfaces, and
in the oxygen-generating mode of operation, (a) configure the at least one intra-pulposus exposed electrode surface to be an anode, and the plurality of extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the plurality of extra-pulposus exposed electrode surfaces.

26. A method for treating an intervertebral disc of a subject, the method comprising:
implanting at least one intra-pulposus exposed electrode surface in a nucleus pulposus of the intervertebral disc;
implanting one or more extra-pulposus exposed electrode surfaces outside the nucleus pulposus, in electrical communication with the intervertebral disc, the one or more extra-pulposus exposed electrode surfaces having an aggregate electrically-exposed surface area of at least 1 cm2; and
activating control circuitry, which is electrically coupled to the at least one intra-pulposus exposed electrode surface and one or more extra-pulposus exposed electrode surfaces, to:
repeatedly assume a pressure-increasing mode of operation in alternation with an oxygen-generating mode of operation,
in the pressure-increasing mode of operation, (a) configure the at least one intra-pulposus exposed electrode surface to be a cathode, and the one or more extra-pulposus exposed electrode surfaces to be one or more respective anodes, and (b) electroosmotically drive fluid into the nucleus pulposus to increase pressure in the intervertebral disc, by applying a first mean voltage of less than 1.23 V between the at least one intra-pulposus exposed electrode surface and the one or more extra-pulposus exposed electrode surfaces, and
in the oxygen-generating mode of operation, (a) configure the at least one intra-pulposus exposed electrode surface to be an anode, and the one or more extra-pulposus exposed electrode surfaces to be a respective plurality of cathodes, and (b) generate oxygen within the nucleus pulposus by electrolysis, by applying a second mean voltage of at least 1.23 V between the at least one intra-pulposus exposed electrode surface and the one or more extra-pulposus exposed electrode surfaces.

27. Apparatus comprising an electrode, which comprises a wire that (a) has a wire diameter of between 75 and 125 microns and (b) includes:
a non-electrically-insulated current-application longitudinal segment, which, in the absence of any applied forces, is coiled and has (i) a mean pitch of between 1.1 and 2 times the wire diameter, and (ii) an entire longitudinal length of between 5 and 35 mm, and
an electrically-insulated lead longitudinal segment, which has an entire longitudinal length of between 5 and 80 mm, in the absence of any applied forces.

* * * * *